US010961196B2

(12) United States Patent
Böttcher et al.

(10) Patent No.: US 10,961,196 B2
(45) Date of Patent: Mar. 30, 2021

(54) COMPOUNDS FOR USE AS AN ANTI-BACTERIAL OR ANTI-FUNGAL AGENT AND AS A ZINC SENSOR

(71) Applicant: UNIVERSITÄT KONSTANZ, Constance (DE)

(72) Inventors: Thomas Böttcher, Constance (DE); David Szamosvari, Constance (DE); Valentin Frederik Reichle, Constance (DE)

(73) Assignee: Universität Konstanz, Constance (DE)

( * ) Notice: Subject to any disclaimer, the term of this patent is extended or adjusted under 35 U.S.C. 154(b) by 0 days.

(21) Appl. No.: 16/311,502

(22) PCT Filed: Jun. 23, 2017

(86) PCT No.: PCT/EP2017/000735
§ 371 (c)(1),
(2) Date: Dec. 19, 2018

(87) PCT Pub. No.: WO2017/220205
PCT Pub. Date: Dec. 28, 2017

(65) Prior Publication Data
US 2019/0218183 A1 Jul. 18, 2019

(30) Foreign Application Priority Data

Jun. 24, 2016 (EP) .................................. 16001423

(51) Int. Cl.
A01N 43/18 (2006.01)
C07D 335/06 (2006.01)
C07D 215/233 (2006.01)
C07D 215/36 (2006.01)
C07D 215/42 (2006.01)
C07D 345/00 (2006.01)
C07D 211/22 (2006.01)
A01N 43/16 (2006.01)
A01N 43/42 (2006.01)
A01N 55/00 (2006.01)
C07D 311/24 (2006.01)
G01N 21/64 (2006.01)

(52) U.S. Cl.
CPC ......... C07D 215/233 (2013.01); A01N 43/16 (2013.01); A01N 43/18 (2013.01); A01N 43/42 (2013.01); A01N 55/00 (2013.01); C07D 211/22 (2013.01); C07D 215/36 (2013.01); C07D 215/42 (2013.01); C07D 311/24 (2013.01); C07D 335/06 (2013.01); C07D 345/00 (2013.01); G01N 21/64 (2013.01)

(58) Field of Classification Search
CPC ............................... C07D 335/06; A01N 43/18
USPC ......................................... 549/23; 514/432
See application file for complete search history.

(56) References Cited

U.S. PATENT DOCUMENTS 3,547,949 A * 12/1970 Malen Charles ............... 549/23

FOREIGN PATENT DOCUMENTS

WO 99/52890 A1 10/1999
WO 02/18342 A2 3/2002
WO 2004/092154 A1 10/2004
WO 2015/116492 A1 8/2015

OTHER PUBLICATIONS

Shen et al., "Palladium-Catalyzed, etc.," Angew. Chem. Int. Ed., 55, 5067-5070. (Year: 2016).*
Matsumoto et al., "Thiochronnones as, etc.," CA 83:109785. (Year: 1975).*
Hirao et al., "Reactions of, etc.," Bull. Chem. Soc. Jpn., 58, 2203-2206. (Year: 1985).*
Huang et al., "A New Synthetic, etc.," Heteroatom Chemistry, 6(3) 287-291. (Year: 1995).*
Nussbaumer et al., "2-Substituted, etc.," J. Med. Chem., 45, 4310-4320. (Year: 2002).*
Willy et al.,"Microwave-assisted, etc.," Org. Biomol. Chem.,8, 90-95. (Year: 2010).*
Yang et al., "Domino reactions, etc.," RSC Adv., 2, 6549-6554. (Year: 2012).*
Narayan et al., "Hypervalent, etc.," Chem. Eur, 20, 4568-4572 and supporting information, pp. 1-36. (Year: 2014).*
Inami et al.,"Nickel-catalyzed, etc.," Or. Lett, 16, 5660-5662 and supporting information, pp. S1-S78. (Year: 2014).*
Majumdar et al., "Thiochromenone, etc.," Monatshefte fur Chemie, 132, 739-746. (Year: 2001).*
Borges, M., et al., "Photobiological Properties of Hydroxy-Substituted Flavothiones", Photochemistry and Photobiology, 2002, vol. 75(2), pp. 97-106.
Calfee, M.W., et al., "Interference with Pseudomonas Quinolone Signal Synthesis Inhibits Virulence Factor Expression by Pseudomonas Aeruginosa", Proc. Natl. Acad. Sci. USA, 2001, vol. 98(20), pp. 11633-11637.
Cathcart, G.R., et al., "Inhibitor Profiling of the Pseudomonas Aeruginosa Virulence Factor LasB Using N-alpha Mercaptoamide Template-Based Inhibitors", Bioorganic & Medicinal Chemistry Letters, 2009, vol. 19(21), pp. 6230-6232, doi:10.1016/j.bmcl.2009.08.099, Epub Sep. 10, 2009. (Abstract only).
Detty, M.R., "Preparation of "Unnatural" Tellurium Analogues of Naturally Occurring Chromones and Flavones. The Control of Ipso vs. Ortho Acylation, Selective Demethylation, and Olefin-Forming Condensation Reactions in Benzo[b] tellurapyranones", Organometallics, 1988, vol. 7(10), pp. 2188-2197.
Majumdar, K.C., et al., "Synthesis of Thiochromen-4-one-annelated Heterocycles:Regioselective Cyclization of 3-Hydroxy-2-cyclohex-2'-enylthiochromen-4-one", Synthetic Communications, 2006, vol. 33(1), pp. 133-142, doi:10.1081/SCC-120015569.

(Continued)

Primary Examiner — Patricia L Morris
(74) Attorney, Agent, or Firm — McDonnell Boehnen Hulbert & Berghoff LLP

(57) ABSTRACT

The present invention relates to a compound, which can be used as an anti-bacterial and/or an anti-fungal agent as well as a zinc sensor. Moreover, the present invention relates to a pharmaceutical composition comprising said compound and methods for treating bacterial or fungal infections in mammals.

13 Claims, 9 Drawing Sheets

(56) References Cited

OTHER PUBLICATIONS

Mughal, Ehsan Ullah, et al., "Synthesis and Antibacterial Activity of Substituted Flavones, 4-Thioflavones and 4-Iminoflavones", Bioorganic & Medicinal Chemistry, 2006, vol. 14(14), pp. 4704-4711.
Nakazumi, Hiroyuki, et al., "Synthesis and Antibacterial Activity of 2-Phenyl-4H-benzo[b]thiopyran-4-ones and (Thioflavones) Related Compounds", J.Heterocyclic Chem., 1984, vol. 21(1), pp. 193-196.
Sashida, Haruki, "An Alternative Facile Preparation of Telluro- and Selenochromones from o-Bromophenyl Ethynyl Ketones", Synthesis, May 1998, pp. 745-748.
International Preliminary Report on Patentability, received from the International Bureau of WIPO, dated Jan. 3, 2019, for International Application No. PCT/EP2017/000735, pp. 1-11.
Szamosvári, D., et al., "A Thiochromenone Antibiotic Derived from the Pseudomonas Quinolone Signal Selectively Targets the Gram-Negative Pathogen Moraxella catarrhalis", Chem. Sci., 2019, vol. 10, pp. 6624-6628.

\* cited by examiner

US 10,961,196 B2

COMPOUNDS FOR USE AS AN ANTI-BACTERIAL OR ANTI-FUNGAL AGENT AND AS A ZINC SENSOR

CROSS-REFERENCE

This application is a section 371 U.S. National phase of PCT/EP2017/000735, filed Jun. 23, 2017 which claims priority from EP patent application No. 16001423.9, filed Jun. 24, 2016, which is incorporated by reference in its entirety.

FIELD OF THE INVENTION

The present invention relates to a compound, which can be used as an anti-bacterial and/or an anti-fungal agent as well as a zinc sensor. Moreover, the present invention relates to a pharmaceutical composition comprising said compound and methods for treating bacterial or fungal infections in mammals

BACKGROUND OF THE INVENTION

The emergence of antibiotic resistances currently pose a major threat to public health. In particular, many antibiotics cannot be further used for treating bacterial and/or fungal infections and resistances dramatically spread in the last years. There exists only a limited number of antibiotic classes to which most of the antibiotics belong and there further only exists a limited number of molecular targets. These factors fortify the development and spreading of resistances against multiple antibiotics.

One example of a bacterium of which multi-drug resistant strains exist is *Pseudomonas aeruginosa*. *P. aeruginosa* is an important gram-negative pathogen causing many severe and life-threatening infections such as sepsis, endocarditis, meningitis, and chronic respiratory infections in cystic fibrosis patients. The increasing emergence of multi-drug resistant strains of *P. aeruginosa* poses major threats to public health and is one of the leading causes of hospital-acquired infections. The pathogenicity of *P. aeruginosa* is mediated by its virulence factors including the enzyme elastase that causes tissue damage and degradation of host immune proteins during infection.

The *Pseudomonas* quinolone signals (PQS) and its precursor HHQ play important roles in the Quorum Sensing and virulence factor production of the pathogen *P. aeruginosa*. Many related quinolones are known as potent antibiotics and some of the medically most important are nalidixic acid, norfloxacin, and ciprofloxacin. However, HHQ and PQS do not possess antibiotic activity and thus cannot be used as counter-measures against multi-drug resistant strains of for example *P. aeruginosa* and *S. aureus* (MRSA), which also represent a leading cause of hospital-acquired infections.

Among commercially available antibiotics only three out of ten are within a factor of two active against three tested multiresistant *S. aureus* (MRSA) strains (USA 300, Mu50 and DSM18827) when compared to the *S. aureus* strain NCTC 8325. All other antibiotics, including important drugs like erythromycin (NCTC 8325: <2 µM; USA 300: 500 µM to 1 mM; Mu50: >1 mM; DSM18827: >1 mM) and clindamycin (NCTC 8325: <2 µM; USA 300: >1 mM; Mu50: 500 µM to 1 mM; DSM18827: >1 mM) require more than 10 fold higher concentrations to inhibit growth of MRSA strains and in some cases even 100-1000 fold higher concentrations. Thus, there still remains a high need for antibiotic compounds with new chemical structures for which substantially no resistances exist and which are preferably also effective against multi-resistant strains.

SUMMARY OF THE INVENTION

Thus, the technical problem underlying the present invention is to provide a compound, which can be used as an anti-bacterial and/or an anti-fungal agent, preferably an agent being effective against multiresistant strains, as well as a corresponding pharmaceutical composition and corresponding methods for treating bacterial or fungal infections in mammals.

The solution to the above technical problem is achieved by the embodiments characterized in the claims.

Figure 1:
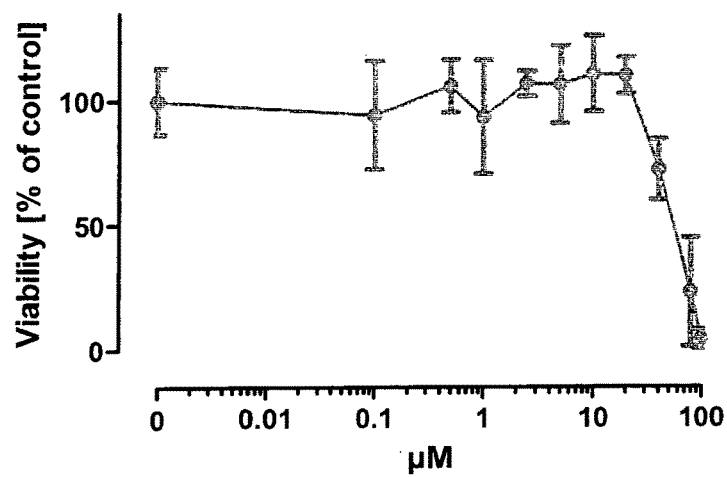
FIG. 1: Toxicological testing of compound 3 from 0-100 µM with human embryonic kidney cell line HEK-293. Viability measured by resazurin reduction after 24 h.

The present invention will be further illustrated in the following examples without being limited thereto.

DETAILED DESCRIPTION OF THE INVENTION

In particular, the present invention relates to a compound represented by the general Formula (1) or a pharmaceutically acceptable salt thereof

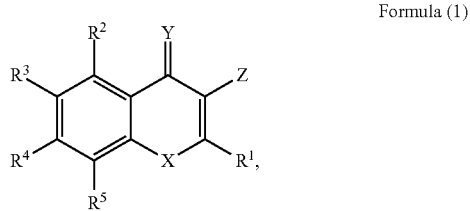

Formula (1)

wherein $R^1$ is selected from the group consisting of a substituted or unsubstituted alkyl group having from 4 to 11 carbon atoms, a substituted or unsubstituted cycloalkyl group having from 4 to 12 carbon atoms, a substituted or unsubstituted alkenyl group having from 4 to 11 carbon atoms, a substituted or unsubstituted cycloalkenyl group having from 4 to 12 carbon atoms, a substituted or unsubstituted alkynyl group having from 4 to 11 carbon atoms, a substituted or unsubstituted aryl group, and a substituted or unsubstituted heteroaryl group, X is selected from the group consisting of O, S, Se, Te, and $NR^6$ and Y is selected from the group consisting of O, S, and NR' with the proviso that Y is not O when X is O or $NR^6$, wherein $R^6$ and $R^7$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, and —OA, wherein A is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, Z is selected from the group consisting of H, $OR^8$, and $SR^9$, wherein $R^8$ and $R^9$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, $R^2$ to $R^5$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, a trifluoromethyl group, $—NE^1E^2$, $—NO_2$, —CN, $—OE^3$, $—C(O)E^4$, $—C(O)NE^5E^6$, $—COOE^7$, and $—SO_3E^8$, wherein $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group.

If not stated otherwise, such as for example the residue $R^1$, the following definitions apply to the terms "halogen", "alkyl group", "cycloalkyl group", "alkenyl group", "cycloalkenyl group", "alkynyl group", "aryl group", and "heteroaryl group". Herein the term "halogen" refers particularly to fluorine atoms, chlorine atoms, bromine atoms, and iodine atoms, preferably fluorine atoms and chlorine atoms, most preferably fluorine atoms. The term "alkyl group" refers particularly to a branched or linear alkyl group having 1 to 20, preferably 1 to 12, more preferably 1 to 6, and most preferably 1 to 4 carbon atoms, which can be substituted or unsubstituted. Examples of alkyl groups represent methyl groups, ethyl groups, propyl groups, isopropyl groups, butyl groups, isobutyl groups, tert-butyl groups, pentyl groups, hexyl groups, and heptyl groups. The term "cycloalkyl group" refers particularly to a cycloalkyl group having 3 to 10, preferably 4 to 8, more preferably 5 or 6, and most preferably 6 carbon atoms, which can be substituted or unsubstituted. Examples of cycloalkyl groups represent cyclobutyl groups, cyclopentyl groups, and cyclohexyl groups. The term "alkenyl group" refers particularly to a branched or linear alkenyl group having 2 to 20, preferably 2 to 12, more preferably 2 to 6, and most preferably 2 to 4 carbon atoms, which can be substituted or unsubstituted. Examples of alkenyl groups represent vinyl groups, allyl groups, 1-heptenyl groups, 2,6-dimethylhept-5-enyl groups, and crotyl groups, The term "cycloalkenyl group" refers particularly to a cycloalkenyl group having 4 to 10, preferably 5 to 8, more preferably 5 or 6, and most preferably 6 carbon atoms, which can be substituted or unsubstituted. Examples of cycloalkenyl groups represent cyclopentenyl groups, cyclopentadienyl groups, cyclohexyl groups, and cyclohexadienyl groups. The term "alkynyl group" refers particularly to a branched or linear alkynyl group having 2 to 20, preferably 2 to 12, more preferably 2 to 6, and most preferably 2 to 4 carbon atoms, which can be substituted or unsubstituted. Examples of alkynyl groups represent ethynyl groups, 1-propynyl groups, and propargyl groups. The term "aryl group" refers particularly to an aryl group consisting of 1 to 6, preferably 1 to 4, more preferably 1 to 3 rings, and most preferably 1 ring, which can be substituted or unsubstituted. Examples of aryl groups represent phenyl groups, anthracenyl or naphthyl groups. The term "heteroaryl group" refers particularly to a heteroaryl group consisting of 1 to 6, preferably 1 to 4, more preferably 1 to 3 rings, which can be substituted or unsubstituted. Heteroatoms, which are present in heteroaryl groups are for example N, O and S. Examples of heteroaryl groups represent pyridyl groups, pyrimidinyl groups, thienyl groups, furyl groups or pyrrolyl groups.

According to the present invention, the alkyl groups, the cycloalkyl groups, the alkenyl groups, the cycloalkenyl groups, the alkynyl groups, the aryl groups and the heteroaryl groups may be substituted or unsubstituted. The potential substituents are not specifically limited. Accordingly, instead of hydrogen atoms any substituent known in the prior art can be bonded to the further positions of the corresponding groups. For example, the potential substituents may be selected from the group consisting of a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a heteroaryl group having 1 to 3 rings, a halogen atom, —$NL^1L^2$, —$NO_2$, —$CN$, —$OL^3$, —$C(O)L^4$, —$C(O)NL^5L^6$, —$COOL^1$, and —$SO_3L^8$, wherein $L^1$ to $L^8$ are each independently selected from a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a heteroaryl group having 1 to 3 rings. Accordingly, examples of substituted alkyl groups are aralkyl groups or alkyl groups substituted with e.g. cycloalkenyl groups or any other of the above-mentioned substituents. The term "aralkyl group" refers particularly to an alkyl group wherein one or more hydrogen atoms, preferably terminal hydrogen atoms of the alkyl chain, are replaced by aryl or heteroaryl groups. Examples of aralkyl groups represent benzyl groups, 1- or 2-phenylethyl groups, and 2-(5-methylfuran-2-yl)propyl groups. Preferably, the potential substituents are selected from the group consisting of a branched or linear alkyl group having 1 to 6 carbon atoms, a branched or linear alkenyl group having 2 to 6 carbon atoms, a branched or linear alkynyl group having 2 to 6 carbon atoms, an aryl group having 1 to 3 rings, a heteroaryl group having 1 to 3 rings, —$NH_2$, —$NHCH_3$, —$N(CH_3)_2$, —$NO_2$, —$OH$, —$OCH_3$, —$OEt$, —$C(O)H$, and —$COOH$. Moreover, one or more tetravalent carbon atoms (together with the hydrogen atoms bonded thereto), when present, in each of the alkyl groups, the cycloalkyl groups, the alkenyl groups, the cycloalkenyl groups, and the alkynyl groups may each independently be substituted by a member selected from the group consisting of O, $(OCH_2CH_2)_nO$, S, $(SCH_2CH_2)_mS$, $C(O)$, $C(O)O$, $NR^{10}$, and $C(O)NR^{11}$, preferably O, $(OCH_2CH_2)_nO$, $C(O)O$, and $C(O)NR^{11}$, wherein n and m are each independently an integer from 1 to 6. Accordingly, for example an alkyl group may be interrupted by e.g. one or more PEG linkers and/or amide bonds. The way the groups are introduced instead of a carbon atom is not specifically limited. For example, a carbon atom may be substituted by $C(O)O$ in the sense of —$C(O)O$— or —$OC(O)$— and by $C(O)NR^{11}$ in the sense of —$C(O)NR^{11}$— or —$NR^{11}C(O)$—. According to the present invention, $R^{10}$ and $R^{11}$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a heteroaryl group having 1 to 3 rings, —$OG^1$, —$C(O)G^2$, —$C(O)NG^3G^4$, —$COOG^5$, and —$SO_2G^6$. In a preferred embodiment, $R^{10}$ and $R^{11}$ are each independently selected from the group consisting of a hydrogen atom, a branched or linear alkyl group having 1 to 6 carbon atoms, an aryl group having 1 to 3 rings, —$C(O)G^2$, and —$SO_2G^6$. Most preferably, $R^{10}$ and $R^{11}$ are each independently selected from the group consisting of a hydrogen atom and a branched or linear alkyl group having 1 to 6 carbon atoms. According to the present invention, $G^1$ to $G^6$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a heteroaryl group having 1 to 3 rings. In a preferred embodiment, $G^1$ to $G^6$ are each independently selected from the group consisting of a hydrogen atom, a branched or linear alkyl group having 1 to 6 carbon atoms, an aryl group having 1 to 3 rings.

Most preferably, the alkyl groups, the cycloalkyl groups, the alkenyl groups, the cycloalkenyl groups, the alkynyl groups, the aryl groups and the heteroaryl groups are unsubstituted. Moreover, in a preferred embodiment the alkyl groups, the cycloalkyl groups, the alkenyl groups, the cycloalkenyl groups, the alkynyl groups, the aryl groups and the heteroaryl groups are linear.

The compound according to the present invention may be the compound represented by the general Formula (1) as described above or a pharmaceutically acceptable salt thereof. In case the compound of the present invention is a pharmaceutically acceptable salt of the compound according to general Formula (1), the salt can be formed with inorganic or organic acids or bases. Examples of pharmaceutically acceptable salts comprise, without limitation, non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfonate derived from p-toluenesulfonic acid, sodium salts, potassium salts, magnesium salts, calcium salts, iron salts, zinc salts, aluminum salts, ammonium salts, and others. Such salts can be readily produced by methods known to a person skilled in the art.

Other salts like oxalate derived from oxalic acid, which is not considered as pharmaceutically acceptable, can be appropriately used as intermediates for the production of the compound of the general Formula (1) or a pharmaceutically acceptable salt thereof or physiologically functional derivative or a stereoisomer thereof.

According to the present invention, $R^1$ is selected from the group consisting of a substituted or unsubstituted, branched or linear alkyl group having from 4 to 11, preferably 4 to 9, more preferably 6 to 8, most preferably 7 carbon atoms, a substituted or unsubstituted cycloalkyl group having from 4 to 12, preferably 6 to 9, most preferably 7 or 8 carbon atoms, a substituted or unsubstituted, branched or linear alkenyl group having from 4 to 11, preferably 4 to 9, more preferably 6 to 8, most preferably 7 carbon atoms, a substituted or unsubstituted cycloalkenyl group having from 4 to 12, preferably 6 to 9, most preferably 7 or 8 carbon atoms, a substituted or unsubstituted, branched or linear alkynyl group having from 4 to 11, preferably 4 to 9, more preferably 6 to 8, most preferably 7 carbon atoms, a substituted or unsubstituted aryl group, and a substituted or unsubstituted heteroaryl group. In a preferred embodiment, $R^1$ is selected from the group consisting of substituted or unsubstituted, branched or linear alkyl group having from 4 to 11, preferably 4 to 9, more preferably 6 to 8, most preferably 7 carbon atoms, a substituted or unsubstituted, branched or linear alkenyl group having from 4 to 11, preferably 4 to 9, more preferably 6 to 8, most preferably 7 carbon atoms, and a substituted or unsubstituted, branched or linear alkynyl group having from 4 to 11, preferably 4 to 9, more preferably 6 to 8, most preferably 7 carbon atoms. More preferably, $R^1$ is a substituted or unsubstituted, branched or linear alkyl group having 4 to 9, even more preferably 7 carbon atoms. More preferably $R^1$ is a butyl, pentyl, hexyl, or heptyl group. Most preferably $R^1$ is a butyl or heptyl group.

According to the present invention, X is selected from the group consisting of O, S, Se, Te, and $NR^6$ and Y is selected from the group consisting of O, S, and NR' with the proviso that Y is not O when X is O or $NR^6$. $R^6$ and $R^7$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, and —OA. Moreover, A is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably A is selected from the group consisting of a hydrogen atom, a substituted or unsubstituted alkyl group, and a substituted or unsubstituted aryl group. Most preferably, A is hydrogen. Preferably, $R^6$ and $R^7$ are each independently selected from the group consisting of a hydrogen atom, a substituted or unsubstituted alkyl group, a substituted or unsubstituted aryl group, and —OA. More preferably, $R^6$ is a hydrogen atom or a substituted or unsubstituted alkyl group, most preferably a hydrogen atom. In a preferred embodiment, $R^7$ is OA, most preferably OH.

According to the present invention, Z is selected from the group consisting of H, $OR^8$, and $SR^9$, preferably H and $OR^8$, wherein $R^8$ and $R^9$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group. In a preferred embodiment, $R^8$ and $R^9$ are each independently selected from the group consisting of a hydrogen atom, a substituted or unsubstituted alkyl group, and a substituted or unsubstituted aryl group. More preferably, $R^8$ and $R^9$ are each independently selected from the group consisting of a hydrogen atom and a substituted or unsubstituted alkyl group. Most preferably, each of $R^8$ and $R^9$ is hydrogen.

According to the present invention, $R^2$ to $R^5$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a substituted or unsubstituted heteroaryl group, a halogen atom, a trifluoromethyl group, $-NE^1E^2$, $-NO_2$, $-CN$, $-OE^3$, $-C(O)E^4$, $-C(O)NE^5E^6$, $-COOE^7$, and $-SO_3E^8$. $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, and a substituted or unsubstituted heteroaryl group, preferably $E^1$ to $E^8$ are each independently selected from the group consisting of a hydrogen atom, a substituted or unsubstituted alkyl group, and a substituted or unsubstituted aryl group, most preferably $E^1$ to $E^8$ are each independently selected from the group consisting of a hydrogen atom and a substituted or unsubstituted alkyl group. Preferably, $R^2$ to $R^5$ are each independently selected from the group consisting of a hydrogen atom, a substituted or unsubstituted alkyl group, a substituted or unsubstituted aryl group, a halogen atom, a trifluoromethyl group, $-NE^1E^2$, $-NO_2$, $-OE^3$, $-C(O)E^4$, and $-COOE^7$. More preferably, $R^2$ to $R^5$ are each independently selected from the group consisting of a hydrogen atom, a methyl group, an ethyl group (-Et), a halogen atom, a trifluoromethyl group, $-NH_2$, $-NHCH_3$, $-N(CH_3)_2$, $-NO_2$, $-OH$, $-OCH_3$, $-OEt$, $-C(O)H$, and $-COOH$. Most preferably, each of $R^2$ to $R^5$ is hydrogen.

In one preferred embodiment of the present invention, X is S, Y is O, and Z is OH. In this embodiment, it is particularly preferred that $R^1$ is a substituted or unsubstituted, branched or linear alkyl group having from 4 to 11 carbon atoms, more preferably 4 to 7 carbon atoms, most preferably 7 carbon atoms. Moreover, it is preferred in this embodiment that $R^2$ to $R^5$ are each independently selected from the group consisting of a hydrogen atom, a halogen atom, and a trifluoromethyl group, more preferably each of $R^2$ to $R^5$ is independently either a hydrogen atom or a fluorine atom. In this embodiment, as examples, the present invention more preferably relates to a compound selected from the group consisting of the compounds represented by the Formulas (2) to (4) and (12) to (16), more preferably to the compounds represented by the Formulas (2) to (4), and most preferably to the compound represented by the Formula (3), or a pharmaceutically acceptable salt thereof.

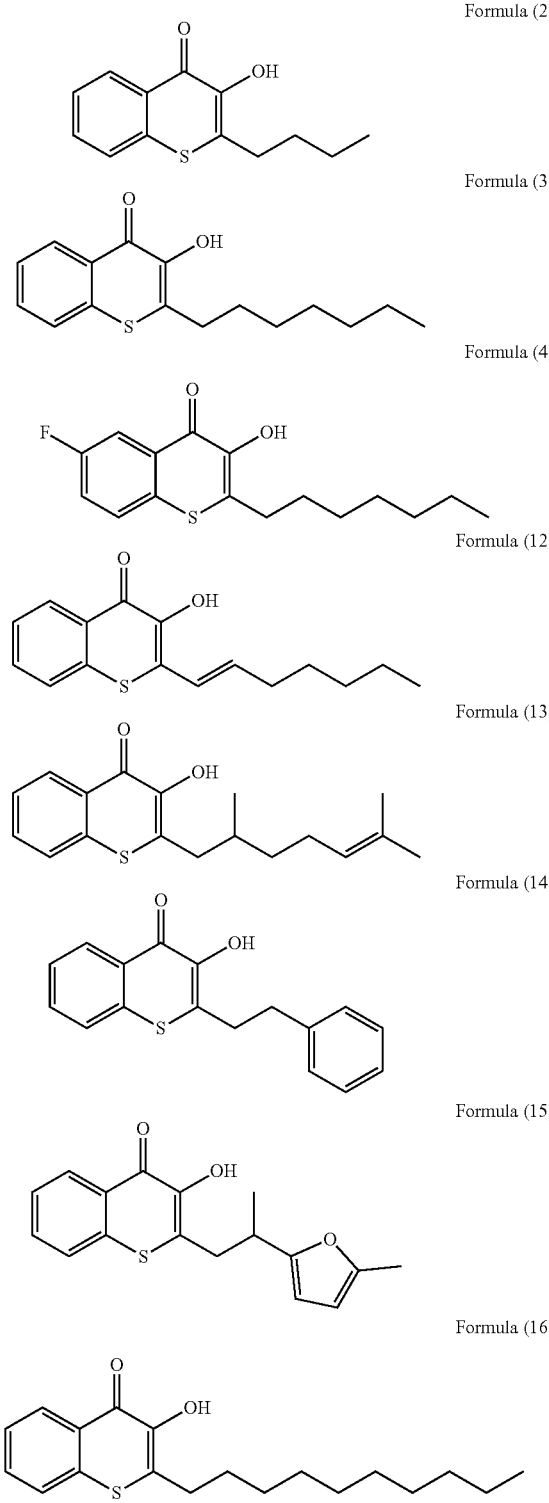

Formula (2)
Formula (3)
Formula (4)
Formula (12)
Formula (13)
Formula (14)
Formula (15)
Formula (16)

In another preferred embodiment of the present invention, X is NH, Y is N—OH or S, and Z is a hydrogen atom or OH, more preferably X is NH, Y is N—OH, and Z is a hydrogen atom or OH, and X is NH, Y is S, and Z is OH, and most preferably X is NH, Y is N—OH, and Z is a hydrogen atom. In this embodiment, it is particularly preferred that $R^1$ is a substituted or unsubstituted, branched or linear alkyl group having from 4 to 7 carbon atoms, more preferably 7 carbon atoms. Moreover, it is preferred in this embodiment that $R^2$ to $R^5$ are each independently selected from the group consisting of a hydrogen atom, a halogen atom, and a trifluoromethyl group, more preferably each of $R^2$ to $R^5$ is independently either a hydrogen atom or a fluorine atom, most preferably each of $R^2$ to $R^5$ is a hydrogen atom. In this embodiment, as examples, the present invention more preferably relates to a compound selected from the group consisting of the compounds represented by the Formulas (5) to (7), most preferably to the compound represented by the Formula (6), or a pharmaceutically acceptable salt thereof.

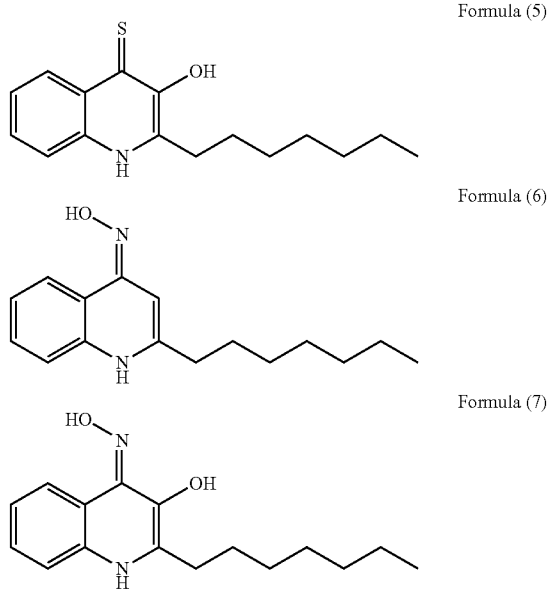

Formula (5)
Formula (6)
Formula (7)

In another preferred embodiment of the present invention, X is Te, Y is O, and Z is a hydrogen atom. In this embodiment, it is particularly preferred that $R^1$ is a substituted or unsubstituted, branched or linear alkyl group having from 4 to 7 carbon atoms, more preferably 7 carbon atoms. Moreover, it is preferred in this embodiment that $R^2$ to $R^5$ are each independently selected from the group consisting of a hydrogen atom, a halogen atom, and a trifluoromethyl group, more preferably each of $R^2$ to $R^5$ is independently either a hydrogen atom or a fluorine atom, most preferably each of $R^2$ to $R^5$ is a hydrogen atom. In this embodiment, as an example, the present invention more preferably relates to the compound represented by the Formula (8), or a pharmaceutically acceptable salt thereof.

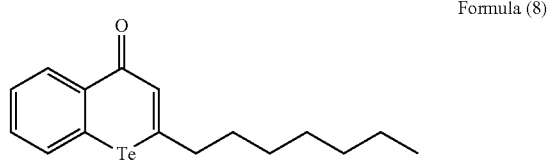

Formula (8)

The above embodiments can be combined with each other without any particular limitation. The above statements and definitions given with respect to the specific embodiments analogously apply to each respective embodiment when combined with the other embodiments. In a preferred embodiment, X is S, Y is O, and Z is OH, X is NH, Y is N—OH, and Z is a hydrogen atom or OH, and X is NH, Y is S, and Z is OH. More preferably, X is S, Y is O, and Z is OH and X is NH, Y is N—OH, and Z is a hydrogen atom. In this embodiment, as examples, the present invention more preferably relates to a compound selected from the group consisting of the compounds represented by the Formulas (2) to (4), (12) to (16), and (5) to (7), more preferably to the compounds represented by the Formulas (3) and (6), or pharmaceutically acceptable salts thereof.

In another aspect, the present invention relates to a pharmaceutical composition comprising the compound according to the present invention in a pharmaceutically active amount, and optionally a pharmaceutically acceptable carrier, excipient or diluent. The above statements and definitions analogously apply to this aspect of the present invention. The compound of the present invention can be administered per se or in the form of pharmaceutical preparations.

The term "medicament" as used herein relates to any pharmaceutical composition comprising at least the compound according to the present invention in a pharmaceutically active amount.

According to the present invention, the medicament may be administered by any administration route known in the art being suitable for delivering a medicament to a mammal. The route of administration does not exhibit particular limitations and includes for example oral application, topic application, intravenous application and intraperitoneal application. The compound also may be administered topically as ointment, by powders, drops or transdermal patch, or as an oral or nasal spray.

Preferably, the compound and the pharmaceutical composition according to the present invention are an antibacterial and/or an anti-fungal compound/composition. The bacteria and fungi which can be effectively treated by the compound and the pharmaceutical composition according to the present invention are not particularly limited. For example, gram-positive bacteria like *Bacillus subtilis, Bacillus anthracis, Bacillus cereus, Bacillus licheniformis, Bacillus thuringiensis, Bacillus larvae, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Listeria monocytogenes, Listeria welshimeri, Nocardia asteroides*, and *Rhodococcus equi*, mycobacteria like *Mycobacterium tuberculosis, Mycobacterium bovis, Mycobacterium leprae, Mycobacterium ulcerans, Mycobacterium kanasasii, Mycobacterium avium*, and *Mycobacterium paratuberculosis*, gram negative bacteria like *Acinetobacter baumannii, Enterobacter cloacae, Escherichia coli, Helicobacter pylori, Haemophilus influenzae, Klebsiella pneumoniae, Legionella pneumophila, Moraxella catarrhalis, Neisseria gonorrhoeae, Neisseria meningitidis, Pseudomonas aeruginosa, Pseudomonas putida, Proteus mirabilis, Serratia marcescens, Salmonella enteritidis*, and *Salmonella typhi*, and fungal species like *Candida albicans, Candida dubliniensis, Trichophyton rubrum*, and *Epidermophyton floccosum* can be effectively treated with the compound and the pharmaceutical composition according to the present invention. Preferably, gram-positive and gram-negative strains, preferably of *S. aureus, M. catarrhalis*, and *N. meningitidis* are effectively treated with the compound and the pharmaceutical composition according to the present invention. More preferably, gram-positive strains, preferably of *S. aureus*, are effectively treated with the compound and the pharmaceutical composition according to the present invention. Moreover, pathogenic bacteria and/or pathogenic fungi strains are preferably effectively treated with the compound and the pharmaceutical composition according to the present invention.

Preferably, the compound and the pharmaceutical composition according to the present invention are effective against multiresistant strains. More preferably, the compound and the pharmaceutical composition according to the present invention are effective against multiresistant *S. aureus* (MRSA) strains. Examples of multiresistant *S. aureus* (MRSA) strains represent, but are not limited to, USA 300, Mu50, and DSM11827.

In a preferred embodiment, the compound of the present invention has an upper limit of a minimum inhibitory concentration (MIC) against bacteria and fungi, preferably bacteria, more preferably *S. aureus*, even more preferably MRSA strains, of 200 µg/mL, more preferably 100 µg/mL, more preferably 80 µg/mL, more preferably 60 µg/mL, more preferably 40 µg/mL, more preferably 30 µg/mL, more preferably 25 µg/mL, more preferably 20 µg/mL, most preferably 15 µg/mL. The lower limit of the minimum inhibitory concentration (MIC) may only be limited by detection limits and may for example be 0.1 µg/mL.

The concentration of the compound of the present invention in the pharmaceutical composition of the present invention is not particularly limited. Preferably, the concentration of the compound of the present invention in the pharmaceutical composition is from 0.001 to 5 M, more preferably from 0.01 to 5 M, and most preferably from 0.1 to 2 M.

The compound and the composition of the present invention can be administered to animals, preferably to mammals, and particularly preferred to humans, cats, dogs, horses, poultry, cattle, and/or pigs. Most preferably, the subject is human.

The dosage of the compound of the present application can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 µg/kg/day to 100 mg/kg/day animal body weight preferably 0.1 to 50 mg/kg/day. Suitable dosage rates for larger mammals, for example humans, are of the order of from about 10 mg to 4 g/day, conveniently administered once, in divided doses such as e.g. 2 to 4 times a day, or in sustained release form.

In another aspect, the present invention relates to the compound according to the present invention or the pharmaceutical composition according to the present invention for use in treating bacterial or fungal infections in mammals. The above statements and definitions analogously apply to this aspect of the present invention.

In another aspect, the present invention relates to a disinfecting method comprising applying/using the compound according to the present invention or the pharmaceutical composition according to the present invention to a substrate e.g. selected from the group consisting of medical tools, medical equipment, floor, linen, paper, medical and industrial surfaces. The above statements and definitions analogously apply to this aspect of the present invention.

In another aspect, the present invention relates to the compound according to the present invention or the pharmaceutical composition according to the present invention for use in inhibiting elastase of *P. aeruginosa* (LasB). The above statements and definitions analogously apply to this aspect of the present invention. The compound or the pharmaceutical composition according to the present invention can be used for inhibiting elastase of *P. aeruginosa* (LasB) in vivo and in vitro.

In a preferred embodiment of this aspect of the present invention, the compound of the present invention is characterized in that X is O, S, or NR$^6$, Y is S, and Z is OH, more preferably X is NH, Y is S, and Z is OH. In this embodiment, it is particularly preferred that R$^1$ is a substituted or unsubstituted, branched or linear alkyl group having from 4 to 7 carbon atoms, more preferably 7 carbon atoms. Moreover, it is preferred in this embodiment that R$^2$ to R$^5$ are each independently selected from the group consisting of a hydrogen atom, a halogen atom, a methyl group, an ethyl group, a propyl group, a methoxy group, an ethoxy group, and a trifluoromethyl group, more preferably each of R$^2$ to R$^5$ is independently either a hydrogen atom or a fluorine atom, most preferably each of R$^2$ to R$^5$ is a hydrogen atom. In this embodiment, as examples, the compound of the present invention is selected from the group consisting of compounds represented by the Formulas (5), (9) and (10), most preferably is the compound represented by the Formula (5), or a pharmaceutically acceptable salt thereof.

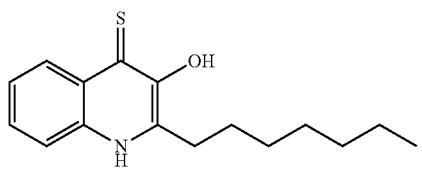

Formula (5)

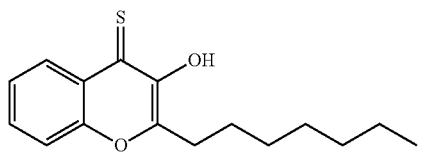

Formula (9)

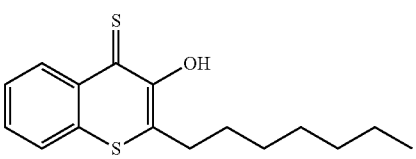

Formula (10)

While HHQ and PQS show no antibiotic activity, the compound according to the present invention is advantageously highly active against *Bacillus subtilis* and the pathogen *Staphylococcus aureus*. MIC values (cf. Tables 1 and 2) demonstrated that the compound according to the present invention is preferably even highly active against MRSA strains including community associated highly resistant USA300 strain. In contrast to most commercial antibiotics the required concentrations do advantageously not change between antibiotic-sensitive and antibiotic-resistant strains. In fact, the observed MIC values (cf. Tables 1 and 2) are better than many other known antibiotics; e.g. MICs for *S. aureus* Mu50: ampicillin (37 μg/mL), ciprofloxacin (66 μg/mL), tetracycline (29 μg/mL). Importantly, the compound according to the present invention constitutes new, yet undescribed classes of antibiotics, based e.g. on the scaffolds of thiochromen-4-one, quinolin-4-one oxime, and 3-hydroxyquinoline-4-thione. Furthermore, the compound according to the present invention advantageously exhibits no cell toxicity to kidney cells and adverse effects on even the most sensitive neuron cells were at least a factor of two to five below the MIC values that inhibit bacterial growth.

Figure 7:
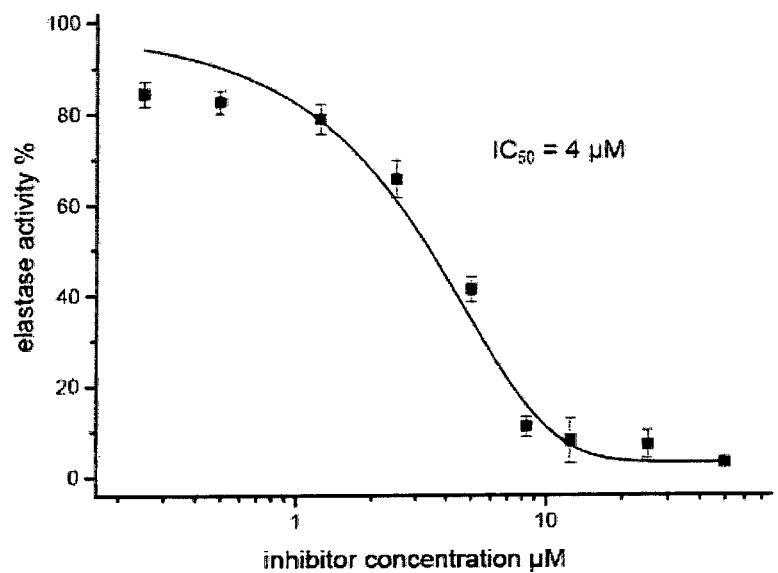
FIG. 7: In vitro inhibition of elastase (LasB) by Compound 6.
Figure 8:
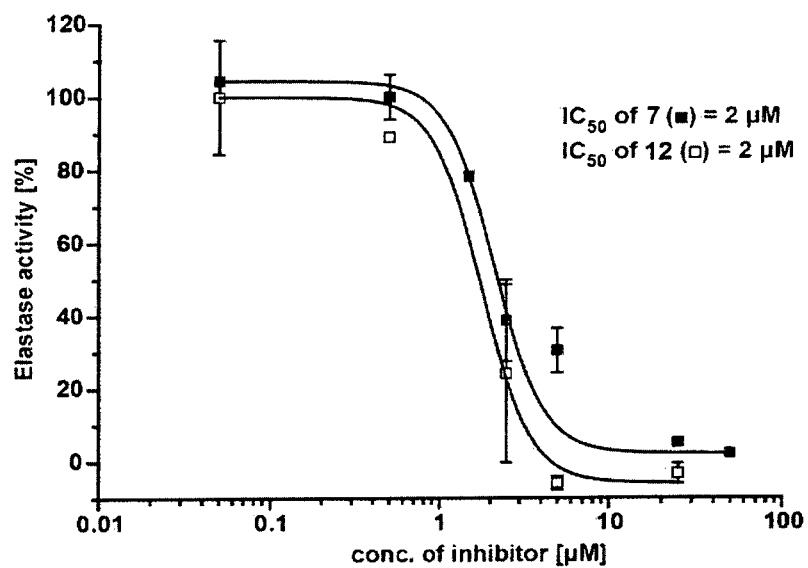
FIG. 8: In vitro inhibition of elastase (LasB) by Compounds 7 and 12.

Moreover, an in vitro assay with purified elastase and a fluorogenic substrate with the compound according to the present invention demonstrate that the enzyme elastase (LasB) is advantageously directly inhibited by the compound according to the present invention (cf. FIGS. 7 and 8). The compound binds directly to the active site zinc of the enzyme and advantageously inhibits elastolytic activity in vitro and also in cultures of life cells. The compound according to the present invention can thus for example be used as biochemical tool and for applications in medicinal chemistry.

In another aspect, the present invention relates to a method, preferably a diagnostic method, of detecting zinc comprising applying a compound represented by the general Formula (11) or a pharmaceutically acceptable salt thereof

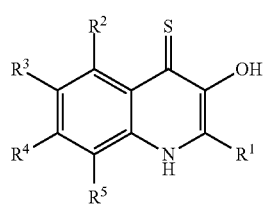

Formula (11)

to a test sample comprising or not comprising zinc and performing fluorescence spectroscopy. If not stated otherwise, the above statements and definitions analogously apply to this aspect of the present invention.

According to this aspect of the present invention, R$^1$ is selected from the group consisting of a hydrogen atom, a substituted or unsubstituted, branched or linear alkyl group having from 1 to 18, preferably 1 to 9, more preferably 1 to 8, most preferably 7 carbon atoms, a substituted or unsubstituted cycloalkyl group having from 4 to 12, preferably 6 to 9, most preferably 7 or 8 carbon atoms, a substituted or unsubstituted, branched or linear alkenyl group having from 2 to 18, preferably 2 to 9, more preferably 2 to 8, most preferably 7 carbon atoms, a substituted or unsubstituted cycloalkenyl group having from 4 to 12, preferably 6 to 9, most preferably 7 or 8 carbon atoms, a substituted or unsubstituted, branched or linear alkynyl group having from 2 to 18, preferably 2 to 9, more preferably 2 to 8, most preferably 7 carbon atoms, a substituted or unsubstituted aryl group, and a substituted or unsubstituted heteroaryl group. In a preferred embodiment, R$^1$ is selected from the group consisting of a hydrogen atom, a substituted or unsubstituted, branched or linear alkyl group having from 1 to 18, preferably 1 to 9, more preferably 1 to 8, most preferably 7 carbon atoms, a substituted or unsubstituted, branched or linear alkenyl group having from 2 to 18, preferably 2 to 9, more preferably 2 to 8, most preferably 7 carbon atoms, and a substituted or unsubstituted, branched or linear alkynyl group having from 2 to 18, preferably 2 to 9, more preferably 2 to 8, most preferably 7 carbon atoms. More preferably, R$^1$ is a substituted or unsubstituted, branched or linear alkyl group having 1 to 9, even more preferably 7 carbon atoms. Most, preferably R$^1$ is a heptyl group. According to the present invention, R$^1$ may be used to bind the compound to a solid support. Means for binding the compound via R$^1$ to a solid support are known in the art, e.g. by introducing appropriate substituents in R$^1$. Appropriate substituents may be for example alkyne or azide groups for click chemistry, and amine or carboxylate groups for amide bond formation. $R^1$ to $R^5$ may be substituted or unsubstituted as defined above. $R^2$ to $R^5$ are defined as above and may be selected to change the fluorescence properties by introducing electron withdrawing and groups or providing functional groups such as COOH, $NO_2$, C(O)alkyl, a halogen atom, OH, $NH_2$, dialkylamino, or conjugated alkenyl, aryl, and heteroaryl groups.

In a preferred embodiment, the compound of this aspect of the present invention is selected from the group consisting of the compounds represented by the Formulas (5) and (17), most preferably the compound of this aspect of the present invention is the compound represented by the Formula (5), or a pharmaceutically acceptable salt thereof.

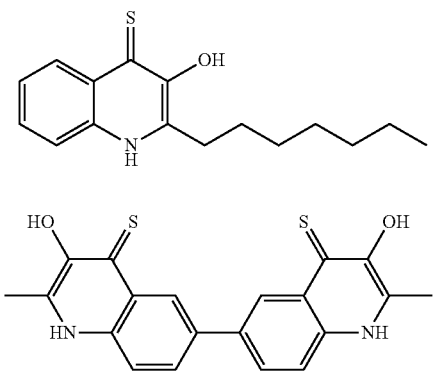

Formula (5)

Formula (17)

Preferably, zinc is in ionic form such as in the form of Zn(II).

By the method of detecting zinc according to the present invention, zinc concentrations in a test sample can be quantified by means of fluorescence spectroscopy. Means for performing fluorescence spectroscopy are not particularly limited and are known in the art. For example, standard fluorescence spectroscopy methods can be used in combination with a control sample with a given zinc concentration as a reference.

The field wherein the method of detecting zinc is used is not particularly limited. For example, the method of detecting zinc can be used in diagnostic methods practiced on the human or animal body, such as e.g. cancer diagnosis, for detecting the zinc concentration in e.g. blood, urine, (waste) water samples, and in neuroscience for studying e.g. synaptic zinc transport and signaling. Moreover, the method of the present invention can preferably be used for cancer diagnosis, for quantifying zinc levels by e.g. so-called "lab-on-a-chip" approaches, or as a tool in neuroscience.

Moreover, the method of detecting zinc may be conducted intracorporeal, extracorporeal, in situ, in vitro, and in vivo.

The test sample is not particularly limited. Thus, zinc can be detected in any given sample known in the art, which may optionally be solved in a medium. For example, the compound according to this aspect of the present invention can be used for quantifying zinc concentrations of samples obtained from a mammal, e.g. blood and urine samples.

Moreover, no interfering fluorescence is preferably recorded for any physiologically relevant mono-, di-, or trivalent metal cation, such as $Na^+$, $Ca^{2+}$, $Cu^{2+}$, $Fe^{2+}$, and $Fe^{3+}$. Thus, the test sample may contain any physiologically relevant mono-, di-, or trivalent metal cation apart from zinc without falsifying the result of the zinc detection.

The excitation maxima of the compound according to this aspect of the present invention are not particularly limited. For example the excitation maxima may be from 250 to 295 nm, preferably from 265 to 285 nm, from 315 to 345 nm, preferably from 330 to 340 nm, and most preferably at least one excitation maximum is from 270 to 280 nm.

The emission maximum of the compound according to this aspect of the present invention is not particularly limited. For example the emission maximum may be from 410 to 540 nm, preferably from 425 to 490 nm, and most preferably from 440 to 470 nm.

The zinc concentration in the test sample is not particularly limited. For example, the (lower) detection limit may be 2.5 µM.

A given sample may either be directly examined as the test sample or may be solved in a medium to give the test sample. The medium is not particularly limited. For example, the medium may be an aqueous medium, a medium based on one or more organic solvents, or a medium based on a mixture of water with one or more organic solvents. Preferably, the medium is obtained from one or more selected from the group consisting of water, DMSO, ethanol, methanol, isopropanol, chloroform, DMF, dioxane, THF, acetonitrile and ethyl acetate. More preferably, the medium is obtained from one or more selected from the group consisting of DMSO and ethanol.

In case the compound according to this aspect of the present invention is exposed to zinc ions, a strong fluorescence in organic solvents like ethanol and DMSO is observed, confirming zinc binding. Detailed excitation and emission spectra measurements gave e.g. 276 nm as excitation maximum and e.g. 448 nm as emission maximum. The compound of the present invention is enormously sensitive for zinc and significant (2 fold over baseline) fluorescence is still determined at very low zinc concentrations of e.g. only 2.5 µM. The compound of the present invention is preferably a highly specific sensor compound for zinc and no interfering fluorescence is recorded for any physiologically relevant mono-, di-, or trivalent metal cation, such as $Na^+$, $Ca^+$, $Cu^{2+}$, $Fe^{2+}$, and $Fe^+$.

Measuring zinc concentrations can be important for cancer diagnosis and zinc also plays a crucial role within the central nervous system. The compound of the present invention may thus preferably be a valuable tool to quantify zinc levels by e.g. "lab on a chip" approaches or e.g. as a tool in neuroscience.

EXPERIMENTAL PROCEDURES

General

Chemicals and solvents for the synthesis were purchased from Sigma-Aldrich, Acros Organics, Carl Roth or VWR Chemicals and were used without further purification. *Pseudomonas aeruginosa* PA14 (DSM 19882) was purchased from DSMZ. Overnight cultures were prepared in LB medium (Lennox broth) at 37° C. and 200 rpm in a glass culture tube. For Silica gel chromatography, distilled technical grade solvents and silica gel 60 Å (Carl Roth) was used. Thin layer chromatography (TLC) was performed using aluminum sheets "TLC Silica gel 60 F254" from Merck Millipore® and analyzed with UV-light, permanganate solution or an iodine chamber. NMR spectra were obtained with Bruker Avance-III 400 and Bruker Avance-III 600 NMR spectrometers at ambient temperature. Multiplicities are given as follows: s—singlet, d—doublet, t—triplet, q—quartet, quint.—quintet, m—multiplet. Chemical shifts (δ) are given in parts per million (ppm) relative to the solvent residual signal with CDCl3 δH=7.26 ppm and δC=77.16 ppm, DMSO-d6 δH=2.50 ppm and δC=39.52 ppm, THF-d8 δH=1.72 and 3.58 ppm and δC=67.21 and 25.31 ppm.[1] The obtained data were processed and analyzed with MestReNova or Bruker Topspin 3.5 software. Mass spectrometry data were obtained by LCMS2020 from Shimadzu (high-pressure pump LC-20 AD, auto sampler SIL-20AT HAT, column oven CTO-20AC, UV-Vis detector SPD-20A, controller CBM-20, ESI detector, software LCMS Solution, column Nucleodur 100-3-C18ec, 125×4 mm Machery Nagel). The method used for LCMS was a gradient with a flow rate of 0.4 ml/min. Mobile phase with A=H2O+0.1% formic acid, B=acetonitrile+0.1% formic acid. Gradient over 20 min: T0: B=10%; T20: B=95%; T25: B=95%. For some smaller molecules, EI-MS JMS-Q1500GC from Joel Ltd. without coupled GC, the Head Space Auto Sampler (HS) and the analysis software Escrime was used. Absorption and fluorescence data were acquired with a TECAN Infinite® M200 PRO plate reader using the i-Control™ software and 96-well plates from Sarstedt (Microtest plates 96-well, flat-bottom, without lid) or Thermo Scientific (Microfluor® 1, 96-Well Fluorescence Microplates, flat-bottom, without lid).

(Comparative) Example 1: Synthesis of HHQ (Compound 1)

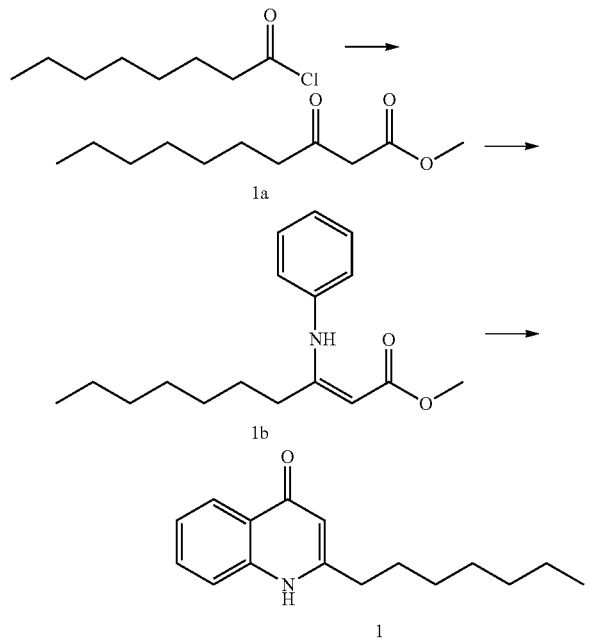

Synthesis of methyl-3-oxodecanoate (1a)

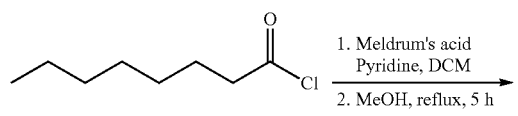

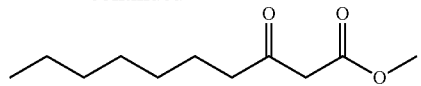

5.041 g 2,2-Dimethyl-1,3-dioxane-4,6-dione (Meldrum's acid) (34.95 mmol) was solved in DCM (50 ml) and cooled to 0° C. 5.5 ml Pyridine (68.27 mmol) was added and after 20 minute at 0° C., 6.0 ml octanoyl chloride (35.15 mmol) was added dropwise. The resulting orange solution was allowed to stir for 1 h at 0° C. and 1 h at room temperature. The reaction mixture was washed with 5% HCl (3×60 ml), distilled water (2×60 ml) and Brine (2×60 ml). The organic phase was dried over anhydrous MgSO$_4$, filtered and the solvent evaporated under reduced pressure. The remaining brown oil was solved in 100 ml MeOH and refluxed for 5 h. The solvent was evaporated and the residue was purified by column chromatography on silica gel using hexane/ethyl acetate (4:1). The product was obtained as a colorless oil (m=4.5 g, 64.2%). Rf=0.62 (hexane/ethyl acetate 4:1). $^1$H-NMR (CDCl$_3$ 400.13 MHz) δ (ppm): 0.87 (m, 3H, —CH$_3$), 1.24-1.32 (m, 8H, (CH$_2$)$_4$), 1.59 (m, 2H, —CH$_2$—CH$_2$—CO), 2.25 (t, 2H, J=7.4 Hz, —CH$_2$—CH$_2$—CO), 3.44 (s, 2H, —CH$_2$—COO), 3.73 (s, 3H, —OCH$_3$). $^{13}$C-NMR (CDCl$_3$ 100.62 MHz) δ (ppm): 14.1 (—CH$_3$), 23.5 (—CH$_2$—CH$_2$—CO), 22.6, 28.9, 29.1, 31.7, (4×-CH$_2$), 43.1 (—CH$_2$—CH$_2$—CO), 49.0 (—CH$_2$—COO), 52.4 (—OCH$_3$) 167.7 (—COO), 202.9 (—CO).

Synthesis of methyl-3-anilino-2-decanoate (1b)

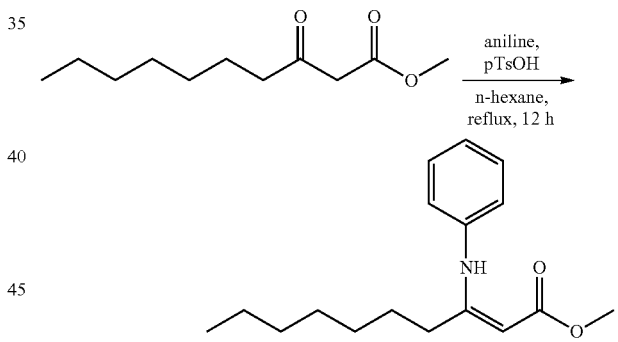

9.7 g β-ketoester 1a (48.43 mmol) was solved in n-hexane (150 ml) and 4.0 aniline (43.27 mmol) and 0.16 g p-toluene sulfonic acid (0.92 mmol) was added. The mixture was refluxed for 12 h. The reaction was allowed to cool to room temperature and the solvent was evaporated. The residue was purified by column chromatography on silica gel using n-hexane/ethyl acetate (9:1). The product was obtained as a yellow oil (m=9.26 g, 69.5%). Rf=0.66 (hexane/ethyl acetate 9:1). $^1$H-NMR (CDCl$_3$ 400.13 MHz) δ (ppm): 0.84 (m, 3H, —CH$_3$), 1.09-1.30 (m, 8H, (CH$_2$)$_4$), 1.41 (m, 2H, —CH$_2$—CH$_2$—CN), 2.29 (t, 2H, J=7.8 Hz, CH$_2$—CH$_2$—CN), 3.69 (s, 3H, —OCH$_3$), 4.74 (s, 1H, =CH—COO), 7.09 (d, 2H, J=7.6 Hz, Ar—CH), 7.18 (t, 1H, J=7.50 Hz, Ar—CH), 7.32 (m, 2H, Ar—CH), 10.3 (s, 1H, =NH). $^{13}$C-NMR (CDCl$_3$ 100.62 MHz) δ (ppm): 13.8 (—CH$_3$), 27.8 (—CH$_2$—CH$_2$—CO), 22.3, 28.6, 28.8, 31.4 (4×-CH$_2$), 32.0 (—CH$_2$—CH$_2$—CO), 50.1 (—OCH$_3$), 84.4 (=CH), 124.9 (2C), 125.0, 128.8 (2C), 139.1 (6×Ar—CH), 163.6 (≡CN), 170.8 (—COO).

19

Synthesis of 2-heptyl-4-quinolone, HHQ (Compound 1)

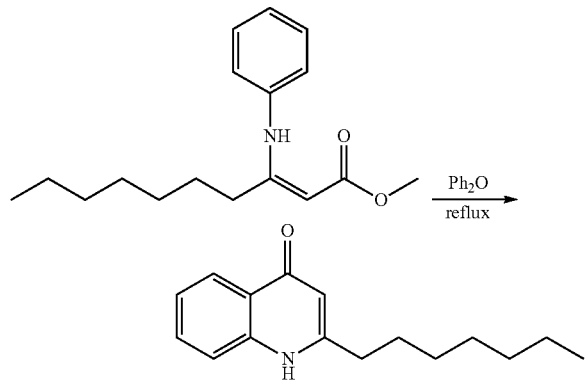

3 g methyl-3-anilino-2-decenoate 1b (10.90 mmol) was added dropwise to 15 ml diphenyl ether at reflux conditions and reflux was maintained for 6 h. The reaction mixture was allowed to cool and dropwise added to n-hexane. The precipitate was filtered and washed with n-hexane. The product was obtained as a white solid (m=2.27 g, 81%). $^1$H-NMR (CDCl$_3$ 400.13 MHz) δ (ppm): 0.82 (m, 3H, H-15), 1.14-1.25 (m, 6H, H-12-14), 1.26-1.33 (m, 2H, H-11), 1.69 (m, 2H, H-10), 2.65 (t, 2H, J=7.8 Hz, H-9), 6.21 (s, 1H, H-3), 7.32 (m, 1H, H-6), 7.57 (m, 1H, H-7), 7.64 (d, 1H, J=8.2 Hz, H-8), 8.35 (d, 1H, J=8.2 Hz, H-5), 11.14 (s, 1H, =NH). $^{13}$C-NMR (CDCl$_3$ 100.62 MHz) δ (ppm): 14.2 (C-15), 29.0 (C-10), 29.3 (C-11), 22.7, 29.1, 31.8 (C-12-14), 34.6 (C-9), 108.6 (C-3), 118.2 (C-8), 123.7 (C-6), 125.2 (C-4a), 125.7 (C-5), 131.9 (C-7), 140.5 (C-8a), 154.6 (C-2), 179.1 (C-4). ESI-MS: m/z=243.95 [M+H]+, calc. for C$_{16}$H$_{21}$NO+H$^+$=244.36. m/z=284.95 [M+H]+, calc. for C$_{16}$H$_{21}$NO+C$_2$H$_3$N+H$^+$=285.20. m/z=487.10[2M+H]+, calc. for C$_{32}$H$_{42}$N$_2$O$_2$+H$^+$=487.33.

Example 2: Synthesis of 1-Te-HHQ (Compound 2)

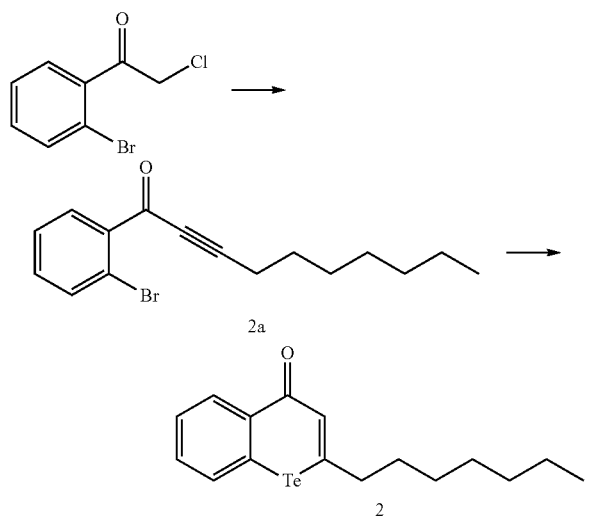

20

Synthesis of 1-(2-bromophenyl) dec-2-yn-1-one (2a)

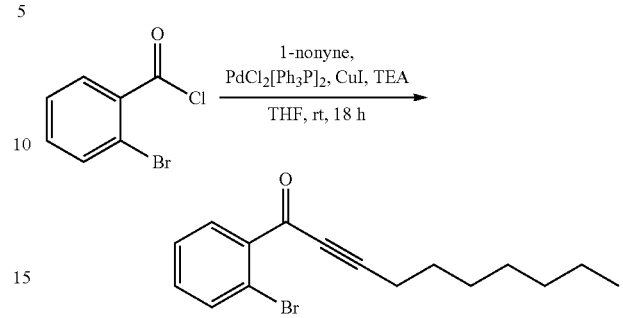

Under argon, 2.096 g (9.55 mmol) o-bromobenzoyl chloride was solved in 30 ml dry THF and 110 mg (0.157 mmol) PdCl$_2$[Ph$_3$P]$_2$ and 1.4 ml (10.06 mmol) TEA were added and stirred for 10 min at room temperature. 69 mg (0.36 mmol) CuI was added and stirred for 10 min at room temperature and 819 mg (6.6 mmol) 1-nonyne was added. After 18 h at room temperature the solvent was evaporated and the residue diluted with ethyl acetate and washed twice with water and one time with brine. The solvent was evaporated and the residue purified by column chromatography on silica gel using n-hexane/ethyl acetate (95:5). The product was obtained as yellow oil (1.756 g, 87%). Rf=0.33 (n-hexane/ethyl acetate 95:5). $^1$H-NMR (CDCl$_3$ 399.79 MHz) δ (ppm): 0.89 (m, 3H, —CH$_3$), 1.26-1.37 (m, 6H, —CH$_2$—(CH$_2$)$_3$—CH$_3$), 1.44 (m, 2H, —CH$_2$—(CH$_2$)$_3$—CH$_3$), 1.64 (m, 2H, —CH$_2$—(CH$_2$)$_4$—CH$_3$), 2.46 (dd, J=7.5 Hz, J=7.2 Hz, 2H, —CH$_2$—(CH$_2$)$_5$—CH$_3$), 7.34 (ddd, J=8.3 Hz, J=7.8 Hz, J=1.8 Hz, 1H, Ar—CH), 7.41 (ddd, J=8.3 Hz, J=7.6 Hz, J=1.2 Hz, 1H, Ar—CH), 7.66 (dd, J=7.8 Hz, J=1.2 Hz, 1H, Ar—CH), 7.99 (dd, J=7.6 Hz, J=1.8 Hz, 1H, Ar—CH). $^{13}$C-NMR (CDCl$_3$ 100.52 MHz) δ (ppm): 14.2 (—CH$_3$), 19.5 (—CH$_2$—(CH$_2$)$_5$—CH$_3$), 22.7, 28.8, 31.8 (—CH$_2$—(CH$_2$)$_3$—CH$_3$), 27.7 (—CH$_2$—(CH$_2$)$_4$—CH$_3$), 29.1 (—CH$_2$—(CH$_2$)$_3$—CH$_3$), 80.9 (—CO—C≡), 98.3 (≡C—CH$_2$—), 121.1 (=C—Br), 127.3 (Ar—CH), 132.9 (Ar—CH), 133.2 (Ar—CH), 135.0 (Ar—CH), 137.7 (≡C—CO—), 177.8 (=CO).

Synthesis of 2-heptyl-4H-tellurochromen-4-one (Compound 2)

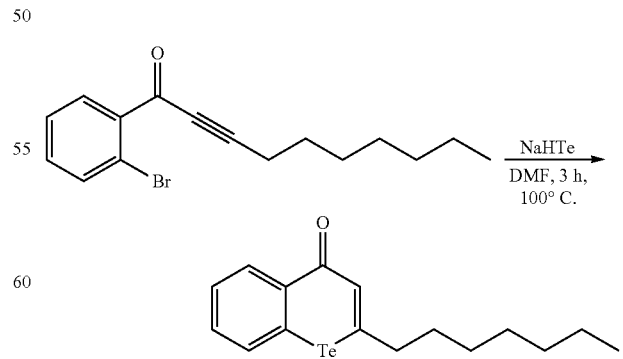

Under argon, 0.257 g (2.00 mmol) tellurium powder and 90 mg (2.38 mmol) NaBH$_4$ were dissolved in 7 ml dry DMF and heated to 100° C. for 1 h to react to NaHTe. 500 mg of 2a (1.63 mmol) were solved in 3 ml dry DMF and added to the reaction mixture. After 3 h at 100° C. the reaction was cooled to room temperature and while cooled, quenched by the addition of 10 ml water. The solvent was evaporated under reduced pressure. The residue was diluted with ethyl acetate and washed once with water and twice with brine. The organic phase was dried with MgSO$_4$, filtered and evaporated. The residue was purified by column chromatography on silica gel using n-hexane/ethyl acetate 95:5. The product was obtained as an orange oil which after a while crystallizes (240 mg, 41.3%). Rf=0.2 (n-hexane/ethyl acetate 95:5). $^1$H-NMR (CDCl$_3$ 399.79 MHz) δ (ppm): 0.88 (m, 3H, H-15), 1.22-1.44 (m, 6H, H-11-14), 1.68 (m, 2H, H-10), 2.82 (m, 2H, H-9), 7.18 (s, 1H, H-3), 7.37 (ddd, J=8.3 Hz, J=7.7 Hz, J=1.6 Hz, 1H, H-7), 7.43 (ddd, J=8.3 Hz, J=8.0 Hz, J=1.2 Hz, 1H, H-6), 7.70 (dd, J=7.7 Hz, J=1.2 Hz, 1H, H-8), 8.67 (dd, J=8.0 Hz, J=1.6 Hz, 1H, H-5). $^{13}$C-NMR (CDCl$_3$ 100.52 MHz) δ (ppm): 14.2 (C-15), 22.7, 28.9, 29.1, 31.8 (C-11-14), 31.2 (C-10), 42.5 (C-9), 123.5 (C-8a), 128.3 (C-6), 131.1 (C-3), 131.4 (C-7), 131.9 (C-5), 134.1 (C-8), 134.7 (C-4a), 150.5 (C-2), 186.2 (C-4). ESI-MS: m/z=358.70 [M+H]+, calc. for C$_{16}$H$_{21}$O$^{126}$Te$^+$=359.06. m/z=356.70 [M+H]+, calc. for C$_{16}$H$_{21}$O$^{124}$Te$^+$=357.06. m/z=354.85 [M+H]+, calc. for C$_{16}$H$_{21}$O$^{122}$Te$^+$=355.06. m/z=399.80 [M+H$_2$O+Na]$^+$, calc. for C$_{16}$H$_{22}$NaO$_2$$^{126}$Te$^+$=399.06. m/z=397.85 [M+H$_2$O+Na]$^+$, calc. for C$_{16}$H$_{22}$NaO$_2$$^{124}$Te$^+$=397.06. m/z=395.75 [M+H$_2$O+Na]$^+$, calc. for C$_{16}$H$_{22}$NaO$_2$$_{122}$Te$^+$=395.05.

Example 3: Synthesis of HHQ-Oxime (Compound 3)

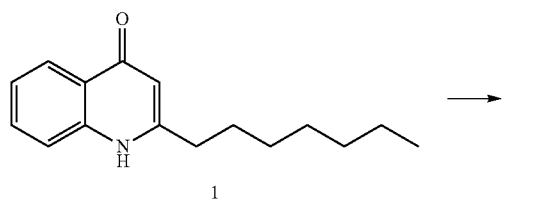

1

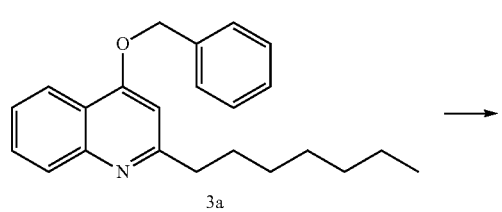

3a

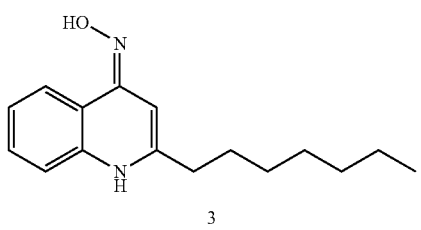

3

Synthesis of 4-(benzyloxy)-2-heptyl-1,4-dihydroquinoline (3a)

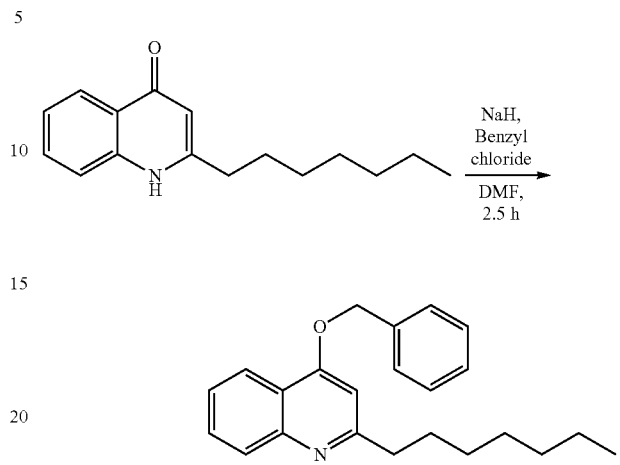

0.297 g (1.22 mmol) 2-heptylquinolin-4(1H)-one and 78 mg NaH (1.95 mmol, 60% in mineral oil) were dissolved in 6 ml dry DMF under nitrogen atmosphere and were stirred for 30 min at room temperature. 227 mg (1.8 mmol) benzyl chloride was solved in 4 ml DMF and added to the reaction dropwise. The reaction was stirred at room temperature for 2 h and quenched by the addition of 5 ml water. Water and DMF were evaporated under reduced pressure at 60° C. The residue was solved in DCM and washed twice with water and once with brine, dried with MgSO$_4$, filtered and evaporated. The residue was purified by column chromatography on silica gel using DCM/MeOH (30:1). The product was received as a colorless oil (143 mg, 35%). Rf=0.95 (DCM/MeOH (30:1). $^1$H-NMR (CDCl$_3$ 399.79 MHz) δ (ppm): 0.89 (m, 3H, H-15), 1.20-1.40 (m, 8H, H-11-14), 1.76 (m, 2H, H-10), 2.88 (m, 2H, H-9), 5.37 (s, 2H, —O—CH$_2$—Ar), 6.94 (s, 1H, H-3), 7.36 (m, 1H, Ar—CH), 7.42 (m, 2H, Ar—CH), 7.47 (ddd, J=8.7 Hz, J=8.4 Hz, J=1.0 Hz, 1H, H-6), 7.53 (m, 2H, Ar—CH), 7.69 (ddd, J=8.7 Hz, J=8.4 Hz, J=1.4 Hz, 1H, H-7), 7.90 (d, J=8.4 Hz, 1H, H-8), 8.19 (dd, J=8.4 Hz, J=1.1 Hz, 1H, H-5). $^{13}$C-NMR (CDCl$_3$ 100.53 MHz) δ (ppm): 14.4 (C-15), 23.7, 30.3, 30.5, 32.9 (C-11-14), 31.3 (C-10), 40.1 (C-9), 71.6 (C-16) 102.7 (C-3), 121.4 (C-4a), 122.9 (C-5), 126.3 (C-6), 127.9 (C-8), 128.7 (2C, Ar—CH), 129.3 (Ar—CH), 129.7 (2C, Ar—CH), 131.2 (C-7), 137.5 (Ar—C—), 149.5 (C-8a), 163.3 (C-4), 166.0 (C-2).

Synthesis of 2-heptylquinolin-4(1H)-one oxime, HHQ-Oxime (Compound 3)

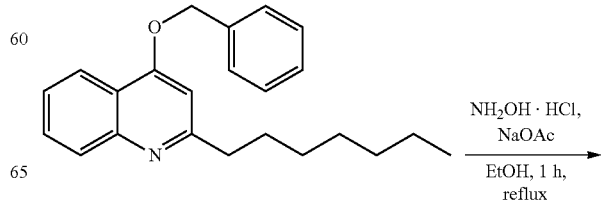

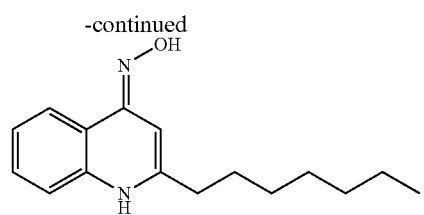

0.132 g (0.396 mmol) 4-(benzyloxy)-2-heptylquinoline was solved in 40 ml EtOH together with 1.5 g (0.02 mol) NH$_2$OH.HCl and 1.8 g (0.02 mol) sodium acetate. The reaction was stirred at reflux conditions for 1 h. After the reaction cooled to room temperature the solids were filtered off and washed with EtOH. The filtrated and washing phases were combined and evaporated under reduced pressure. The residue was solved in DCM and washed two times with water. By dewatering the organic phase with Brine, a colorless foam between the DCM and brine appeared.

The brine phase and the foam was extracted three times with DCM. The organic phases were discarded. The brine phase was basified with 1 N NaOH whereupon the foam disappeared. The brine phase was extracted two times with ethyl acetate. The combined organic phases were tried with MgSO$_4$, filtered and evaporated leaving a yellow crystalline solid which was purified by column chromatography on silica gel using DCM. The product was received as yellow crystals (50 mg, 49%). Rf=0.95 (DCM). $^1$H-NMR (DMSO-d$_6$ 600.33 MHz) δ (ppm): 0.85 (m, 3H, H-15), 1.20-1.36 (m, 8H, H-11-14), 1.59 (m, 2H, H-10), 2.33 (m, 2H, H-9), 5.92 (s, 1H, H-3), 6.98 (dd, J=8.5 Hz, J=8.1 Hz, 1H, H-6), 7.10 (d, J=8.2 Hz, 1H, H-8), 7.28 (ddd, J=8.5 Hz, J=8.2 Hz, J=1.2 Hz, 1H, H-7), 7.79 (dd, J=8.1 Hz, J=1.2 Hz, 1H, H-5), 9.54 (s, 1H, =N—OH), 9.74 (s, br, 1H, H-1). $^{13}$C-NMR (DMSO-d$_6$ 150.95 MHz) δ (ppm): 14.0 (C-15), 28.5 (C-10), 22.1, 28.0, 28.6, 31.2 (C-11-14), 33.5 (C-9), 92.4 (C-3), 116.6 (C-8), 118.7 (C-4a), 121.7 (C-6), 122.3 (C-5), 128.8 (C-7), 138.3 (C-8a), 146.0 (C-2), 147.1 (C-4).

(Comparative) Example 4: Synthesis of PQS (Compound 4)

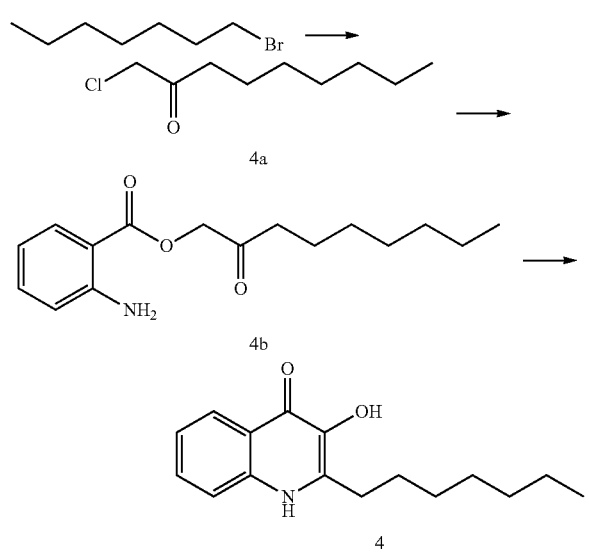

Synthesis of 1-chloro-2-nonanone (4a)

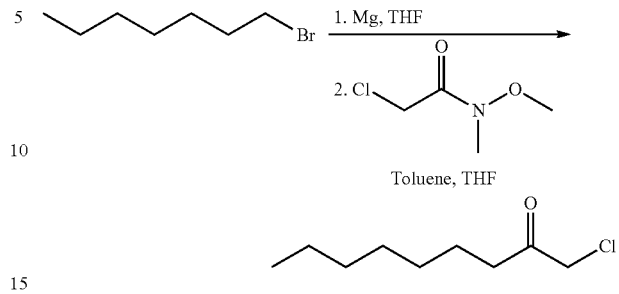

0.134 g Magnesium (5.54 mmol) and THF (5.5 ml) were stirred under an argon atmosphere. 0.87 ml 1-Bromoheptane (4.85 mmol) was added and the reaction vessel was flushed with argon. The reaction was stirred for 1 h at room temperature and afterwards added to a solution of N-methoxy-N-methylchloroacetamide (0.500 g, 3.69 mmol) in toluene (5 ml) and THF (10 ml) at 0° C. The mixture was stirred at room temperature for 1.5 h. To this solution was added cold 2M HCl (5 ml) and the layers were separated. The aqueous phase was extracted with n-hexane (3×50 ml). The combined organic layers were washed with Brine solution (3×50 ml), dried over anhydrous MgSO$_4$ and filtered. The solvent was evaporated and the product was purified by column chromatography on silica gel using hexane/ethyl acetate (9:1).

The product was obtained as a yellow oil (m=0.480 g, 74%). Rf=0.65 (hexane/ethyl acetate 9:1). $^1$H-NMR (CDCl$_3$ 400.13 MHz) δ (ppm): 0.87 (m, 3H, —CH$_3$), 1.23-1.32 (m, 8H, (—CH$_2$)$_4$), 1.61 (m, 2H, —CH$_2$—CH$_2$—CO), 2.57 (m, 2H, —CH$_2$—CH$_2$—CO), 4.06 (s, 2H, —CH$_2$—Cl). $^{13}$C-NMR (CDCl$_3$ 100.26 MHz) δ (ppm): 14.1 (—CH$_3$), 22.7, 23.7, 29.1, 29.2, 31.7, 39.8 (6×CH$_2$), 48.3 (—CH$_2$—Cl), 202.9 (=CO).

Synthesis of 2-oxononyl-2-aminobenzoate (4b)

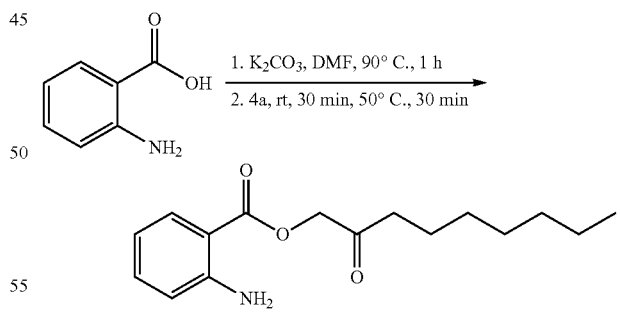

Under argon atmosphere 3.26 g (23.771 mmol) of anthranilic acid were dissolved in 44 mL dry DMF. The potassium carbonate (2.555 g, 18.489 mmol) was added as a powder and after heating to 90° C. the reaction was stirred for 1 h. During the time the solution became brown and finally murky and white. At room temperature 3.5 g (19.809 mmol) 1-chlorononan-2-one was added to the reaction and the mixture was stirred for 30 minutes at 25° C. Afterwards the temperature was raised to 50° C. and the reaction was stirred for further 30 minutes at that temperature before it was allowed to cool to room temperature. The mixture was poured on ice and the white precipitate was filtered and washed with water. The HV-dried product was obtained as a white solid (5.1546 g, 94%). $^1$H-NMR (CDCl$_3$ 400 MHz) δ (ppm): 0.88 (t, J=7.0 Hz, 3H, H-9'), 1.33-1.21 (m, 8H, H-5', H-6', H-7', H-8'), 1.64 (p, J=7.4 Hz, 2H, H-4'), 2.49 (t, J=7.4 Hz, 2H, H-3'), 4.83 (s, 2H, H-1'), 6.64-6.68 (m, 2H, H-5, H-6), 7.29 (ddd, J=1.6 Hz, 7.2 Hz, 8.7 Hz, 1H, H-4), 7.93 (dd, J=1.7 Hz, 8.4 Hz, 1H, H-3). $^{13}$C-NMR (CDCl$_3$ 100 MHz) δ (ppm): 14.2 (C-9'), 22.7 (C-4'), 23.5 (C-5'), 29.2 (C-6'), 29.3, 31.8 (C-7', C-8'), 39.1 (C-3'), 68.1 (C-1'), 110.0 (C-1), 116.5, 116.9 (C-5, C-3), 131.5 (C-6), 134.7 (C-4), 150.9 (C-2), 167.3 (ArCOO), 205.0 (C-2'). MS (ESI): m/z calculated for $C_{16}H_{23}NO_3+H^+$: 278.2 [M+H]$^+$ and $C_{32}H_{46}N_2O_6+H^+$: 555.3 [2M+H]$^+$, found: 277.9, 555.1.

Synthesis of 2-heptyl-3-hydroxy-4-quinolone, PQS (Compound 4)

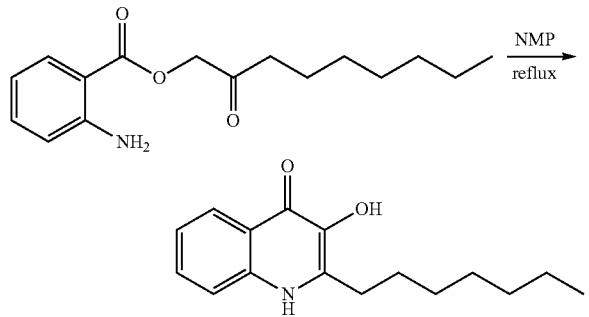

1.91 g (6.886 mmol) of 4b were dissolved in 19.2 mL NMP and heated up in a sand bath to 200° C. It was refluxed for 2 h and cooled to room temperature again. The mixture was poured on ice and the formed brown precipitate was filtered. The solid was recrystallized in ethanol and the product was obtained as light brown colored crystals (1.0873 g, 61%). $^1$H-NMR (DMSOd$_6$ 400 MHz) δ (ppm): 0.83 (t, J=6.9 Hz, 3H, H-15), 1.16-1.37 (m, 8H, H-11, H-12, H-13, H-14), 1.66 (p, J=7.3 Hz, 2H, H-10), 2.73 (t, J=7.9 Hz, 2H, H-9), 7.19-7.23 (ddd, J=2.6 Hz, 5.4 Hz, 8.1 Hz, 1H, H-6), 7.50-7.55 (m, 2H, H-7, H-8), 8.10 (d, J=8.1 Hz, 1H, H-5), 11.40 (s, 1H, N—H). $^{13}$C-NMR (DMSOd$_6$ 100 MHz) δ (ppm): 13.9 (C-15), 22.0 (C-14), 27.8 (C-10), 28.1 (C-9), 28.5 (C-11), 28.8 (C-12), 31.2 (C-13), 118.2 (C-8), 121.9 (C-6), 122.7 (C-4a), 124.9 (C-5), 130.4 (C-7), 135.5 (C-2), 137.8 (C-8a), 138.3 (C-3), 169.3 (C-4). MS (ESI): m/z calculated for $C_{16}H_{21}NO_2+H^+$: 260.2 [M+H]$^+$ and $C_{32}H_{42}N_2O_4+H^+$: 519.3 [2M+H]$^+$, found: 260.0, 519.2.

Example 5: Synthesis of 2-heptyl-3-hydroxy-4H-thiochromen-4-one, 1-S-PQS

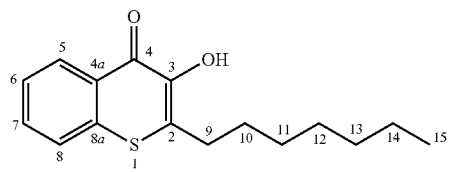

(Compound 5)

Synthesis of 2-heptylthiochroman-4-one (5a)

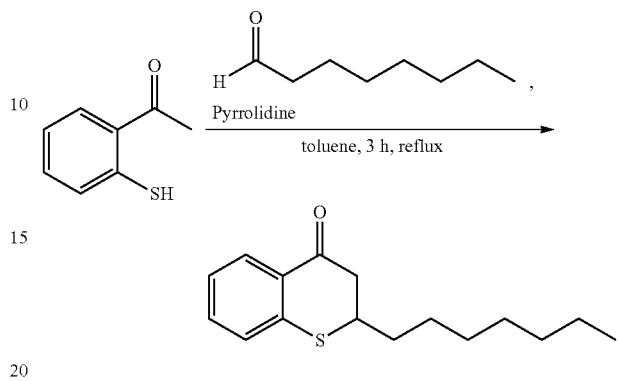

Under nitrogen atmosphere octanal (0.842 g, 6.57 mmol) was dissolved in 33.33 mL dry toluene and pyrrolidine (0.234 g, 3.285 mmol) was added. The solution becomes murky and after 10 minutes 1.00 g (6.57 mmol) of 2-thioacetophenone were added carefully. After it was stirred for 30 minutes at room temperature the solution became clear and yellow and the temperature was raised to 110° C. The reaction was refluxed for 3 h and when it was cooled to room temperature the mixture was diluted with diethyl ether, washed with saturated NaHCO$_3$ solution, water and brine. The organic solution was dried over MgSO$_4$, evaporated and the pure product was obtained over silica gel chromatography in n-hexane/ethyl acetate 9:1 as a yellow oil (0.702 g, 41%). Rf=0.51 (n-hexane/ethyl acetate 12:1). $^1$H-NMR (CDCl$_3$ 400.13 MHz) δ (ppm): 0.88 (t, J=7.1 Hz, 3H, H-15), 1.20-1.35 (m, 8H, H-11, H-12, H-13, H-14), 1.40-1.52 (m, 2H, H-10), 1.69 (d, J=7.3 Hz, 1H, H-9), 1.73 (dd, J=0.6 Hz, 7.6 Hz, 1H, H-9), 2.79 (dd, J=11.2 Hz, 16.3 Hz, 1H, H-3), 3.04 (dd, J=3.1 Hz, 16.3 Hz, 1H, H-3), 3.46-3.53 (m, 1H, H-2), 7.16 (ddd, J=1.2 Hz, 7.3 Hz, 8.1 Hz, 1H, H-6), 7.26 (dd, J=1.0 Hz, 8.0 Hz, 1H, H-8), 7.38 (ddd, J=1.6 Hz, 7.3 Hz, 8.0 Hz, 1H, H-7), 8.08 (dd, J=1.5 Hz, 8.0 Hz, 1H, H-5). $^{13}$C-NMR (CDCl$_3$ 100.53 MHz) δ (ppm): 14.2 (C-15), 22.7 (C-14), 26.8 (C-10), 29.2 (C-12), 29.3 (C-11), 31.8 (C-13), 34.7 (C-9), 41.8 (C-2), 46.4 (C-3), 125.0 (C-6), 127.8 (C-8), 129.0 (C-5), 130.8 (C-4a), 133.6 (C-7), 141.7 (C-8a), 194.8 (C-4).

Synthesis of 2-heptyl-3-hydroxy-4H-thiochromen-4-one, 1-S-PQS (Compound 5)

Under nitrogen atmosphere 5a (79 mg, 0.302 mmol) was dissolved in a mixture of ethanol (1.66 mL) and methanol (1.33 mL). Isoamylnitrite (0.108 g, 0.864 mmol) was added to the reaction solution dropwise and the mixture was cooled to 0° C. At this temperature HCl conc. (0.182 mL) was added and it was stirred for 10 minutes. The orange reaction solution was allowed to warm up to room temperature and after 1 h at 25° C. the mixture was refluxed for 3 h at 80° C. The reaction was brought to room temperature again and poured into water. Then it was extracted three times with diethyl ether and the combined organic phases were washed with brine and dried over MgSO$_4$. The solution was evaporated and the product was purified using silica gel chromatography in n-hexane/ethyl acetate 4:1. The product was obtained as a brown solid (0.032 g, 38%). Rf=0.67

(n-hexane/ethyl acetate 4:1). MS (ESI): m/z calculated for $C_{16}H_{20}O_2S+H^+$: 277.1 [M+H]$^+$, found: 276.9. $^1$H-NMR (CDCl$_3$ 400 MHz) δ (ppm): 0.88 (t, J=7.1 Hz, 3H, H-15), 1.20-1.37 (m, 6H, H-12, H-13, H-14), 1.41 (p, J=7.4 Hz, 2H, H-11), 1.75 (p, J=7.6 Hz, 2H, H-10), 2.83 (t, J=7.8 Hz, 2H, H-9), 7.51 (t, J=7.3 Hz, 1H, H-6), 7.58 (t, J=7.8 Hz, 1H, H-7), 7.63 (d, J=8.1 Hz, 1H, H-8), 8.53 (d, J=8.0 Hz, 1H, H-5). $^{13}$C-NMR (CDCl$_3$ 100 MHz) δ (ppm): 14.2 (C-15), 22.8 (C-14), 29.1 (C-10), 29.1, 29.3 (C-11, C-12), 31.3 (C-9), 31.8 (C-13), 126.1 (C-8), 126.7 (C-6), 128.8 (C-5), 129.0 (C-2), 129.2 (C-4a), 130.8 (C-7), 137.8 (C-8a), 144.1 (C-3), 174.0 (C-4).

Example 6: Synthesis of 2-heptyl-3-hydroxyquinoline-4(1H)-thione, 4-S-PQS (Compound 6)

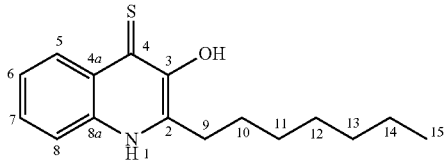 [SMILES: CCCCCCCc1[nH]c2ccccc2c(=S)c1O]

0.16 g (0.617 mmol) of 2-heptyl-3-hydroxyquinoline-4(1H)-one (PQS) were dissolved in 7.4 mL pyridine, P$_2$S$_5$ (0.206 g, 0.925 mmol) was added and the reaction was refluxed for 4 h. The mixture was allowed to cool to room temperature and poured into ice cold water. With a 6 M HCl solution the pH was brought to 7 before it was extracted three times with DCM. The combined organic phases were washed three times with 1 M HCl, dried over MgSO$_4$ and evaporated. The pure product was obtained after recrystallization in MeOH as yellow acicular crystals (0.104 g, 61%). Rf=0.27 (DCM/MeOH 10:1). MS (ESI): m/z calculated for $C_{16}H_{21}ONS+H^+$: 276.1 [M+H]$^+$ and $C_{32}H_{42}O_2N_2S_2-H^+$: 549.3 [2M-H]$^-$, found: 275.9, 549.2. $^1$H-NMR (DMSOd$_6$ 400 MHz) δ (ppm): 0.84 (t, J=7.1 Hz, 3H, H-15), 1.21-1.38 (m, 8H, H-11, H-12, H-13, H-14), 1.73 (p, J=7.6 Hz, 2H, H-10), 2.91 (t, J=7.9 Hz, 2H, H-9), 7.49 (ddd, J=1.1 Hz, 6.9 Hz, 8.2 Hz, 1H, H-6), 7.66 (ddd, J=1.4 Hz, 6.9 Hz, 8.3 Hz, 1H, H-7), 7.77 (d, J=8.3 Hz, 1H, H-8), 8.51 (dd, J=1.1 Hz, 8.4 Hz, 1H, H-5), 8.67 (s, 1H, OH), 13.16 (s, 1H, NH). $^{13}$C-NMR (DMSOd$_6$ 100 MHz) δ (ppm): 14.4 (C-15), 22.5 (C-14), 28.1 (C-10), 28.8, 29.3 (C-11, C-12), 29.5 (C-9), 31.6 (C-14), 119.7 (C-8), 125.4 (C-6), 128.2 (C-5), 129.7 (C-4a), 130.3 (C-7), 133.2 (C-8a), 135.1 (C-2), 147.6 (C-3), 169.8 (C-4).

Example 7: Synthesis of 2-heptyl-3-hydroxy-4H-chromene-4-thione, 1-O-4-S-PQS (Compound 7)

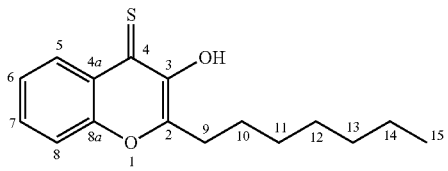

Synthesis of 2-heptylchroman-4-one (7a)

Method A:

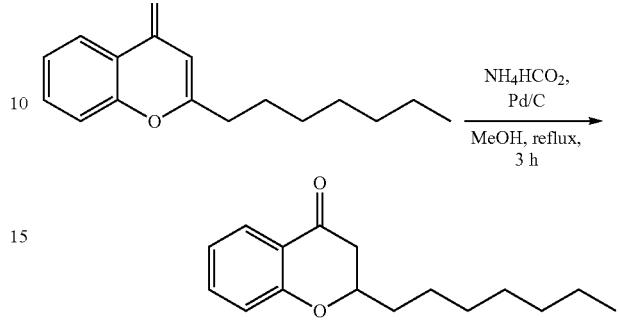

0.733 g (3.00 mmol) 2-heptyl-4H-chromen-4-one and 150 mg 10% Pd/C were dissolved in 15 ml dry MeOH. 570 mg (9.00 mmol) ammonium formiate was added and the reaction mixture was refluxed for 3 h. After filtration and evaporation of the solvent, the residue was suspended in ether and washed twice with water and once with brine, dried with MgSO$_4$, filtered and evaporated. The residue was purified by column chromatography on silica gel using DCM. The product was obtained as a colorless oil (562 mg, 76%). Rf=0.9 (DCM). Unreacted starting material was recovered by elution with 10% MeOH in DCM (170 mg, 23%). 1H-NMR (CDCl$_3$ 399.79 MHz) δ (ppm): 0.89 (m, 3H, H-15), 1.24-1.39 (m, 8H, H-11-14), 1.46 (m, 1H, H-10), 1.53 (m, 1H, H-10), 1.70 (m, 1H, H-9), 1.88 (m, 1H, H-9), 2.68 (d, J=8.0 Hz, 2H, H-3), 4.43 (m, 1H, H-2), 6.97 (m, 1H, H-8), 7.00 (m, 1H, H-6), 7.46 (m, 1H, H-7), 7.87 (dd, J=7.9 Hz, J=1.8 Hz, 1H, H-5). $^{13}$C-NMR (CDCl$_3$ 100.53 MHz) δ (ppm): 14.3 (C-15), 22.8, 29.3, 29.5, 31.9 (C-11-14), 25.1 (C-10), 35.3 (C-9), 43.2 (C-3), 78.1 (C-2), 118.2 (C-8), 121.2 (C-4a), 121.3 (C-6), 127.2 (C-5), 136.2 (C-7), 161.9 (C-8a), 192.8 (C-4). MS (ESI): m/z calculated for $C_{16}H_{22}O_2+H^+$: 269.2 [M+H]$^+$, found: 269.1.

Method B:

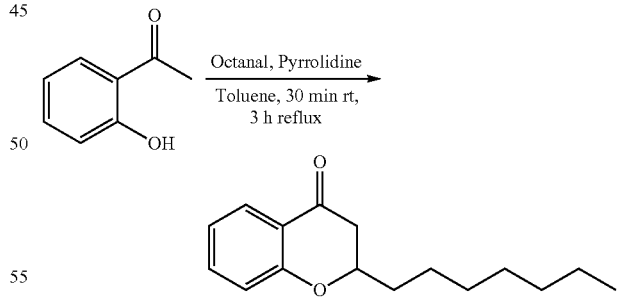

Octanal (0.256 mL, 1.642 mmol) and 0.067 mL (0.821 mmol) pyrrolidine were dissolved in 5 mL dry toluene under nitrogen atmosphere. For additional dryness mol sieve was used. After 10 minutes 2'-hydroxyacetophenone (0.224 g, 1.645 mmol) was added and the white solution was stirred for 0.5 h at room temperature. The solution became clear and was heated to 110° C. and refluxed for 3 h. The mixture was allowed to cool to room temperature and diluted with diethyl ether. Afterwards it was washed with a solution of saturated NaHCO$_3$, a solution of saturated NH$_4$Cl, water and brine.

The organic phase was dried over MgSO₄ and evaporated under reduced pressure. The product was purified by column chromatography on silica gel using n-hexane/DCM 3:1. The product was obtained as a colorless oil (0.109 g, 27%). Rf=0.65 (DCM/n-hexane 1:1).

Synthesis of 2-heptyl-3-hydroxy-Chromen-4-one, 1-O-PQS (7b)

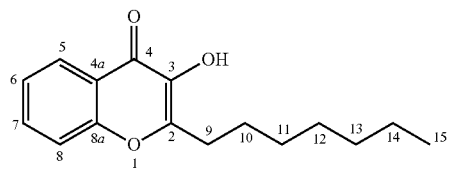 [SMILES: CCCCCCCc1oc2ccccc2c(=O)c1O]

Under nitrogen atmosphere 0.095 g (0.386 mmol) of 7a were dissolved in a mixture of ethanol/methanol 5:4 and 0.149 mL (1.103 mmol) isoamylnitrite were added carefully. The yellow solution was cooled to 0° C. and 0.232 mL of concentrated HCl was dropped slowly to the reaction mixture. After 10 minutes on ice the solution became orange and the mixture was stirred at room temperature for 1 h. Afterwards the temperature was raised to 80° C. and the reaction was stirred for further 45 minutes. The mixture was allowed to cool to room temperature and poured into H₂O. Then it was extracted three times with diethyl ether and the unified organic phases were washed with brine and dried over MgSO₄. The product was purified by column chromatography on silica gel using n-hexane/ethyl acetate 5:1 and in a second cycle DCM/MeOH 20:1. The product was obtained as grey solid (m=0.015 g, 15%). Rf=0.71 (DCM). Unreacted starting material was recovered during the first chromatographic purification cycle in n-hexane/ethyl acetate 5:1 (0.022 g, 23%). MS (ESI): m/z calculated for $C_{16}H_{20}O_3+H^+$: 261.2 [M+H]⁺, found: 260.9. ¹H-NMR (CDCl3 400 MHz) δ (ppm): 0.88 (t, J=7.0 Hz, 3H, H-15), 1.21-1.45 (m, 8H, H-11, H-12, H-13, H-14), 1.77 (p, J=7.5 Hz, 2H, H-10), 2.84 (t, J=7.7 Hz, 2H, H-9), 6.25 (s, 1H, —OH), 7.38 (t, J=7.3 Hz, 1H, H-6), 7.47 (d, J=8.5 Hz, 1H, H-8), 7.64 (t, J=7.7 Hz, 1H, H-7), 8.22 (d, J=7.8 Hz, 1H, H-5). ¹³C-NMR (CDCl₃ 100 MHz) δ (ppm): 14.2 (C-15), 22.7 (C-14), 26.8 (C-10), 29.0 (C-9), 29.1 (C-12), 29.3 (C-11), 31.9 (C-13), 118.3 (C-8), 121.4 (C-4a), 124.4 (C-6), 125.6 (C-5), 133.1 (C-7), 138.2 (C-3), 152.5 (C-2), 155.6 (C-8a), 172.6 (C-4).

Synthesis of 2-heptyl-3-hydroxy-4H-chromene-4-thione, 1-O-4-S-PQS (Compound 7)

Under nitrogen atmosphere 33.2 mg (0.127 mmol) 1-O-PQS (7b) and 42.2 mg (0.190 mmol) phosphorus P₂S₅ were dissolved in 2 mL dry pyridine and the solution was refluxed for 4 h at 170° C. During the time the color of the reaction changed from orange to brown. The mixture was brought to room temperature and poured on ice. Then it was quenched with 6 M HCl and the aqueous solution was extracted three times with DCM. The combined organic phases were washed three times with 1 M HCl and dried over MgSO₄. The solvent was evaporated and purified by silica gel chromatography in petroleum ether/ethyl acetate 5:1. The product was obtained as a brown crystalline solid (23.6 mg, 67%). Rf=0.85 (petroleum ether/ethyl acetate 5:1). MS (ESI): m/z calculated for $C_{16}H_{20}O_2S+H^+$: 277.1 [M+H]⁺ and $C_{16}H_{20}O_2S+Na^+$: 299.1 [M+Na]⁺, found: 276.9, 298.9.

¹H-NMR (CDCl₃ 400 MHz) δ (ppm): 0.89 (t, J=6.8 Hz, 3H, H-15), 1.24-1.47 (m, 8H, H-11, H-12, H-13, H-14), 1.82 (p, J=7.5 Hz, 2H, H-10), 2.93 (t, J=7.7 Hz, 2H, H-9), 7.45 (ddd, J=0.85 Hz, 7.1 Hz, 8.0 Hz, 1H, H-6), 7.54 (d, J=8.4 Hz, 1H, H-8), 7.67 (ddd, J=1.5 Hz, 7.1 Hz, 8.5 Hz, 1H, H-7), 7.84 (s, 1H, OH), 8.56 (dd, J=1.3 Hz, 8.3 Hz, 1H, H-5). ¹³C-NMR (CDCl₃ 100 MHz) b (ppm): 14.19 (C-15), 22.68 (C-14), 26.79 (C-10), 29.08 (C-12), 29.44 (C-11), 29.92 (C-9), 31.75 (C-13), 118.43 (C-8), 125.76 (C-6), 128.26 (C-4a), 128.76 (C-5), 132.66 (C-7), 146.77 (C-3), 148.76 (C-2), 150.93 (C-8a), 186.90 (C-4).

Example 8: Synthesis of PQS-Oxime (Compound 8)

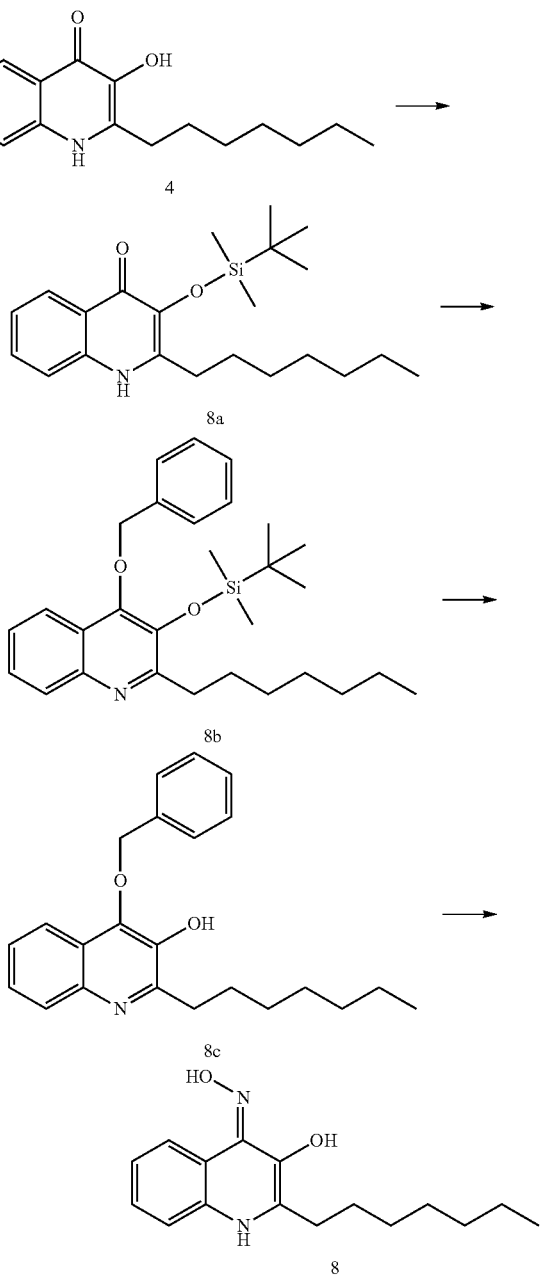

Synthesis of 3-((tert-butyldimethylsilyl)oxy)-2-heptylquinolin-4(1H)-one (8a)

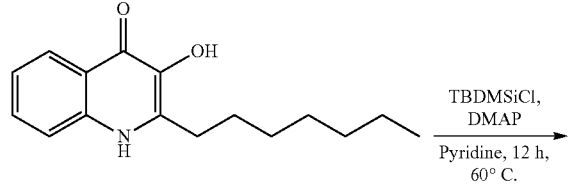

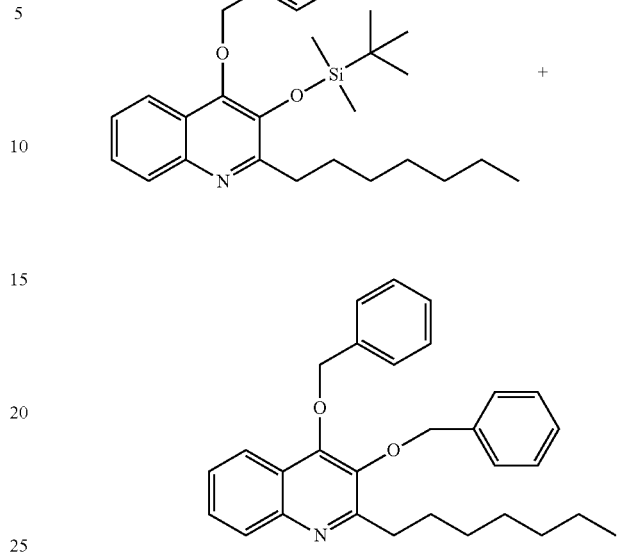

0.230 g (0.887 mmol) PQS and 22 mg DMAP (0.177 mmol) were dissolved in 10 ml dry pyridine under nitrogen atmosphere and warmed up to 60° C. 267 mg (1.77 mmol) TBDMSiCl was added in one portion and the reaction was stirred at 60° C. for 12 h. The solvent was evaporated under reduced pressure at 60° C. The residue was solved in DCM and washed twice with water and once with brine, dried with MgSO$_4$, filtered and evaporated. The residue was purified by column chromatography on silica gel using DCM/MeOH (97:3). The product was obtained as a white crystalline solid (293.5 mg, 88%). Rf=0.95 (DCM/MeOH (97:3). $^1$H-NMR (CDC$_3$ 399.79 MHz) δ (ppm): 0.35 (s, 6H, =Si—(CH$_3$)$_2$), 0.83 (m, 3H, H-15), 1.00 (s, 9H, —C—(CH$_3$)$_3$), 1.10-1.36 (m, 8H, H-11-14), 1.71 (m, 2H, H-10), 2.85 (m, 2H, H-9), 7.18 (ddd, J=8.7 Hz, J=8.3 Hz, J=0.7 Hz, 1H, H-6), 7.46 (ddd, J=8.7 Hz, J=8.4 Hz, J=1.3 Hz, 1H, H-7), 7.59 (d, J=8.4 Hz, 1H, H-8), 8.28 (dd, J=8.3 Hz, J=1.3 Hz, 1H, H-5), 10.67 (s, 1H, H-1). $^{13}$C-NMR (CDCl$_3$ 100.53 MHz) δ (ppm): −2.9 (2C, =Si—(CH$_3$)$_2$), 14.4 (C-15), 19.1 (—C—(CH$_3$)$_3$), 22.7, 29.2, 29.7, 31.8 (C-11-14), 26.4 (3C, —C—(CH$_3$)$_3$), 28.7 (C-10), 30.0 (C-9), 117.8 (C-8), 122.5 (C-6), 124.7 (C-4a), 125.6 (C-5), 130.5 (C-7), 137.5 (C-3), 137.8 (C-8a), 142.5 (C-2), 171.5 (C-4). ESI-MS: m/z=371.95 [M–H]$^-$, calc. for C$_{22}$H$_{34}$NO$_2$Si$^-$=372.24.

Synthesis of 4-(benzyloxy)-3-((tert-butyldimethylsilyl)oxy)-2-heptylquinoline (8b)

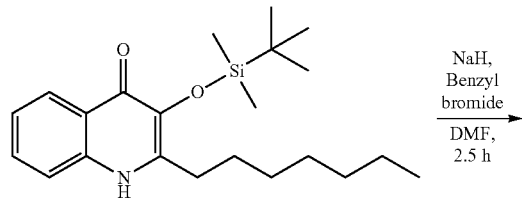

0.229 g (0.613 mmol) PQS-TBDMSi and 40 mg NaH (1.0 mmol, 60% in mineral oil) were dissolved in 6 ml dry DMF under nitrogen atmosphere and were stirred for 30 min at room temperature. 175 mg (1.0 mmol) benzyl bromide was solved in 4 ml DMF and added to the reaction dropwise. A black precipitate appeared by the addition of benzyl bromide. After the reaction of 2 h time at room temperature, the now clear solution was quenched by the addition of 5 ml water. Water and DMF were evaporated with reduced pressure at 60° C. The residue was solved in DCM and washed twice with water and once with brine, dried with MgSO$_4$, filtered and evaporated. The residue was purified by column chromatography on silica gel using ethyl acetate/petrol ether (1:5). The product was obtained as off-white solid (48 mg, 17%). Rf=0.95. $^1$H-NMR (CDCl$_3$ 399.79 MHz) δ (ppm): 0.21 (s, 6H, =Si—(CH$_3$)$_2$), 0.90 (m, 3H, H-15), 1.09 (s, 9H, —C—(CH$_3$)$_3$), 1.26-1.50 (m, 8H, H-11-14), 1.82 (m, 2H, H-10), 3.03 (m, 2H, H-9), 5.18 (s, 2H, —O—CH$_2$—Ar), 7.29-7.41 (m, 4H, H-6, Ar—CH), 7.46 (m, 2H, Ar—CH), 7.54 (ddd, J=8.9 Hz, J=8.4 Hz, J=1.5 Hz, 1H, H-7), 7.95 (m, 1H, H-5), 7.98 (d, J=8.4 Hz, 1H, H-8). $^{13}$C-NMR (CDCl$_3$ 100.53 MHz) δ (ppm): −3.9 (2C, =Si—(CH$_3$)$_2$), 14.2 (C-15), 18.6 (—C—(CH$_3$)$_3$), 22.8, 29.5, 29.9, 32.0 (C-11-14), 26.1 (3C, —C—(CH$_3$)$_3$), 28.9 (C-10), 34.4 (C-9), 74.8 (—O—CH$_2$—Ar), 121.5 (C-5), 124.4 (C-4a), 125.5 (C-6), 127.6 (C-7), 127.9 (2C, Ar—CH), 128.2 (Ar—CH), 128.5 (C-8), 128.6 (2C, Ar—CH), 137.0 (Ar—C—), 139.4 (C-3), 144.6 (C-8a), 149.7 (C-4), 160.4 (C-2).

The main product isolated was the 3,4-bis(benzyloxy)-2-heptylquinoline (8d) (140 mg, 52%). Rf=0.95. $^1$H-NMR (CDCl$_3$ 399.79 MHz) δ (ppm): 0.95 (m, 3H, H-15), 1.25-1.55 (m, 8H, H-11-14), 1.87 (m, 2H, H-10), 3.05 (m, 2H, H-9), 5.19 (s, 2H, —O—CH$_2$—Ar), 5.37 (s, 2H, —O—CH$_2$—Ar), 7.34-7.54 (m, 11H, H-6, Ar—CH), 7.63 (ddd, J=8.9 Hz, J=8.4 Hz, J=1.5 Hz, 1H, H-7), 8.07 (d, J=8.5 Hz, 1H, H-5), 8.14 (d, J=8.4 Hz, 1H, H-8).

Synthesis of 4-(benzyloxy)-2-heptylquinolin-3-ol (8c)

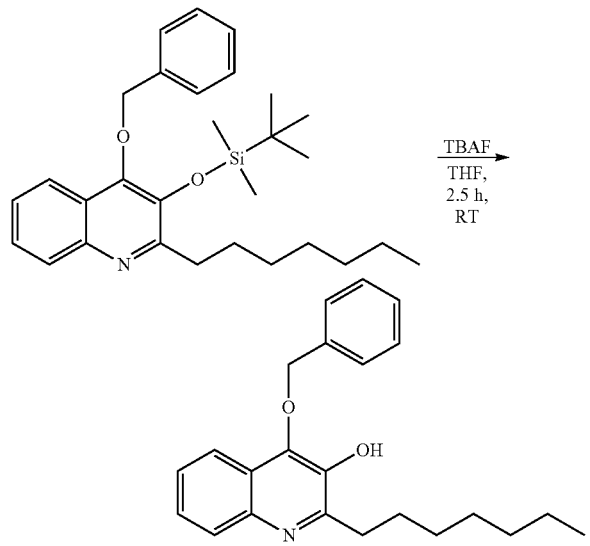

45 mg (0.097 mmol) PQS-TBDMSi-Bn was solved in 5 ml dry THF under nitrogen atmosphere and 200 µl TBAF (1M in THF) was added at 0° C. After the reaction time of 2.5 h at room temperature, water was added and the mixture extracted with ethyl acetate. The organic phase was washed with brine, dried with MgSO$_4$, filtered and evaporated. The residue was purified by column chromatography on silica gel using ethyl acetate/petrol ether (1:5). The product was received as off-white solid (30 mg, 88.5%). Rf=0.95. $^1$H-NMR (CDCl$_3$ 399.79 MHz) δ (ppm): 0.87 (m, 3H, H-15), 1.20-1.42 (m, 8H, H-11-14), 1.74 (m, 2H, H-10), 2.98 (m, 2H, H-9), 5.18 (s, 2H, —O—CH$_2$—Ar), 7.38 (m, 5H, Ar—CH), 7.47 (ddd, J=8.7 Hz, J=8.3 Hz, J=1.2 Hz, 1H, H-6), 7.54 (ddd, J=8.7 Hz, J=8.3 Hz, J=1.5 Hz, 1H, H-7), 7.93 (dd, J=8.3 Hz, J=1.2 Hz, 1H, H-5), 8.05 (d, J=8.3 Hz, 1H, H-8). $^{13}$C-NMR (CDCl$_3$ 100.53 MHz) δ (ppm): 14.2 (C-15), 22.8, 29.3, 29.8, 31.9 (C-11-14), 28.6 (C-10), 34.1 (C-9), 76.5 (—O—CH$_2$—Ar), 120.6 (C-5), 123.0 (C-4a), 126.0 (C-6), 126.9 (C-7), 128.3 (2C, Ar—CH), 129.1 (2C, C-8, Ar—CH), 136.5 (Ar—C—), 140.8 (C-3), 143.8 (C-8a), 144.7 (C-4), 156.3 (C-2).

Synthesis of 2-heptyl-3-hydroxyquinolin-4(1H)-one oxime, PQS-Oxime (Compound 8)

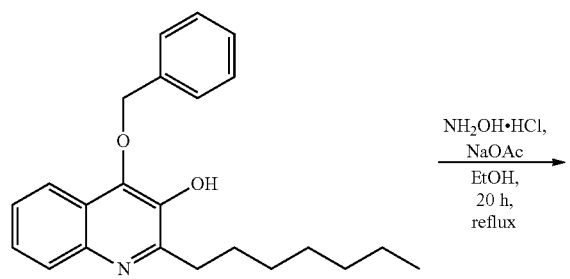

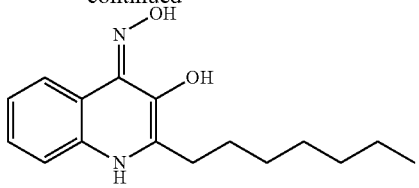

30 mg (0.086 mmol) PQS-Bn was solved in 10 ml EtOH together with 0.5 g (7.2 mmol) NH$_2$OH·HCl and 0.6 g (7.3 mmol) sodium acetate. The reaction was stirred at reflux conditions for 20 h. After the reaction cooled to room temperature the solvent was evaporated under reduced pressure. The residue was dissolved in ethyl acetate and washed once with water and sat. NH$_4$Cl solution. The organic phase was tried with MgSO$_4$, filtered and evaporated leaving a yellow residue which was purified by column chromatography on silica gel using DCM/MeOH (4:1). The product was received as a yellow solid (15 mg, 70.5%). Rf=0.95. $^1$H-NMR (DMSO-d$_6$ 399.79 MHz) δ (ppm): 0.83 (m, 3H, H-15), 1.15-1.40 (m, 8H, H-11-14), 1.69 (m, 2H, H-10), 2.97 (m, 2H, H-9), 7.47 (m, 2H, H-6), 7.67 (m, 2H, H-7), 7.79 (s, br, 1H, =N—OH), 7.91 (d, J=8.5 Hz, 1H, H-8), 8.32 (d, J=8.7 Hz, 1H, H-5). $^{13}$C-NMR (DMSO-d$_6$ 100.53 MHz) δ (ppm): 13.9 (C-15), 22.0, 28.5, 28.9, 31.2 (C-11-14), 28.0 (C-10), 29.9 (C-9), 116.0 (C-4a), 121.4 (C-8), 122.8 (C-5), 124.4 (C-6), 129.8 (C-7), 131.9 (C-3), 137.1 (C-8a), 145.8 (C-4), 147.5 (C-2).

$^1$H-NMR (MeOD-d$_4$ 400.13 MHz) δ (ppm): 0.90 (m, 3H, H-15), 1.25-1.50 (m, 8H, H-11-14), 1.80 (m, 2H, H-10), 3.02 (m, 2H, H-9), 7.56 (m, 1H, H-6), 7.77 (m, 2H, H-7-8), 8.24 (d, J=8.4 Hz, 1H, H-5).

(Comparative) Example 9: Synthesis of 3-hydroxy-2-methyl-thiochromen-4-one (Compound 9)

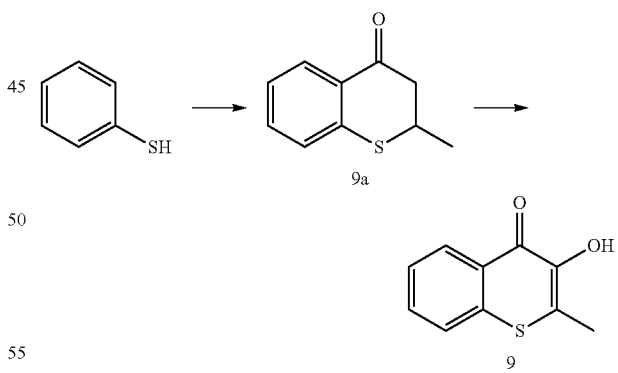

Synthesis of 2-methylthiochroman-4-one (9a)

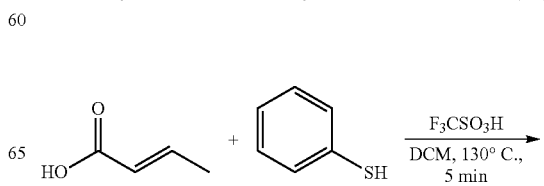

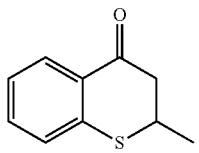

172 mg Crotonic acid (2.0 mmol) was solved in 1 ml dry DCM in a Schleck tube with a septum under nitrogen. 0.2 ml Thiophenol (2.0 mmol) was added and the mixture was cooled with an ice-bath. Under nitrogen 2 ml trifluoromethanesulfonic acid was added and the mixture was heated in an oil bath at 130° C. with a reflux cooler for 5 min. the reaction was allowed to cool to room temperature and was poured on ice. DCM was added and the phases separated. The water phase was washed with DCM and the combined organic phases washed twice with sat. NaHCO$_3$ sol. and Brine. The organic phases was dried with MgSO$_4$, filtered and the solved evaporated. The product was purified by column chromatography on silica 60 with PE/DCM 5:1 and PE/DCM 1:1. The product was collected at last as the only fluorescent substance on TLC. The product was obtained as slightly yellow oil (m=287 mg, 80.5%). Rf=0.26 (PE/DCM 1:1). $^1$H-NMR (CDCl$_3$ 399.79 MHz) δ (ppm): 1.44 (d, J=6.8 Hz, 3H, H-9), 2.76 (dd, J=11.6 Hz, J=16.5 Hz, 1H, H-3), 3.01 (dd, J=3.1 Hz, J=16.5 Hz, 1H, H-3), 3.63 (m, 1H, H-2), 7.16 (m, 1H, H-6), 7.25 (m, 1H, H-8), 7.38 (m, 1H, H-7), 8.09 (dd, J=8.0 Hz, J=1.5 Hz, 1H, H-5). $^{13}$C-NMR (CDCl$_3$ 100.53 MHz) δ (ppm): 20.6 (C-9), 36.6 (C-2), 48.0 (C-3), 125.0 (C-6), 127.6 (C-8), 129.1 (C-5), 130.5 (C-4a), 133.6 (C-7), 141.9 (C-8a), 194.8 (C-4).

Synthesis of
3-hydroxy-2-methyl-thiochromen-4-one (Compound 9)

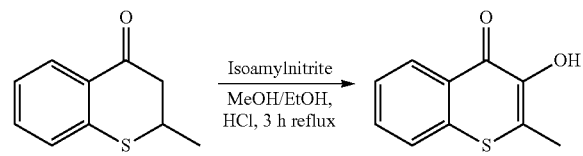

275 mg 2-methylthiochroman-4-one (1.54 mmol) was solved in 2.2 ml MeOH and 2.8 ml EtOH in a Schleck tube with a septum under nitrogen. 625 μl Isoamylnitrite (4.6 mmol) was added and the mixture was cooled to 0° C. Under nitrogen 0.9 ml conc. HCl was added and the mixture was kept at 0° C. for 10 min. The reaction was allowed to warm to room temperature and was kept at this for 1 h. Afterwards, the reaction was heated to reflux for 3 h in which the color changed from yellow to red. After the reaction time, the mixture was poured in water and extracted with ether. The combined organic phases washed twice with Brine, dried with MgSO$_4$, filtered and the solved evaporated leaving a red crystalline solid. The solid was dispersed in PE/EE 5:1, filtered of and washed with the same solvent mixture. The filtrated was collected and the solvent evaporated. The residual solid was dispersed in PE, filtered of and washed with PE. After drying under vacuum both solid fractions showed the clean product in NMR. The product was obtained as a red crystalline solid (m=120 mg, 40.5%). Rf=0.46 (PE/EE 5:1). $^1$H-NMR (CDCl$_3$ 399.79 MHz) δ (ppm): 2.47 (s, 3H, H-9), 7.52 (m, 1H, H-6), 7.58 (m, 1H, H-7), 7.62 (m, 1H, H-8), 8.52 (m, 1H, H-5). $^{13}$C-NMR (CDCl$_3$ 100.53 MHz) δ (ppm): 16.8 (C-9), 123.9 (C-2), 125.9 (C-8), 126.8 (C-6), 128.9 (C-5), 129.1 (C-4a), 130.9 (C-7), 137.8 (C-8a), 144.5 (C-3), 174.0 (C-4).

Example 10: Synthesis of
3-hydroxy-2-butyl-thiochromen-4-one (Compound 10)

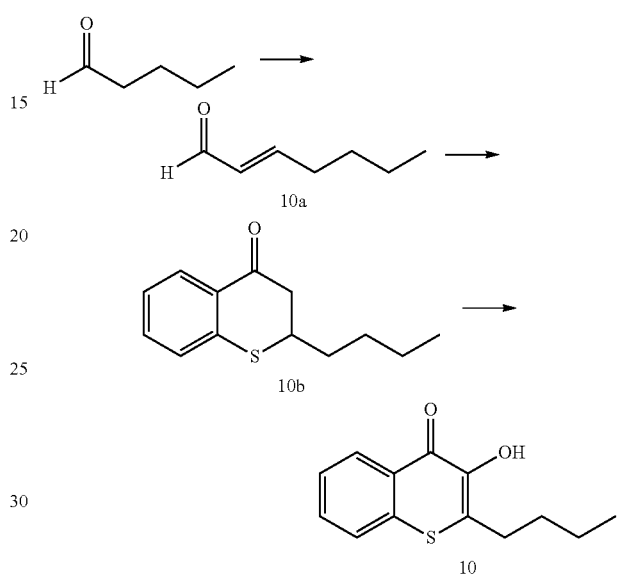

Synthesis of (E)-hept-2-enoic acid (10a)

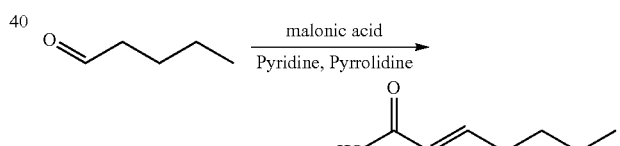

0.5 g malonic acid (4.8 mmol) was solved in 3 ml pyridine and 0.51 ml pentanal (4.8 mmol) and 50 μl pyrrolidine was added. The mixture warmed up and the evolution of gas was observed. The mixture was stirred at reflux temperature for 30 min and was then poured in ice water and acidified with conc. HCl. The mixture was extracted with ethyl acetate and the combined organic phases washed with Brine, dried with MgSO$_4$, filtered and the solved evaporated. The product was purified by column chromatography using PE/EE 5:1. The product was obtained as colorless oil (m=0.4 mg, 65%). Rf=0.175 (PE/EE 5:1).

Synthesis of 2-butylthiochroman-4-one (10b)

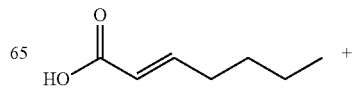

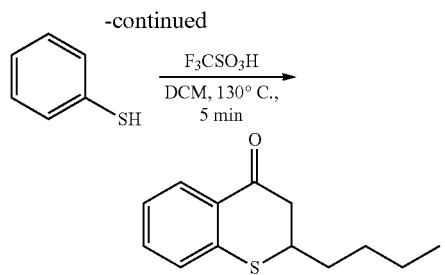

340 mg trans-2-heptenic acid (2.65 mmol) was solved in 1.0 ml dry DCM in a Schleck tube with a septum under nitrogen. 0.27 ml Thiophenol (2.65 mmol) was added and the mixture was cooled with an ice-bath. Under nitrogen 2.5 ml trifluoromethanesulfonic acid was added and the mixture stirred at 0° C. for 5 min. After that, the mixture was heated in an oil bath at 130° C. with a reflux cooler for 5 min. the reaction was allowed to cool to room temperature and was poured on ice. DCM was added and the phases separated. The water phase was washed with DCM and the combined organic phases washed twice with sat. NaHCO$_3$ sol. and Brine. The organic phases was dried with MgSO$_4$, filtered and the solved evaporated. The product was purified by column chromatography on silica 60 with PE/DCM 1:1. The product was obtained as slightly yellow oil (m=198 mg, 34%). Rf=0.43 (PE/DCM 1:1). $^1$H-NMR (CDCl$_3$ 399.79 MHz) δ (ppm): 0.92 (m, 3H, H-12), 1.35 (m, 2H, H-11), 1.45 (m, 2H, H-10), 1.72 (m, 2H, H-9), 2.80 (dd, J=16.3 Hz, J=11.3 Hz, 1H, H-3), 3.05 (dd, J=16.3 Hz, J=3.0 Hz, 1H, H-3), 3.50 (m, 1H, H-2), 7.16 (m, 1H, H-6), 7.26 (dd, J=8.0 Hz, J=1.0 Hz, 1H, H-8), 7.38 (m, 1H, H-7), 8.08 (dd, J=8.0 Hz, J=1.5 Hz, 1H, H-5). $^{13}$C-NMR (CDC$_3$ 100.53 MHz) δ (ppm): 14.0 (C-12), 22.5 (C-11), 29.0 (C-10), 34.4 (C-9), 41.8 (C-2), 46.4 (C-3), 125.0 (C-6), 127.8 (C-8), 129.1 (C-5), 130.8 (C-4a), 133.6 (C-7), 141.9 (C-8a), 194.9 (C-4).

Synthesis of 3-hydroxy-2-methyl-thiochromen-4-one (Compound 10)

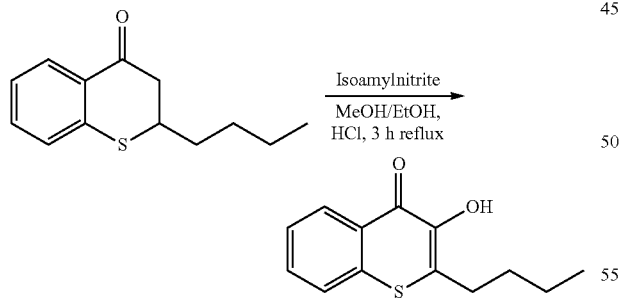

193 mg 2-butylthiochroman-4-one (0.876 mmol) was solved in 1.0 ml MeOH and 1.5 ml EtOH in a Schleck tube with a septum under nitrogen. 360 µl Isoamylnitrite (2.63 mmol) was added and the mixture was cooled to 0° C. Under nitrogen 0.51 ml conc. HCl was added and the mixture was kept at 0° C. for 10 min. The reaction was allowed to warm to room temperature and was kept at this for 1 h. Afterwards, the reaction was heated to reflux for 3 h in which the color changed from yellow to red. After the reaction time, the mixture was poured in water and extracted with ether. The combined organic phases washed twice with Brine, dried with MgSO$_4$, filtered and the solved evaporated leaving a brown oil. The product was purified by silica gel 60 column chromatography using DCM. The product was obtained as a brown crystalline solid (m=109 mg, 53.1%). Rf=0.43 (DCM). $^1$H-NMR (CDCl$_3$ 399.79 MHz) δ (ppm): 0.96 (m, 3H, H-12), 1.45 (m, 2H, H-11), 1.73 (m, 2H, H-10), 2.83 (m, 2H, H-9), 7.49 (m, 1H, H-6), 7.57 (m, 1H, H-7), 7.62 (m, 1H, H-8), 8.52 (d, J=8.1 Hz, 1H, H-5). $^{13}$C-NMR (CDCl$_3$ 100.53 MHz) δ (ppm): 13.9 (C-12), 22.5 (C-11), 30.9 (C-9), 31.1 (C-10), 126.1 (C-8), 126.7 (C-6), 128.8 (C-5), 129.0 (C-4a), 129.2 (C-2), 130.8 (C-7), 137.9 (C-8a), 144.1 (C-3), 174.1 (C-4).

Example 11: Synthesis of 6-fluoro-2-heptyl-3-hydroxy-4H-thiochromen-4-one (Compound 11)

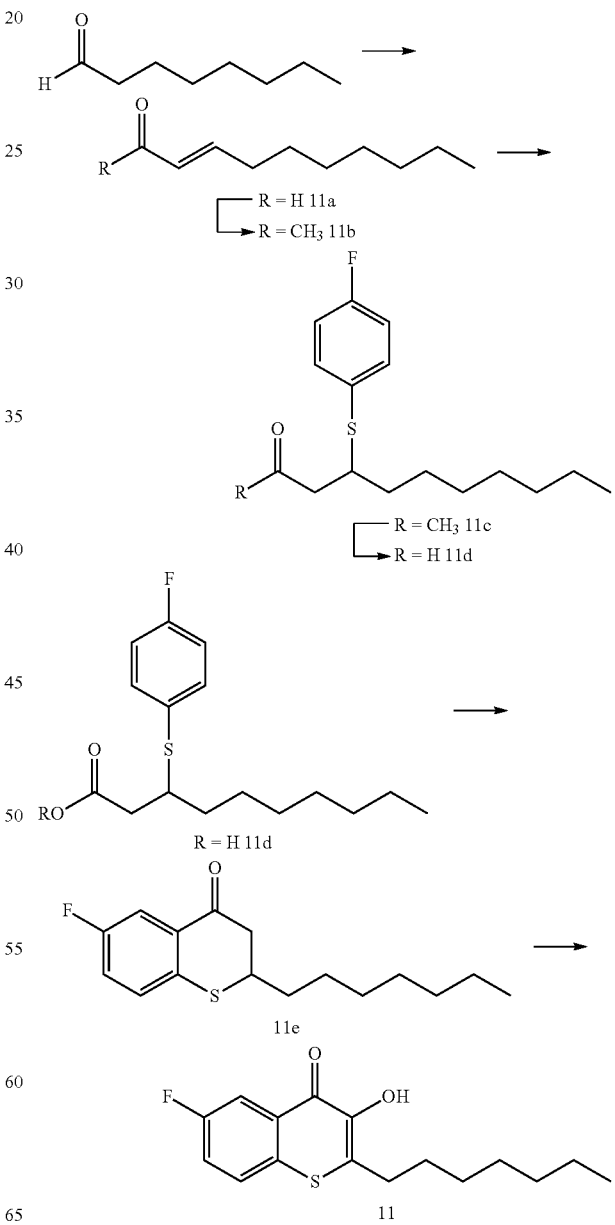

Synthesis of (E)-dec-2-enoic acid (11a)

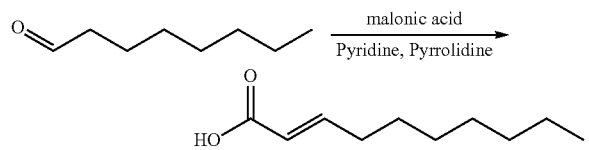

2.5 g malonic acid (24 mmol) was solved in 10 ml dry pyridine and 3.75 ml octanal (24 mmol) and 250 µl pyrrolidine was added. The mixture warmed up and the evolution of gas was observed. The mixture was stirred at room temperatures for 20 h and was then poured in ice water and acidified with conc. HCl. The mixture was extracted with ethyl acetate and the combined organic phases washed with Brine, dried with $MgSO_4$, filtered and the solved evaporated. The product was purified by column chromatography using PE/EE 5:1. The product was obtained as colorless oil (m=2.97 mg, 72.7%). Rf=0.175 (PE/EE 5:1). $^1$H-NMR ($CDCl_3$ 399.79 MHz) δ (ppm): 0.89 (m, 3H, —$CH_2$—$CH_3$), 1.18-1.39 (m, 12H, —($CH_2$)$_4$—$CH_3$), 1.47 (m, 2H, —$CH_2$—($CH_2$)$_4$—$CH_3$), 2.23 (m, 1H, =CH—$CH_2$—), 5.82 (dt, J=15.6 Hz, J=1.5 Hz, 1H, HOOC—CH=), 7.08 (dt, J=15.6 Hz, J=7.08 Hz, 1H, =CH—$CH_2$—). $^{13}$C-NMR ($CDCl_3$ 100.53 MHz) δ (ppm): 14.2 (—$CH_2$—$CH_3$), 22.8, 29.18, 29.25, 31.9 (—($CH_2$)$_4$—$CH_3$), 28.0 (—$CH_2$—($CH_2$)$_4$—$CH_3$), 32.5 (=CH—$CH_2$—), 120.6 (HOOC—CH=), 152.6 (=CH—$CH_2$—), 171.7 (HOOC—).

Synthesis of methyl 3-((4-fluorophenyl)thio)decanoate (11c)

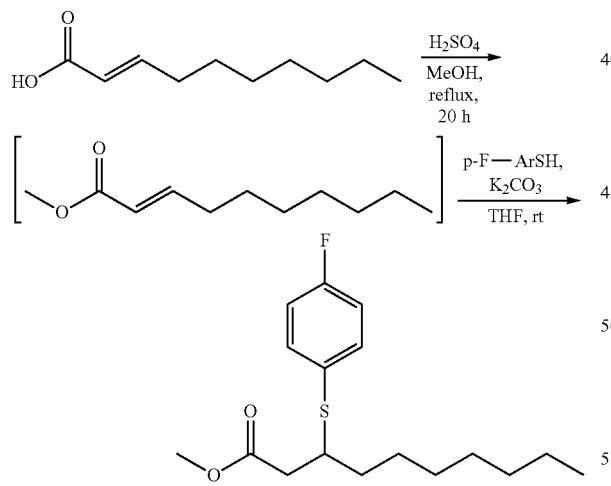

540 mg 2-Decenic acid (2.58 mmol) was solved in 50 ml MeOH and 0.5 ml conc. $H_2SO_4$ was added. The mixture was stirred at reflux temperature for 20 h. Water was added and the mixture was extracted with $Et_2O$. The combined organic phases were washed with sat. $Na_2CO_3$ and Brine, dried with $MgSO_4$, filtered and the solved evaporated. The methyl ester 11b was obtained as slightly yellow oil (480 mg) and used without further purification. 480 mg 2-decenic acid methyl ester (11b, 2.6 mmol) and 560 µl p-F—ArSH (5.2 mmol) were solved in 25 ml THF and 830 mg $K_2CO_3$ (6.0 mmol) was added and the mixture was stirred under reflux temperature for 16 h. The solvent was evaporated to approximately 5 ml. 1M HCl was added and the water phase extracted with DCM. The combined organic phases were washed with sat. $NaHCO_3$ sol. and Brine, died with $MgSO_4$, filtered and the solvent evaporated. The residue was purified by column chromatography with silica gel 60 using petrol ether/ethyl acetate 20:1. The product was obtained as colorless oil (m=608 mg, 74.8%). Only traces of 2-decenic acid methyl ester was visible in NMR. Rf=0.36 (ether/ethyl acetate 20:1). $^1$H-NMR ($CDCl_3$ 399.79 MHz) δ (ppm): 0.88 (m, 3H, —$CH_2$—$CH_3$), 1.19-1.61 (m, 12H, —($CH_2$)$_6$—$CH_3$), 2.53 (dd, J=7.2 Hz, J=1.1 Hz, 2H, $CH_3$OOC—$CH_2$—), 3.36 (m, 1H, =CH—S—), 3.67 (s, 1H, $CH_3$OOC—), 7.01 (m, 2H, FC—CH—CH—), 7.44 (m, 2H, FC—CH—CH—). $^{13}$C-NMR ($CDCl_3$ 100.53 MHz) δ (ppm): 14.2 (—$CH_2$—$CH_3$), 22.7, 26.9, 29.2, 29.4, 31.9, 34.7 (—($CH_2$)$_6$—$CH_3$), 40.4 ($CH_3$OOC—$CH_2$—), 46.1 (=CH—S—), 51.8 ($CH_3$OOC—), 116.1 (d, J=21.4 Hz, 2C, FC—CH—CH=), 128.8 (—S—Ce), 136.1 (d, J=8.3 Hz, 2C, FC—CH—CH—), 162.6 (d, J=249 Hz, FC—CH—CH—), 172.1 ($CH_3$OOC—).

Synthesis of 3-((4-fluorophenyl)thio)decanoic acid (11d)

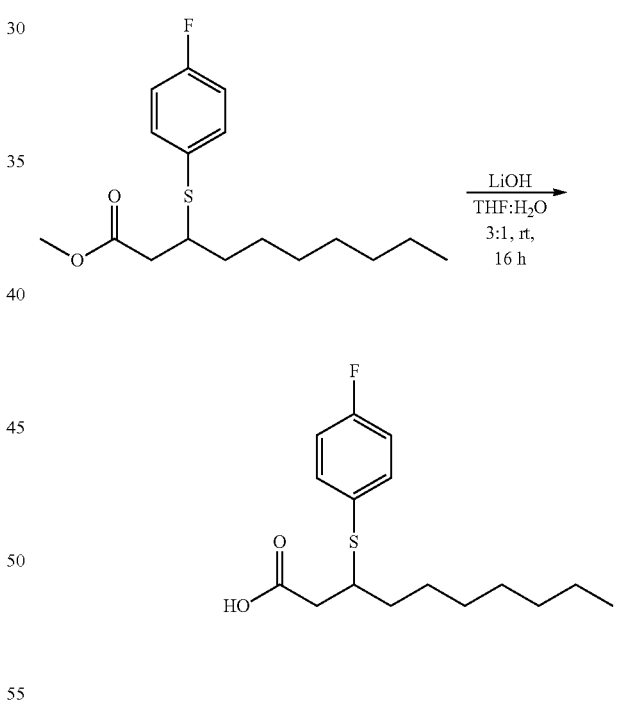

600 mg Thioether (1.92 mmol) was solved in 20 ml THF/$H_2O$ (3:1) and 192 mg LiOH (8 mmol) was added. The mixture was stirred at room temperature for 16 h. The THF was evaporated and the mixture acidified with 1M HCl. The water phase was extracted with ethyl acetate. The combined organic phases were washed with Brine, died with $MgSO_4$, filtered and the solvent evaporated. The residue was purified by column chromatography with silica gel 60 using petrol ether/ethyl acetate 9:1 and then 1:1. The product was obtained as colorless oil (m=327 mg, 57%). Rf=0.64 (ether/ethyl acetate 1:1).

Synthesis of 6-fluoro-2-heptylthiochroman-4-one (11e)

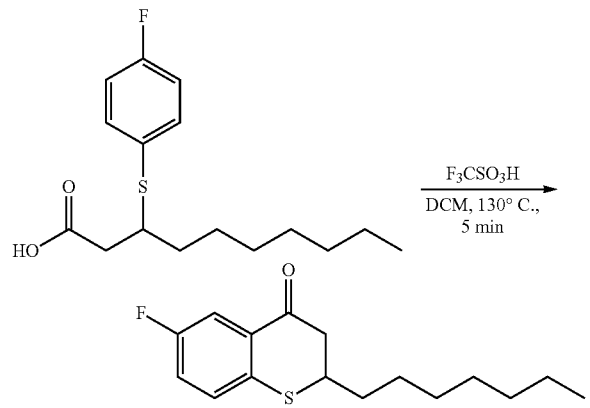

85 mg Thioether (0.28 mmol) was solved in 1 ml DCM in a Schleck tube and 1.5 ml trifluoromethanesulfonic acid was added whereby the mixture turned immediately pink. The mixture was heated in an oil bath at 135° C. with a reflux cooler for 5 min. The reaction was allowed to cool to room temperature and was poured on ice whereby the pink color disappeared. DCM was added and the phases separated. The water phase was washed with DCM and the combined organic phases washed with water and Brine. The organic phases was dried with MgSO$_4$, filtered and the solved evaporated. TLC in PE/DCM 1:1 showed the product as a highly fluorescent spot. The product was purified by column chromatography on silica 60 with PE/DCM 1:1. The product was obtained as colorless oil (m=52 mg, 66.2%). Rf=0.6 (PE/DCM 1:1). $^1$H-NMR (CDCl$_3$ 399.79 MHz) δ (ppm): 0.88 (m, 3H, H-15), 1.23-1.34 (m, 8H, H-11-14), 1.46 (m, 2H, H-10), 1.71 (m, 2H, H-9), 2.78 (dd, J=16.5 Hz, J=11.2 Hz, 1H, H-3), 3.04 (dd, J=16.5 Hz, J=3.0 Hz, 1H, H-3), 3.48 (m, 1H, H-2), 7.13 (m, 1H, H-7), 7.24 (dd, J=8.4 Hz, J=5.0 Hz, 1H, H-8), 7.76 (dd, J=9.3 Hz, J=2.9 Hz, 1H, H-5). $^{13}$C-NMR (CDCl$_3$ 100.53 MHz) δ (ppm): 14.2 (C-15), 22.8, 29.2, 29.3, 31.9 (C-11-14), 26.8 (C-10), 34.5 (C-9), 42.0 (C-2), 46.2 (C-3), 115.0 (d, J=22.8 Hz, C-5), 121.5 (d, J=23.0 Hz, C-7), 129.6 (d, J=7.0 Hz, C-8), 132.1 (d, J=5.8 Hz, C-4a), 137.0 (d, J=3.1 Hz, C-8a), 160.6 (d, J=246.5 Hz, C-6), 194.0 (d, J=1.7 Hz, C-4).

Synthesis of 6-fluoro-2-heptyl-3-hydroxy-4H-thiochromen-4-one (Compound 11)

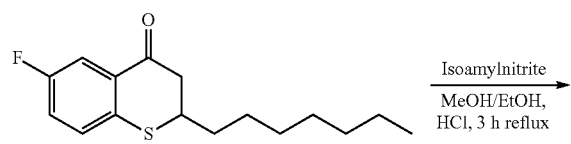

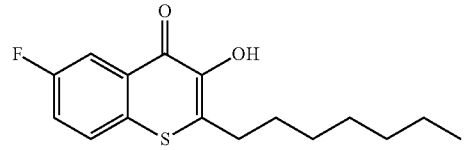

51 mg 6-F-2-heptylthiochroman-4-one (0.182 mmol) was solved in 1.1 ml MeOH and 1.4 ml EtOH in a Schleck tube with a septum under nitrogen. 75 µl Isoamylnitrite (0.55 mmol) was added and the mixture was cooled to 0° C. Under nitrogen 0.11 ml conc. HCl was added and the mixture was kept at 0° C. for 10 min. The reaction was allowed to warm to room temperature and was kept at this for 1 h. Afterwards, the reaction was heated to reflux for 3 h in which the color changed from yellow to red. After the reaction time, the mixture was poured in water and extracted with ether. The combined organic phases washed twice with Brine, dried with MgSO$_4$, filtered and the solved evaporated leaving a brown oil. The product was purified by silica gel 60 column chromatography using DCM. The product was obtained as a brown crystalline solid (m=9.5 mg, 17%). Rf=0.56 (DCM). $^1$H-NMR (CDCl$_3$ 399.79 MHz) δ (ppm): 0.89 (m, 3H, H-15), 1.20-1.47 (m, 8H, H-11-14), 1.75 (m, 2H, H-10), 2.84 (m, 2H, H-9), 7.36 (m, 1H, H-7), 7.50 (s, br, 1H, —OH), 7.63 (dd, J=9.1 Hz, J=4.8 Hz, 1H, H-8), 8.18 (dd, J=9.5 Hz, J=2.9 Hz, 1H, H-5). $^{13}$C-NMR (CDCl$_3$ 100.53 MHz) b (ppm): 14.2 (C-15), 22.8, 29.08, 29.11, 29.3, 31.8 (C-10-14), 31.3 (C-9), 113.9 (d, J=23.0 Hz, C-5), 120.2 (d, J=25.0 Hz, C-7), 128.4 (d, J=8.0 Hz, C-8), 129.9 (C-2), 130.7 (d, J=7.3 Hz, C-4a), 133.4 (d, J=2.2 Hz, C-8a), 143.8 (C-2), 161.5 (d, J=249 Hz, C-6), 173.4 (C-4). ESI-MS: m/z=294.85 [M+H]$^+$, calc. for C$_{16}$H$_{19}$FO$_2$S+H$^+$=295.12. ESI-MS: m/z=335.95 [M+C$_2$H3N+H]$^+$, calc. for C$_{18}$H$_{22}$FNO$_2$S+H$^+$=336.14.

Example 12: Determination of the Minimum Inhibitory Concentration (MIC) with Non-Pathogenic *E. coli* and *B. subtilis* and/or Pathogenic Strains of *S. aureus* Including Three MRSA Strains (USA 300, Mu50 and DSM18827) as Well as the Pathogenic Fungus *Candida albicans*

Minimum inhibitory concentrations (MIC) for compounds 1 to 11 with non-pathogenic *E. coli* and *B. subtilis* and/or pathogenic strains of *S. aureus* including three MRSA strains (USA 300, Mu50 and DSM18827) as well as the pathogenic fungus *Candida albicans* were determined in 96-well plates with serial dilutions in LB medium. The results are summarized in Tables 1 and 2.

TABLE 1

| | | | |
|---|---|---|---|
| 1 | *E. coli* K12 | >1000 µM | >243 µg/mL |
| | *B. subtilis* | >1000 µM | >243 µg/mL |
| | *S. aureus* NCTC 8325 | >1000 µM | >243 µg/mL |

TABLE 1-continued

| Structure | # | Organism | MIC (μM) | MIC (μg/mL) |
|---|---|---|---|---|
| 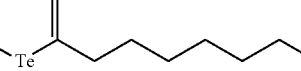 | 2 | B. subtilis | 100-250 μM | 36-89 μg/mL |
| 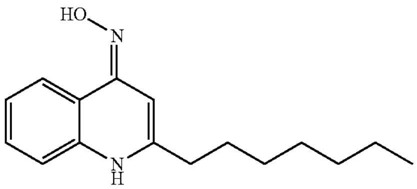 [SMILES: CCCCCCCc1c/c(=N/O)c2ccccc2[nH]1] | 3 | E. coli K12<br>B. subtilis<br>S. aureus NCTC 8325<br>S. aureus USA 300<br>S. aureus Mu50<br>S. aureus DSM18827<br>C. albicans | 300 μM<br>50 μM<br>60 μM<br>60 μM<br>60 μM<br>100 μM | 78 μg/mL<br>12.9 μg/mL<br>15.5 μg/mL<br>15.5 μg/mL<br>15.5 μg/mL<br>25.8 μg/mL |
| 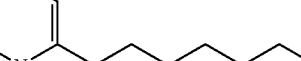 | 4 | E. coli K12<br>B. subtilis<br>S. aureus NCTC 8325 | >1000 μM<br>>1000 μM<br>>1000 μM | >259 μg/mL<br>>259 μg/mL<br>>259 μg/mL |
| 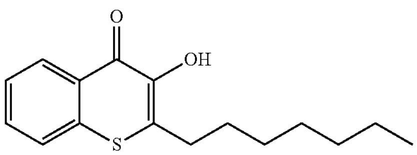 | 5 | B. subtilis<br>S. aureus NCTC-8325<br>S. aureus USA 300<br>S. aureus Mu50 | 25 μM<br>30 μM<br>30 μM<br>25 μM<br>35 μM | 6.91 μg/mL<br>8.29 μg/mL<br>8.29 μg/mL<br>6.91 μg/mL<br>9.67 μg/mL |
| 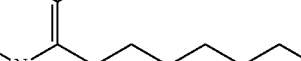 | 6 | B. subtilis<br>S. aureus NCTC 8325<br>S. aureus USA 300<br>S. aureus Mu50<br>S. aureus DSM18827<br>C. albicans | 125 μM<br>100 μM<br>150 μM<br>150 μM<br>150 μM<br>100 μM | 34.4 μg/mL<br>27.5 μg/mL<br>41.3 μg/mL<br>41.3 μg/mL<br>41.3 μg/mL<br>27.5 μg/mL |

TABLE 2

| Structure | # | Organism | MIC (μM) | MIC (μg/mL) |
|---|---|---|---|---|
| 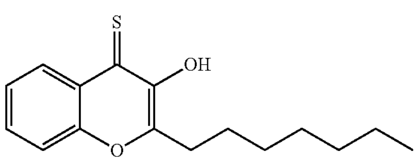 [SMILES: CCCCCCCc1sc2ccccc2c(=O)c1O] | 7 | NCTC-8325<br>USA 300<br>Mu50<br>DSM11827 | 60 μM<br>60 μM<br>50 μM<br>72.5 μM | 16.58 μg/mL<br>16.58 μg/mL<br>13.82 μg/mL<br>20.04 μg/mL |
| 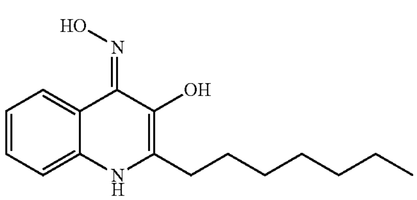 [SMILES: CCCCCCCc1[nH]c2ccccc2/c(=N\O)c1O] | 8 | NCTC-8325<br>USA 300<br>Mu50<br>DSM11827 | 200 μM<br>100 μM<br>100 μM<br>150 μM | 54.87 μg/mL<br>27.44 μg/mL<br>27.44 μg/mL<br>41.15 μg/mL |
| 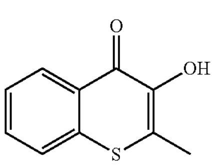 | 9 | NCTC-8325<br>USA 300<br>Mu50<br>DSM11827 | >1000 μM<br>>1000 μM<br>>1000 μM<br>>1000 μM | >192 μg/mL<br>>192 μg/mL<br>>192 μg/mL<br>>192 μg/mL |

TABLE 2-continued

| | | | |
|---|---|---|---|
| 10 | NCTC-8325 | 50 µM | 11.72 µg/mL |
| | USA 300 | 50 µM | 11.72 µg/mL |
| | Mu50 | 50 µM | 11.72 µg/mL |
| | DSM11827 | 50 µM | 11.72 µg/mL |
| 11 | NCTC-8325 | 35 µM | 10.3 µg/mL |
| | USA 300 | 35 µM | 10.3 µg/mL |
| | Mu50 | 40 µM | 11.78 µg/mL |
| | DSM11827 | 40 µM | 11.78 µg/mL |

Example 13: Toxicological Testing with Human Embryonic Kidney Cell Line HEK-293

Figure 2:
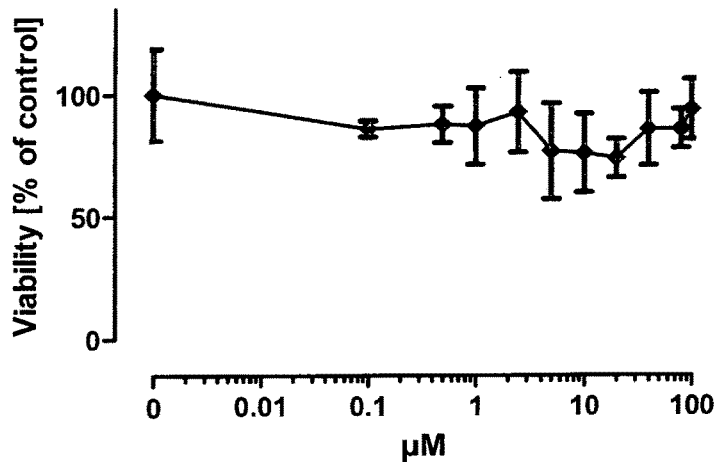
FIG. 2: Toxicological testing of compound 5 from 0-100 µM with human embryonic kidney cell line HEK-293. Viability measured by resazurin reduction after 24 h.
Figure 3:
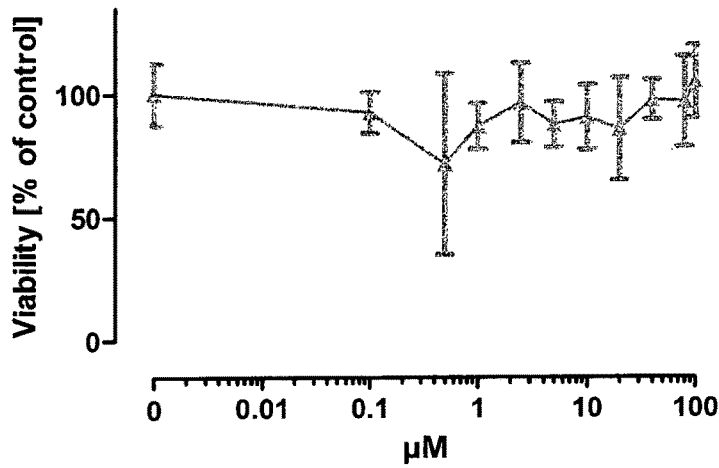
FIG. 3: Toxicological testing of compound 10 from 0-100 µM with human embryonic kidney cell line HEK-293. Viability measured by resazurin reduction after 24 h.

Compounds 3, 5, and 10 were toxicologically tested with human embryonic kidney cell line HEK-293 at concentrations varying from 0 to 100 µM (cf. FIGS. 1 to 3). The viability was measured by resazurin reduction after 24 h. Cell toxicity starting at 40 µM was found for compound 3 (cf. FIG. 1), while no cell toxicity was observed for compounds 5 and 10 up to 100 µM (cf. FIGS. 2 and 3).

Figure 4:
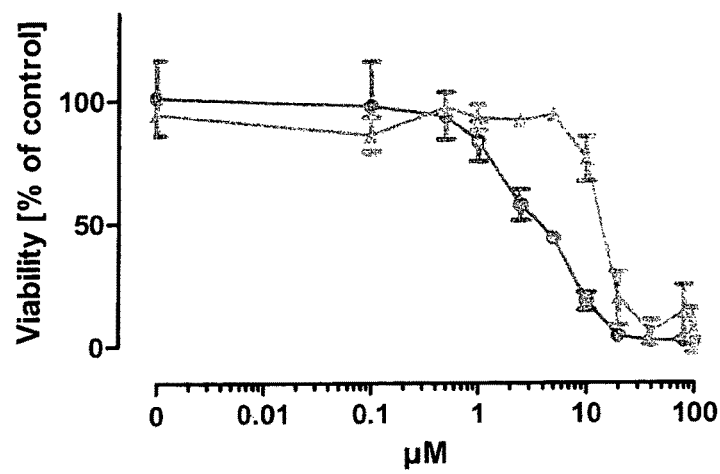
FIG. 4: Toxicological testing of compound 3 from 0-100 µM with developing neurons in the LUHMES d2-3 assay (general cytotoxicity (triangles); inhibition of neurite outgrowth (circles)).
Figure 5:
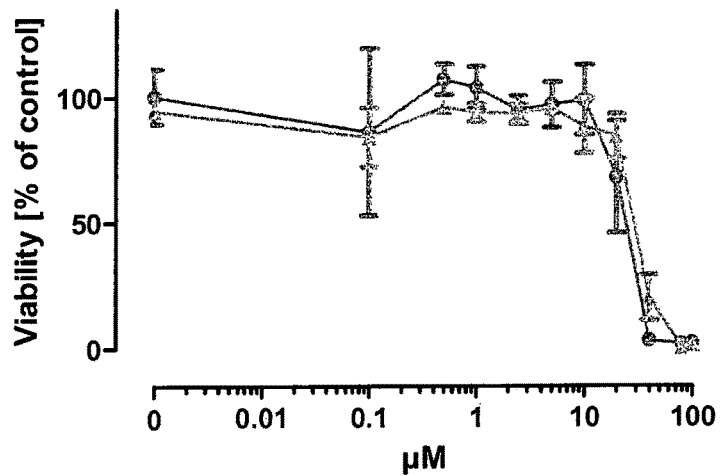
FIG. 5: Toxicological testing of compound 5 from 0-100 µM with developing neurons in the LUHMES d2-3 assay (general cytotoxicity (triangles); inhibition of neurite outgrowth (circles)).
Figure 6:
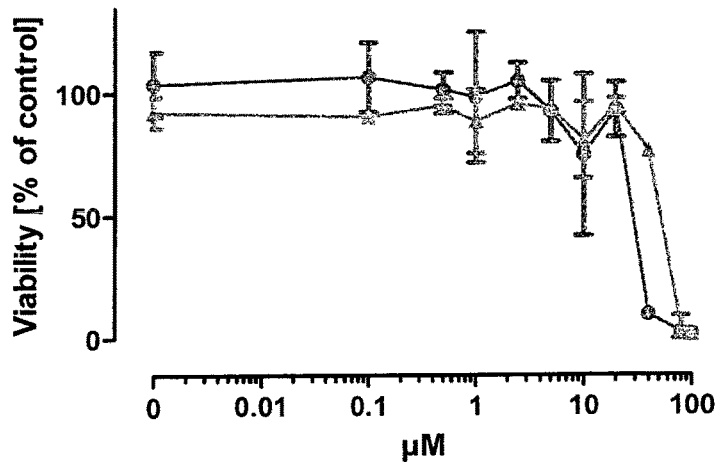
FIG. 6: Toxicological testing of compound 10 from 0-100 µM with developing neurons in the LUHMES d2-3 assay (general cytotoxicity (triangles); inhibition of neurite outgrowth (circles)).

Example 14: Toxicological Testing with Developing Neurons in the LUHMES d2-3 Assay Compounds 3, 5, and 10 were toxicologically tested with developing neurons in the LUHMES d2-3 assay at concentrations varying from 0 to 100 µM (cf. FIGS. 4 to 6). For compound 3, general cytotoxicity starting above 10 µM (orange line) and inhibition of neurite outgrowth starting above 2.5 µM (green line) was observed (cf. FIG. 4). In the case of compound 5 (cf. FIG. 5), general cytotoxicity (orange line) and inhibition of neurite outgrowth each started above 40 µM (green line). For compound 10 (cf. FIG. 6), general cytotoxicity (orange line) started at 80 µM and inhibition of neurite outgrowth started at 40 µM (green line).

Example 15: Synthesis of 2-heptyl-3-hydroxy-4H-thiochromene-4-thione, 1,4-S-PQS (Compound 12)

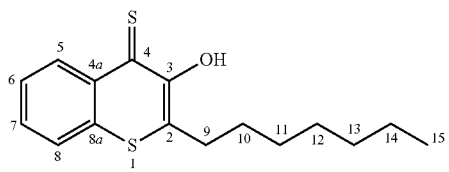

Under nitrogen atmosphere 54.4 mg (0.197 mmol) 1-S-PQS (Compound 5) and 65.6 mg (0.295 mmol) phosphorus $P_2S_5$ were dissolved in 2.4 mL pyridine and the solution was refluxed for 4 h at 170° C. The orange colored mixture was cooled to room temperature and poured into ice. Then it was brought to pH 7 using 6 M HCl solution. The murky ochre colored suspension was extracted with DCM three times and the red colored organic layers were combined and washed with 1 M HCl solution three times. The solved crude product was dried over $MgSO_4$, the solvent was evaporated and the red residue was recrystallized in methanol. The red precipitate was purified by silica gel chromatography (petroleum ether/ethyl acetate 1:4) and the product was obtained as dark violet/black crystalline solid (41.4 mg, 72%), Rf=0.19 (petroleum ether/ethyl acetate 2:1). MS(ESI): m/z calculated for $C_{16}H_{20}OS_2+H^+$: 293.1 $[M+H]^+$, found: 292.8. $^1$H-NMR (DMSOd$_6$ 400 MHz) δ (ppm): 0.85 (t, J=7.0 Hz, 3H, H-15), 1.21-1.42 (m, 8H, H-11, H-12, H-13, H-14), 1.74 (p, J=7.5 Hz, 2H, H-10), 2.95 (t, J=7.8 Hz, 2H, H-9), 7.74 (ddd, J=1.7 Hz, 7.0 Hz, 8.4 Hz, 1H, H-6), 7.78 (ddd, J=1.6 Hz, 7.0 Hz, 8.5 Hz, 1H, H-7), 8.10 (dd, J=1.3 Hz, 7.5 Hz, 1H, H-8), 8.88 (dd, J=1.5 Hz, 8.1 Hz, 1H, H-5), 9.38 (s, 1H, OH). $^{13}$C-NMR (DMSOd$_6$ 100 MHz) δ (ppm): 13.75 (C-15), 22.05, 31.03, 28.58 (C12-C14), 28.31 (C-11), 28.41 (C-10), 31.91 (C-9), 127.08 (C-8), 128.68 (C-6), 130.36 (C-7), 131.04 (C-2), 132.11 (C-5), 132.66 (C-8a), 135.43 (C-4a), 152.14 (C-3), 185.78 (C-4).

Example 16: In Vitro Inhibition of Elastase (LasB) with Compounds 6, 7, and 12

An in-vitro elastase assay was performed according to Cathcart et al. (G. R. Cathcart, B. F. Gilmore, B. Greer, P. Harriott, B. Walker, *Bioorganic & medicinal chemistry letters* 2009, 19, 6230-6232). For a typical in vitro elastase assay 82 µL buffer (0.05 M TRIS HCl, 2.5 mM $CaCl_2$, pH=7.2) and 5 µL of compound 6 solved in DMSO were added in a 96 well plate. 10 µL of 3 µg/mL elastase (solved in the same Tris/$CaCl_2$ buffer) were added and mixed with the compound. After incubation for 10 min at room temperature, 3 µL fluorogenic substrate Abz-peptide-Nba (2-aminobenzoyl-Ala-Gly-Leu-Ala-4-nitrobenzylamide) in DMF were added and the fluorescence measured for 90 min in one minute steps (excitation at 330 nm, emission at 460 nm). The slope of the resulting graph was used to calculate the enzymatic activity. The in vitro assay demonstrated a strong inhibition of elastase (LasB) by Compounds 6 ($IC_{50}$=4 µM; cf. FIG. 7), 7 and 12 (both $IC_{50}$=2 µM; cf. FIG. 8).

Example 17: In Situ Inhibition of Elastase (LasB) with Compound 6

Figure 9:
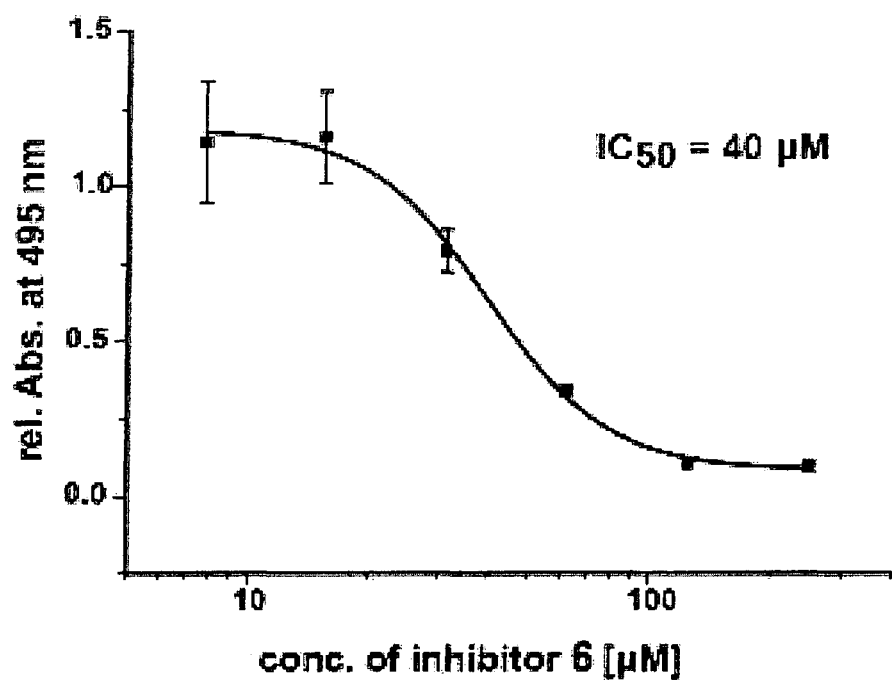
FIG. 9: In situ inhibition of elastase (LasB) with Compound 6

The in situ efficacy of Compound 6 was investigated by measuring the concentration dependent inhibition of elastolytic activity with life cultures of *P. aeruginosa*. The elastase assay was performed according to Calfee et al. (M. W. Calfee, J. P. Coleman, E. C. Pesci, *Proceedings of the National Academy of Sciences of the United States of America* 2001, 98, 11633-11637.) 10 µL of an overnight culture of PA14 was added to 3 mL of PTSB medium together with 15 µL of Compound 6 dissolved in DMSO at different stock concentrations. The culture was incubated for 24 h at 37° C. and 200 rpm. 1.4 mL of the culture was centrifuged and the supernatant filtered through a sterile filter. Thereafter, 0.5 mL ECR-buffer (0.1 M Tris HCl, 1 mM CaCl$_2$, pH=7.2) together with 10 mg Elastin-Congo Red was added to 0.5 ml of the sterile flow-through and the mixture incubated for 3 h at 37° C. and 1600 rpm. After the incubation, 0.1 mL Na$_2$EDTA (0.12 M) was added to quench the enzymatic reaction. After mixing, the solution was centrifuged (10 min at 6000 rpm) and 0.2 mL of the supernatant measured at 495 nm in a 96 well plate. It was observed that Compound 6 is an efficient inhibitor of elastolytic activity in situ resulting in sigmoidal inhibition behaviour with an IC$_{50}$ of 40 µM (cf. FIG. 9).

Example 18: Zinc Fluorescence Titration

Figure 10:
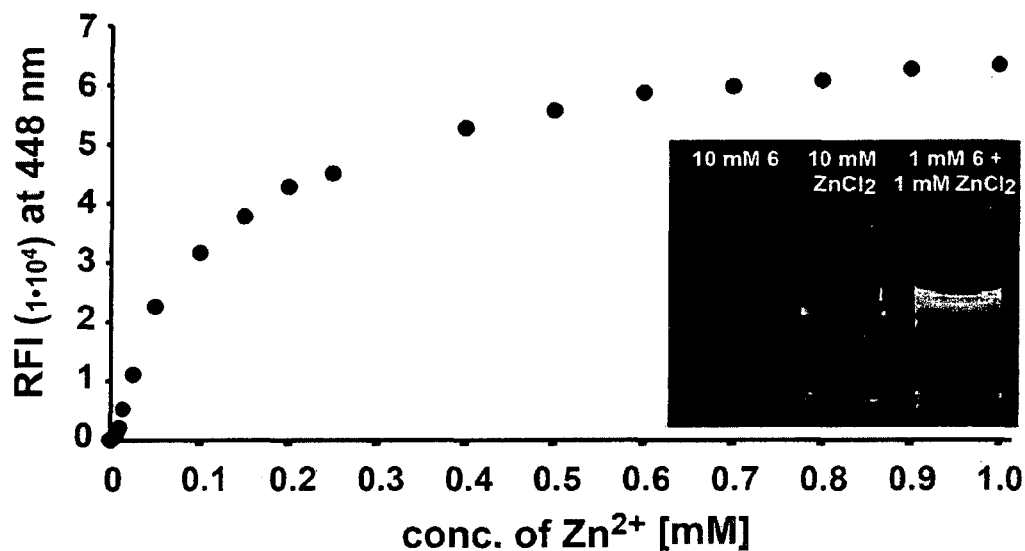
FIG. 10: Zinc fluorescence titration with Compound 6.
Figure 11:
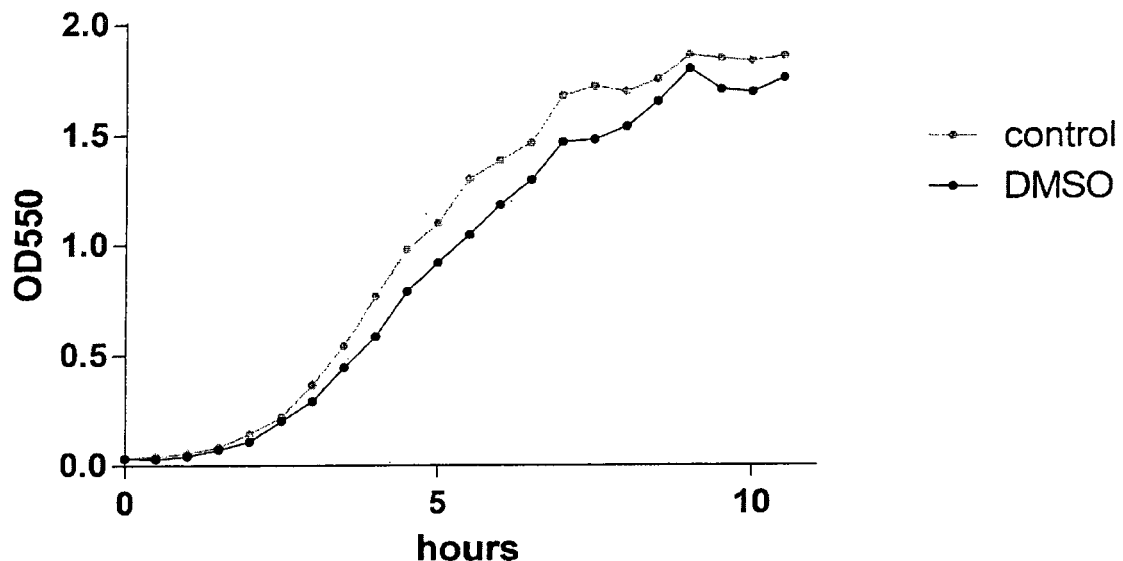
FIG. 11: Growth curves of *Moraxella catarrhalis* (Control). For this experiment, two types of controls, one without DMSO ("control") and one with DMSO ("DMSO"), were used to exclude adverse effects of the vehicle.

For a zinc fluorescence titration, 50 µL of Compound 6 (0.5 mM in EtOH) and 50 µl of a ZnCl$_2$ solution (2 mM-1 µM in EtOH) in an appropriate concentration were mixed and incubated for 5 min at room temperature in a 96 well plate. The fluorescence spectrum of the Compound 6-Zn-complex was measured from 300-600 nm at 26° C., with an excitation wavelength of 276 nm and 25 flashes/sec (cf. FIG. 10). The titration experiment reveals that zinc ion concentrations down to 2.5 µM can still be detected by fluorescence intensities two-fold over baseline.

Examples 19 and 20: Synthesis of the Compound Represented by the Formula (16) and of the Compound Represented by the Formula (14)

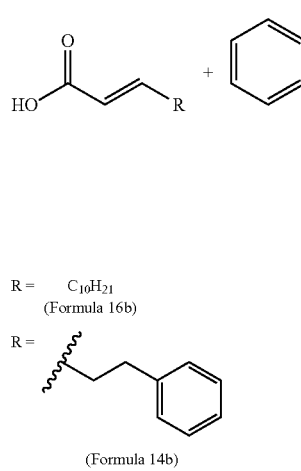

Synthesis of the Compound of Formula 16b

Under a nitrogen atmosphere, 1.28 g tridec-2-enoic acid (5.887 mmol) was dissolved in 3 ml dry DCM together with 1.0 ml thiophenol (9.863 mmol, 1.7 eq.) and cooled to 0° C. in an ice-bath. To this solution was added 6 ml TFMSA and the mixture was stirred for 5 min at 0° C. and afterwards 5 min at 130° C. The reaction was cooled to room temperature, poured on ice and the mixture extracted with DCM. The combined organic phases were washed two times with sat. NaHCO$_3$ solution and once with brine. The solution was dried with MgSO$_4$, filtered and the solvent evaporated. The residue was purified by column chromatography using silica 60 with petrol ether/DCM 4:1. The product was received as yellow oil. Yield: 583.7 mg (32.6%), R$_f$=0.1 (PE/DCM 4:1). $^1$H-NMR (CDCl$_3$ 399.79 MHz) δ (ppm): 0.88 (t, 3H, J=7.0 Hz, H-18), 1.20-1.35 (m, 14H, H$_{Alkyl}$), 1.46 (m, 2H, H-10), 1.71 (m, 2H, H-9), 2.79 (dd, 1H, J=16.3 Hz, J=11.1 Hz, H-3a), 3.04 (dd, 1H, J=16.3 Hz, J=3.1 Hz, H-3b), 3.49 (m, 1H, H-2), 7.16 (m, 1H, H-6), 7.26 (m, 1H, H-8), 7.37 (m, 1H, H-7), 8.07 (dd, 1H, J=8 Hz, J=1.3 Hz, H-5). $^{13}$C-NMR (CDCl$_3$ 100.53 MHz) δ (ppm): 14.3 (C-18), 22.8, 29.3, 29.4, 29.5, 29.6, 29.7, 32.0 (C-11 to C-17), 26.8 C-10), 34.7 (C-9), 41.8 (C-2), 46.4 (C-3), 125.0 (C-6), 127.8 C-8), 129.0 (C-5), 130.8 (C-4a), 133.6 (C-7), 141.9 (C-8a), 194.9 (C-4).

Synthesis of the Compound of Formula 14b

Under a nitrogen atmosphere, 1.25 g (E)-5-phenylpent-2-enoic acid (7.09 mmol) was dissolved in 3.6 ml dry DCM together with 1.2 ml thiophenol (11.84 mmol, 1.7 eq.) and cooled to 0° C. in an ice-bath. To this solution was added 7.2 ml TFMSA and the mixture was stirred for 5 min at 0° C. and afterwards 5 min at 130° C. The reaction was cooled to room temperature, poured on ice and the mixture extracted with DCM. The combined organic phases were washed two times with sat. NaHCO$_3$ solution and once with brine. The solution was dried with MgSO$_4$, filtered and the solvent evaporated. The residue was purified by column chromatography using silica 60 with petrol ether/DCM 1:1. The product was received as yellow oil. Yield: 712.2 mg (37%), R$_f$=0.5 (PE/DCM 1:1). $^1$H-NMR (CDCl$_3$ 399.79 MHz) δ (ppm): 2.05 (m, 2H, H-9), 2.81 (m, 2H, overlapping, H-10), 2.84 (dd, 1H, overlapping, J=16.3 Hz, J=10.5 Hz, H-3a), 3.07 (dd, 1H, J=16.3 Hz, 3.2 Hz, H-3b), 3.47 (m, 1H, H-2), 7.13-7.24 (m, 4H, overlapping, H$_{Ar}$ and H-6), 7.24-7.33 (m, 3H, overlapping, H$_{Ar}$ and H-8), 7.40 (m, 1H, H-7), 8.08 (dd, 1H, J=8.1 Hz, 1.5 Hz, H-5). $^{13}$C-NMR (CDCl$_3$ 100.53 MHz) δ (ppm): 32.9 (C-10), 36.1 (C-9), 40.9 (C-2), 46.3 (C-3), 125.2 (C-6), 126.4 (C-4'), 127.8 (C-8), 128.6 (2C, C-2'), 128.8 (2C, C-3'), 129.1 (C-5), 130.8 (C-4a), 133.7 (C-7), 140.7 (C-1'), 141.4 (C-8a), 194.5 (C-4).

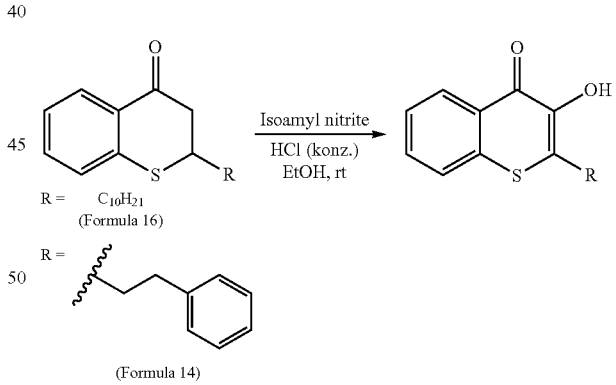

Synthesis of the Compound Represented by Formula 16

259 mg of the Compound of Formula 16b was dissolved in 9 ml EtOH and 4.5 ml concentrated HCl was added. To this mixture 3.7 ml isoamyl nitrite (27.5 mmol, 32 eq.) was added and the mixture stirred at room temperature overnight. 40 ml water was added and the mixture extracted with ethyl acetate. The combined organic phases were washed once with brine. The solution was dried with MgSO$_4$, filtered and the solvent evaporated. The residue was purified by column chromatography using silica 60 with petrol ether/ethyl acetate 7:1, $R_f$=0.56 (PE:EA 7:1). The product (81.3 mg) was received slightly contaminated and was further purified by prep. HPLC using a linear gradient from 5% MeCN+0.1% formic acid (FA)/95% water+0.1% FA to 95% MeCN+0.1% FA/5% water in 45 min to receive the product as yellow solid (47 mg, 15%). $^1$H-NMR (CDCl$_3$ 399.79 MHz) δ (ppm): 0.88 (m, 3H, H-18), 1.16-1.38 (m, 12H, H-12 to H-17), 1.42 (m, 2H, H-11), 1.75 (m, 2H, H-10), 2.84 (m, 2H, H-9), 7.52 (m, 1H, H-6), 7.59 (m, 1H, H-7), 7.64 (d, 1H, J=7.7 Hz, H-8), 8.53 (d, 1H, J=7.8 Hz, H-5). $^{13}$C-NMR (CDCl$_3$ 100.53 MHz) δ (ppm): 14.3 (H-18), 22.8, 29.37, 29.44 (2C), 29.6, 29.7, 32.0 (C-11-17), 29.1 (C-10), 31.3 (C-9), 126.1 (C-8), 126.7 (C-6), 128.9 (C-5), 129.0 (C-4a), 129.5 (C-2), 130.9 (C-7), 138.0 (C-8a), 144.1 (C-3), 174.1 (C-4).

Synthesis of the Compound Represented by Formula 14

Under a nitrogen atmosphere, 712.2 mg of the Compound of Formula 14b (2.65 mmol) was dissolved in 21 ml MeOH/EtOH 1:1 together with 1.1 ml isoamyl nitrite (8.17 mmol, 3.1 eq.) and the mixture cooled on ice. 1.6 ml concentrated HCl was added at 0° C. and the mixture stirred at 0° C. for 10 min and afterwards warmed up to room temperature and stirred at this temperature for 1 h. Afterwards the mixture was refluxed at 80° C. for 3 h. Approximately half of the solvent was evaporated and the residue poured in water. The mixture was extracted with ether and the combined organic phases were washed once with brine. The solution was dried with MgSO$_4$, filtered and the solvent evaporated. The residue was purified by column chromatography using silica 60 with petrol ether/ethyl acetate 5:1. The product was received as red-brown solid. Yield: 152.6 mg (20%), $R_f$=0.58 (PE/EA 5:1). $^1$H-NMR (CDCl$_3$ 399.79 MHz) δ (ppm): 3.04-3.16 (m, 4H, H-9/H-10), 7.19-7.33 (m, 5H, H-2'-H-4'), 7.52 (m, 1H, H-6), 7.59 (m, 1H, H-7), 7.62 (m, 1H, H-8), 8.54 (d, J=8.2 Hz, 1H). $^{13}$C-NMR (CDCl$_3$ 100.53 MHz) δ (ppm): 33.4 (C-9), 34.9 (C-10), 126.2 (C-8), 126.5 (C$_{Ar}$), 126.8 (C-6), 127.6 (C-2), 128.6 (C$_{Ar}$), 128.7 (C$_{Ar}$), 128.9 (C-5), 129.0 (C-4a), 130.9 (C-7), 137.9 (C-8a), 140.5 (C-1'), 144.3 (C-3), 174.2 (C-4).

Example 21: Determination of the Minimum Inhibitory Concentration (MIC) for the Compounds Represented by the Formulas (14) and (16) with the Pathogenic USA 300 (MRSA) Strain of *S. aureus*

Minimum inhibitory concentrations (MIC) for the compounds represented by the Formulas (14) and (16) with the pathogenic MRSA strains of *S. aureus* USA 300 were determined in 96-well plates with serial dilutions in LB medium. The results are summarized in Table 3.

TABLE 3

| Formula | Strain | MIC (µM) | MIC (µg/mL) |
|---|---|---|---|
| Formula (14) | S. aureus USA 300 | 40 µM | 11.3 µg/mL |
| Formula (16) | S. aureus USA 300 | >100 µM | >32 µg/mL |

Figure 12:
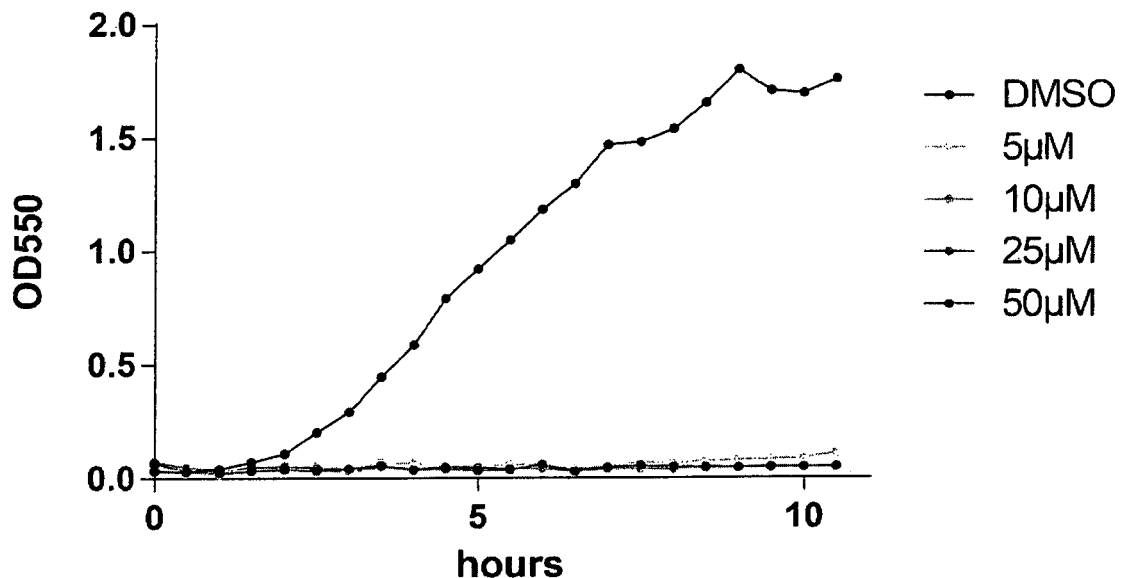
FIG. 12: Growth curves of *Moraxella catarrhalis* with 1-S-PQS (5) in concentration dependence. For this experiment, a control with DMSO ("DMSO") was used to exclude adverse effects of the vehicle.
Figure 13:
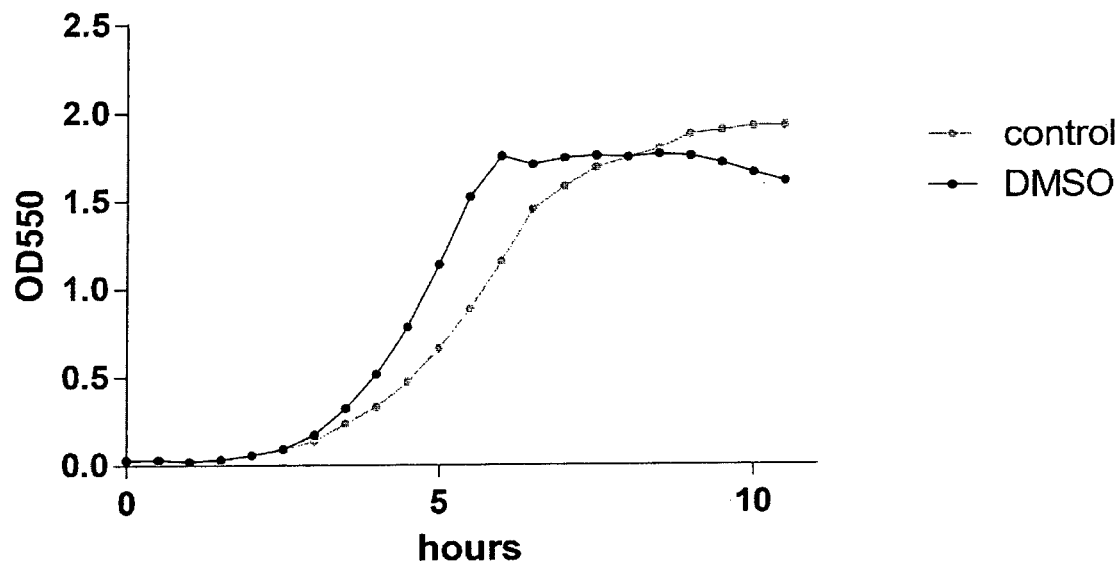
FIG. 13: Growth curves of *Neisseria meningitidis* (Control). For this experiment, two types of controls, one without DMSO ("control") and one with DMSO ("DMSO"), were used to exclude adverse effects of the vehicle.
Figure 14:
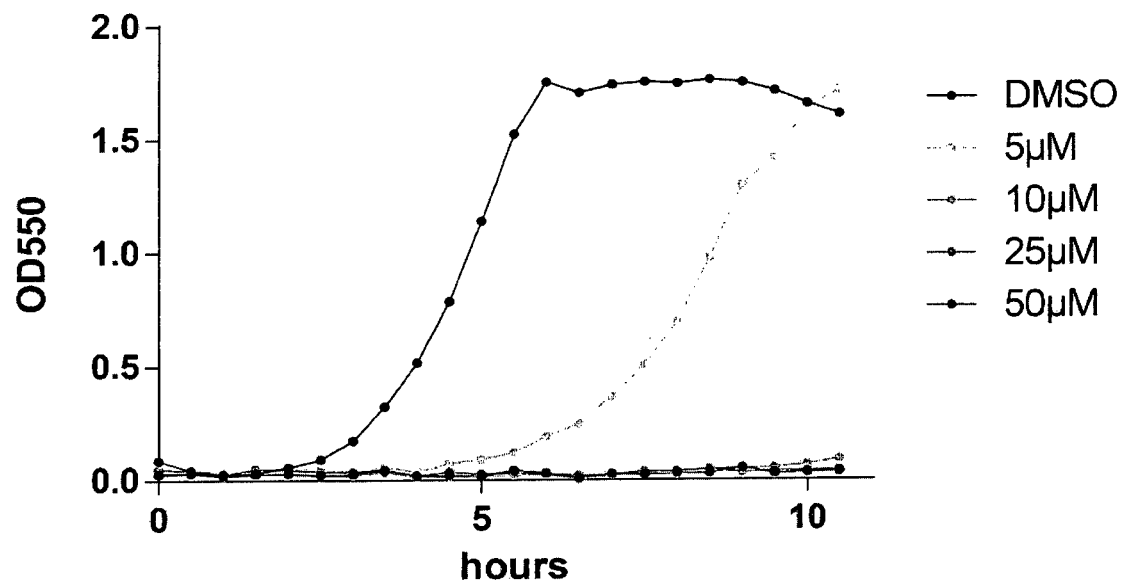
FIG. 14: Growth curves of *Neisseria meningitidis* with 1-S-PQS (5) in concentration dependence. For this experiment, a control with DMSO ("control") was used to exclude adverse effects of the vehicle.

Example 22: Determination of the Inhibitory Effect of 1-S-PQS (5) Against *Moraxella catarrhalis* and *Neisseria meningitidis* by Measuring Growth Curves in Comparison to an Untreated and a DMSO Treated Control The inhibitory effect of 1-S-PQS (5) against *Moraxella catarrhalis* and *Neisseria meningitidis* was determined by measuring growth curves in comparison to an untreated and a DMSO treated control (cf. FIGS. 11 to 14). Growth of *Neisseria meningitidis* was completely inhibited at 10 µM and *Moraxella catarrhalis* even at the lowest concentration tested (5 µM) corresponding to 1.4 µg/mL (cf. FIG. 12). *M. catarrhalis* is an important human pathogen responsible for otitis media in children and chronic obstructive pulmonary disease (COPD) in adults. Table 4 shows an overview of growth relative to DMSO control of the tested bacterium with 1-S-PQS.

TABLE 4

| | 1-S-PQS (5) | | | |
|---|---|---|---|---|
| Tested bacterium | 5 µM | 10 µM | 25 µM | 50 µM |
| Moraxella catarrhalis | 0.1 | 0.0 | 0.0 | 0.0 |
| Neisseria meningitidis | 0.4 | 0.0 | 0.0 | 0.0 |

Figure 15:
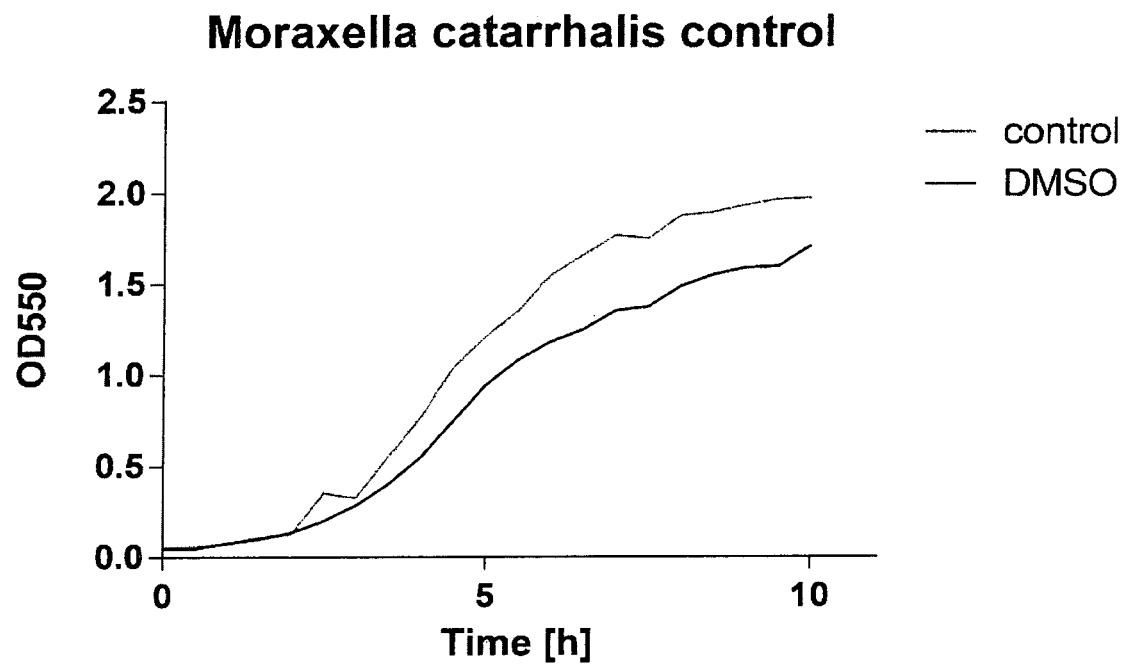
FIG. 15: Growth curves of *Moraxella catarrhalis* (control). Two types of controls, one without DMSO ("control") and one with DMSO ("DMSO"), were used to exclude adverse effects of the vehicle.
Figure 16:
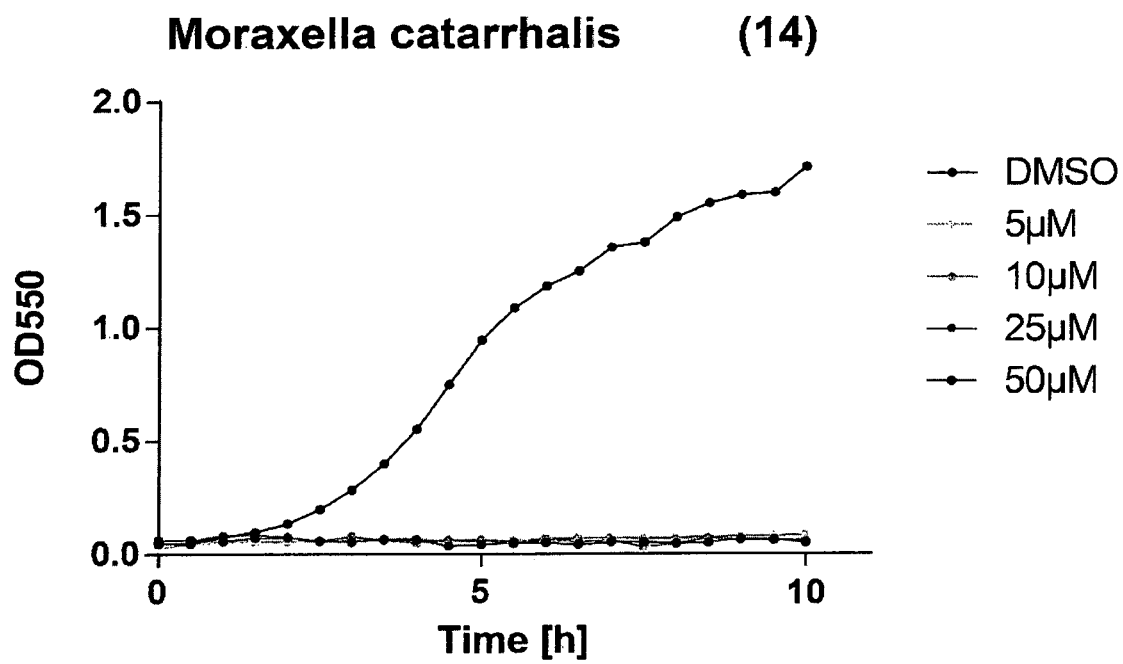
FIG. 16: Growth curves of *Moraxella catarrhalis* with the compound represent by the Formula (14) in concentration dependence. A control with DMSO ("DMSO") was used to exclude adverse effects of the vehicle.

Example 23: Determination of the Inhibitory Effect of the Compound Represented by the Formula (14) Against *Moraxella catarrhalis* by Measuring Growth Curves in Comparison to an Untreated and a DMSO Treated Control The inhibitory effect of the compound represented by the Formula (14) against *Moraxella catarrhalis* was determined by measuring growth curves in comparison to an untreated and a DMSO treated control (cf. FIGS. 15 and 16). The compound represented by the Formula (14) is also highly effective against *Moraxella catarrhalis* and completely inhibited growth at the lowest concentration tested of 5 µM (cf. FIG. 16).

Figure 17:
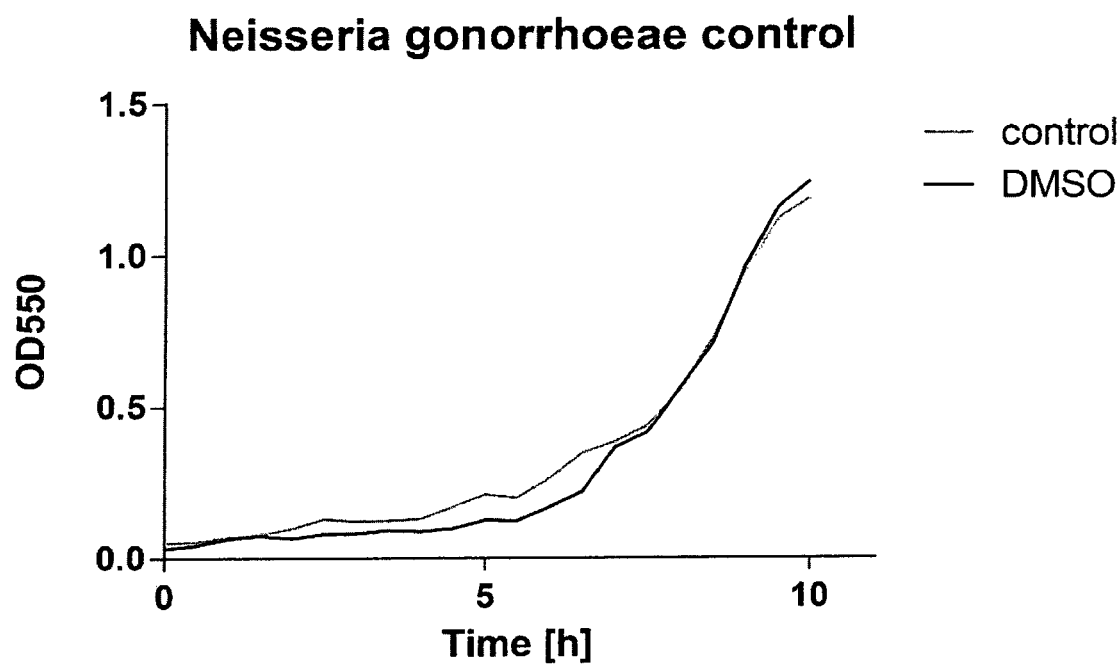
FIG. 17: Growth curves of *Neisseria gonorrhoeae* (control). For this experiment, two types of controls, one without DMSO ("control") and one with DMSO ("DMSO"), were used to exclude adverse effects of the vehicle.
Figure 18:
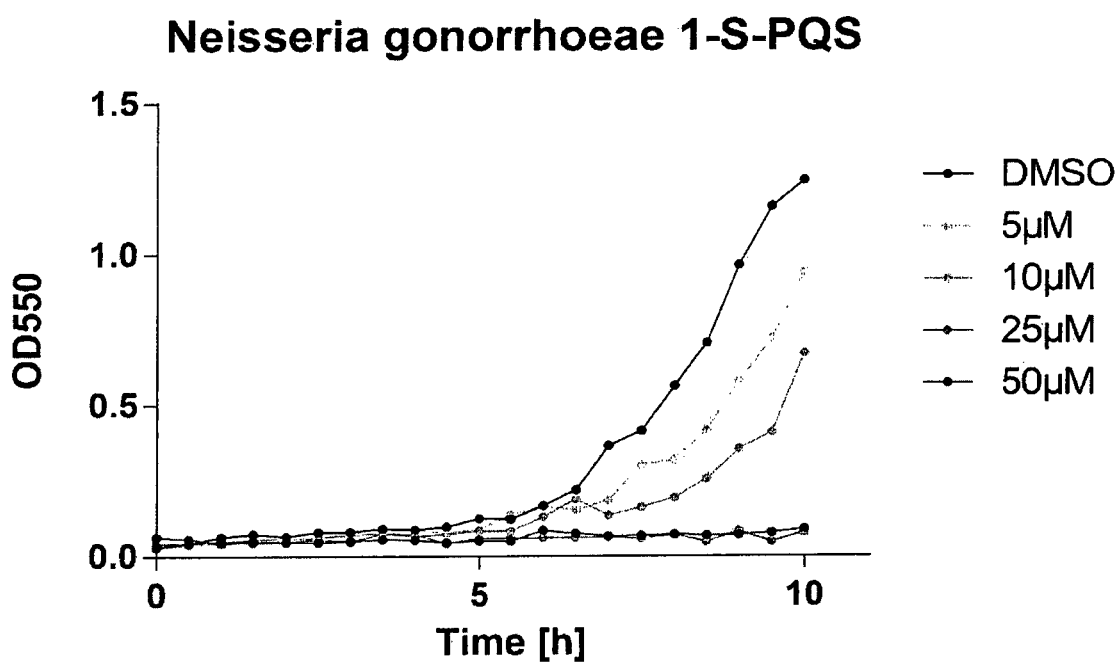
FIG. 18: Growth curves of *Neisseria gonorrhoeae* with 1-S-PQS (5) in concentration dependence. A control with DMSO ("DMSO") was used to exclude adverse effects of the vehicle.
Figure 19:
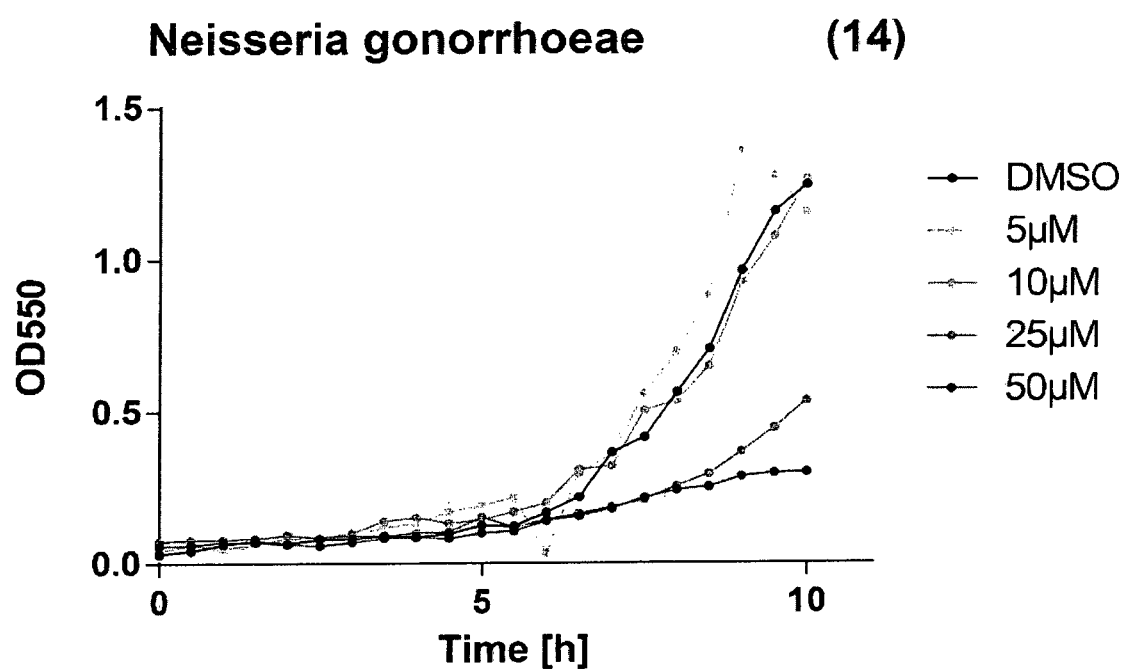
FIG. 19: Growth curves of *Neisseria gonorrhoeae* with the compound represented by the Formula (14) in concentration dependence. A control with DMSO ("DMSO") was used to exclude adverse effects of the vehicle.

Example 24: Determination of the Inhibitory Effect of 1-S-PQS (5) and the Compound Represented by the Formula (14) Against *Neisseria gonorrhoeae* by Measuring Growth Curves in Comparison to an Untreated and a DMSO Treated Control The inhibitory effect of 1-S-PQS (5) and the compound represented by the Formula (14) against *Neisseria gonorrhoeae* was determined by measuring growth curves in comparison to an untreated and a DMSO treated control (cf. FIGS. 17 to 19). *Neisseria gonorrhoeae* was completely inhibited by 1-S-PQS (5) at 25 µM (cf. FIG. 18). The compound represented by the Formula (14) was effective against *N. gonorrhoeae* around 25-50 µM (cf. FIG. 19).

The invention claimed is:
1. A method for treating bacterial or fungal infections in a subject in need of said treatment, the method comprising administering to said subject from 1 µg to 100 mg per kilogram of body weight per day, from 0.1 mg to 50 mg per kilogram of body weight per day, or from 10 mg to 4 g per kilogram of body weight per day of a compound represented by Formula (1) or a pharmaceutically acceptable salt thereof

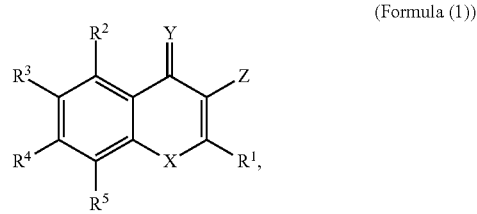

(Formula (1))

wherein
$R^1$ is selected from the group consisting of a substituted or unsubstituted alkyl group having from 4 to 11 carbon atoms, a substituted or unsubstituted cycloalkyl group having from 4 to 12 carbon atoms, a substituted or unsubstituted alkenyl group having from 4 to 11 carbon atoms, a substituted or unsubstituted cycloalkenyl group having from 4 to 12 carbon atoms, a substituted or unsubstituted alkynyl group having from 4 to 11 carbon atoms, a substituted or unsubstituted aryl group;
X is S;
Y is O;
Z is $OR^8$, wherein $R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group;
$R^2$ to $R^5$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a halogen atom, a trifluoromethyl group, $-NE^1E^2$, $-NO_2$, $-CN$, $-OE^3$, $-C(O)E^4$, $-C(O)NE^5E^6$, $-COOE^7$, and $-SO_3E^8$, wherein $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group;
wherein substituents of the substituted alkyl group, the substituted cycloalkyl group, the substituted alkenyl group, the substituted cycloalkenyl group, the substituted alkynyl group, and the substituted aryl group are selected from the group consisting of a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a halogen atom, $-NL^1L^2$, $-NO_2$, $-CN$, $-OL^3$, $-C(O)L^4$, $-C(O)NL^5L^6$, $-COOL^7$, and $-SO_3L^8$, wherein $L^1$ to $L^8$ are each independently selected from a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, and an aryl group having 1 to 3 rings; and
wherein one or more tetravalent carbon atoms together with the hydrogen atoms bonded thereto, when present, in each of the alkyl group, the cycloalkyl group, the alkenyl group, the cycloalkenyl group, and the alkynyl group may each independently be substituted by a member selected from the group consisting of O, $(OCH_2CH_2)_nO$, S, $(SCH_2CH_2)_mS$, C(O), C(O)O, $NR^{10}$, and $C(O)NR^{11}$, wherein n and m are each independently an integer from 1 to 6 and $R^{10}$ and $R^{11}$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, $-OG^1$, $-C(O)G^2$, $-C(O)NG^3G^4$, $-COOG^5$, and $-SO_2G^6$, wherein $G^1$ to $G^6$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, and an aryl group having 1 to 3 rings.

2. The method according to claim 1, wherein the bacterial infection is caused by gram-positive bacteria selected from the group consisting of *Bacillus subtilis, Bacillus anthracis, Bacillus cereus, Bacillus licheniformis, Bacillus thuringiensis, Bacillus larvae, Staphylococcus aureus, Staphylococcus epidermidis, Staphylococcus saprophyticus, Staphylococcus lugdunensis, Staphylococcus schleiferi, Staphylococcus caprae, Streptococcus pneumoniae, Streptococcus viridans, Streptococcus pyogenes, Streptococcus agalactiae, Enterococcus faecalis, Enterococcus faecium, Listeria monocyto-*

*genes, Listeria welshimeri, Nocardia asteroides*, and *Rhodococcus equi*; mycobacteria selected from the group consisting of *Mycobacterium tuberculosis, Mycobacterium bovis, Mycobacterium leprae, Mycobacterium ulcerans, Mycobacterium kanasasii, Mycobacterium avium*, and *Mycobacterium paratuberculosis*; or gram negative bacteria selected from the group consisting of *Acinetobacter baumannii, Enterobacter cloacae, Escherichia coli, Helicobacter pylori, Haemophilus influenzae, Klebsiella pneumoniae, Legionella pneumophila, Moraxella catarrhalis, Neisseria gonorrhoeae, Neisseria meningitidis, Pseudomonas aeruginosa, Pseudomonas putida, Proteus mirabilis, Serratia marcescens, Salmonella enteritidis*, and *Salmonella typhi*, and wherein the fungal infection is caused by fungal species selected from the group consisting of *Candida albicans, Candida dubliniensis, Trichophyton rubrum*, and *Epidermophyton floccosum*.

3. A method for disinfecting a substrate selected from the group consisting of medical tools, medical equipment, floor, linen, paper, medical and industrial surfaces, said method comprising applying to the substrate a compound at a concentration ranging from 0.001 M to 5 M, from 0.01 M to 5 M, or from 0.1 M to 2 M, the compound represented by Formula (1) or a pharmaceutically acceptable salt thereof

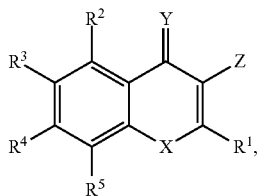

(Formula (1))

wherein $R^1$ is selected from the group consisting of a substituted or unsubstituted alkyl group having from 4 to 11 carbon atoms, a substituted or unsubstituted cycloalkyl group having from 4 to 12 carbon atoms, a substituted or unsubstituted alkenyl group having from 4 to 11 carbon atoms, a substituted or unsubstituted cycloalkenyl group having from 4 to 12 carbon atoms, a substituted or unsubstituted alkynyl group having from 4 to 11 carbon atoms, a substituted or unsubstituted aryl group;

X is S;

Y is O;

Z is $OR^8$, wherein $R^8$ is selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group;

$R^2$ to $R^5$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group, a halogen atom, a trifluoromethyl group, $-NE^1E^2$, $-NO_2$, $-CN$, $-OE^3$, $-C(O)E^4$, $-C(O)NE^5E^6$, $-COOE^7$, and $-SO_3E^8$, wherein $E^1$ to $E^8$ are each independently selected from the group consisting of a hydrogen atom, a substituted or unsubstituted alkyl group, a substituted or unsubstituted cycloalkyl group, a substituted or unsubstituted alkenyl group, a substituted or unsubstituted cycloalkenyl group, a substituted or unsubstituted alkynyl group, a substituted or unsubstituted aryl group;

wherein substituents of the substituted alkyl group, the substituted cycloalkyl group, the substituted alkenyl group, the substituted cycloalkenyl group, the substituted alkynyl group, and the substituted aryl group are selected from the group consisting of a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, a halogen atom, $-NL^1L^2$, $-NO_2$, $-CN$, $-OL^3$, $-C(O)L^4$, $-C(O)NL^5L^6$, $-COOL^7$, and $-SO_3L^8$, wherein $L^1$ to $L^8$ are each independently selected from a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, and an aryl group having 1 to 3 rings; and wherein one or more tetravalent carbon atoms together with the hydrogen atoms bonded thereto, when present, in each of the alkyl group, the cycloalkyl group, the alkenyl group, the cycloalkenyl group, and the alkynyl group may each independently be substituted by a member selected from the group consisting of O, $(OCH_2H_2)_nO$, S, $(SCH_2CH_2)_m$, S, $C(O)$, $C(O)O$, $NR^{10}$, and $C(O)NR^{11}$, wherein n and m are each independently an integer from 1 to 6 and $R^{10}$ and $R^{11}$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, an aryl group having 1 to 3 rings, $-OG^1$, $-C(O)G^2$, $-C(O)NG^3G^4$, $-COOG^5$, and $-SO_2G^6$, wherein $G^1$ to $G^6$ are each independently selected from the group consisting of a hydrogen atom, a branched or linear alkyl group having 1 to 6 carbon atoms, a cycloalkyl group having 4 to 8 carbon atoms, a branched or linear alkenyl group having 2 to 6 carbon atoms, a cycloalkenyl group having 4 to 8 carbon atoms, a branched or linear alkynyl group having 2 to 6 carbon atoms, and an aryl group having 1 to 3 rings.

4. The method according to claim 1, wherein $R^1$ is a heptyl group.

5. The method according to claim 1, wherein Z is OH.

6. The method according to claim 1, wherein $R^2$ to $R^5$ each a hydrogen atom.

7. The method according to claim 1, wherein the compound is selected from the group consisting of the compounds represented by the following Formulas (2) to (4), or a pharmaceutically acceptable salt thereof:

Formula (2)

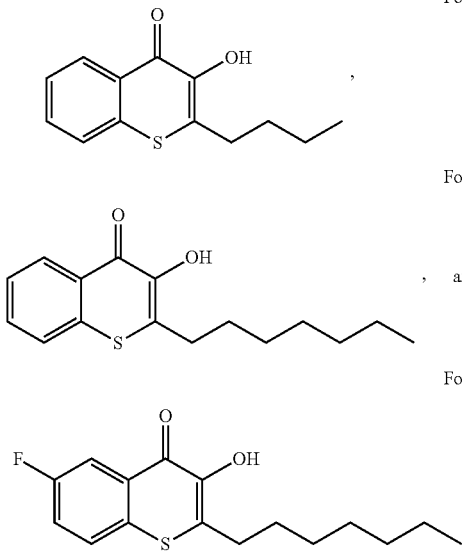

Formula (3)

, and

Formula (4)

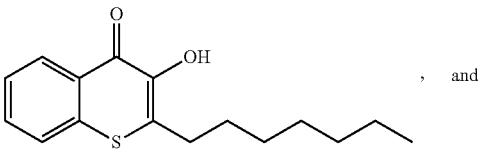

Formula (3)

, and

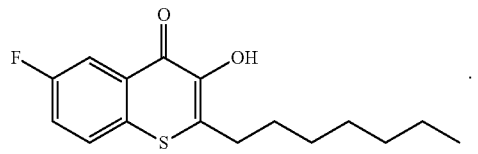

Formula (4)

8. The method according to claim 1, wherein the compound is administered as a pharmaceutical composition comprising the compound in a pharmaceutically active amount, and optionally a pharmaceutically acceptable carrier, excipient or diluent.

9. The method according to claim 3, wherein $R^1$ is a heptyl group.

10. The method according to claim 3, wherein Z is OH.

11. The method according to claim 3, wherein $R^2$ to $R^5$ are each a hydrogen atom.

12. The method according to claim 3, wherein the compound is selected from the group consisting of the compounds represented by the following Formulas (2) to (4), or a pharmaceutically acceptable salt thereof:

Formula (2)

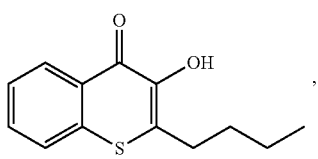

13. A method for treating bacterial or fungal infections in a subject in need of treatment, the method comprising administering to said subject from 1 μg to 100 mq per kilogram of body weight per day, from 0.1 mq to 50 mg per kilogram of body weight per day, or from 10 mg to 4 g per kilogram of body weight per day of a compound selected from the group consisting of compounds represented by the following Formulas (2) to (4, or a pharmaceutically acceptable salt thereof:

Formula (2)

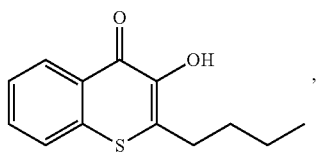

Formula (3)

, and

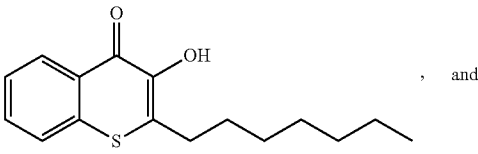

Formula (4)

* * * * *